United States Patent
Desai et al.

(10) Patent No.: US 9,446,003 B2
(45) Date of Patent: Sep. 20, 2016

(54) PRION FREE NANOPARTICLE COMPOSITIONS AND METHODS OF MAKING THEREOF

(71) Applicant: Abraxis BioScience, LLC, Los Angeles, CA (US)

(72) Inventors: Neil P. Desai, Los Angeles, CA (US); Viktor Peykov, Los Angeles, CA (US); Patrick Soon-Shiong, Los Angeles, CA (US)

(73) Assignee: ABRAXIS BIOSCIENCE, LLC, Los Angeles, CA (US)

( * ) Notice: Subject to any disclaimer, the term of this patent is extended or adjusted under 35 U.S.C. 154(b) by 0 days.

(21) Appl. No.: 14/191,279

(22) Filed: Feb. 26, 2014

(65) Prior Publication Data

US 2014/0296353 A1    Oct. 2, 2014

Related U.S. Application Data

(63) Continuation of application No. 12/761,292, filed on Apr. 15, 2010, now abandoned.

(60) Provisional application No. 61/169,665, filed on Apr. 15, 2009, provisional application No. 61/238,052, filed on Aug. 28, 2009.

(51) Int. Cl.
| | | |
|---|---|---|
| *A61K 31/337* | (2006.01) | |
| *A61K 47/42* | (2006.01) | |
| *A61K 9/51* | (2006.01) | |
| *A61K 9/16* | (2006.01) | |
| *B82Y 5/00* | (2011.01) | |
| *G01N 33/68* | (2006.01) | |

(52) U.S. Cl.
CPC .......... *A61K 9/5169* (2013.01); *A61K 9/1658* (2013.01); *A61K 31/337* (2013.01); *A61K 47/42* (2013.01); *B82Y 5/00* (2013.01); *G01N 33/6896* (2013.01); *G01N 2800/2828* (2013.01); *Y10S 210/905* (2013.01)

(58) Field of Classification Search
None
See application file for complete search history.

(56) References Cited

U.S. PATENT DOCUMENTS

| | | |
|---|---|---|
| 5,362,478 A | 11/1994 | Desai et al. |
| 5,439,686 A | 8/1995 | Desai et al. |

(Continued)

FOREIGN PATENT DOCUMENTS

| | | |
|---|---|---|
| CN | 1135235 C | 5/1995 |
| CN | 1739029 A | 2/2006 |

(Continued)

OTHER PUBLICATIONS

G Kaul, M Amiji. "Protein Nanoparticles for Gene Delivery." "Chapter 27, Polymeric Gene Delivery: Principles and Applications." CRC Press LLC, 2005, pp. 429-447, ISBN 0-8493-1934-X/05.*

(Continued)

*Primary Examiner* — Isaac Shomer
(74) *Attorney, Agent, or Firm* — Morrison & Foerster LLP

(57) ABSTRACT

The present invention provides prion-free compositions comprising nanoparticles comprising albumin and substantially water insoluble drugs. Also provided are methods of making prion-free compositions and methods of removing prion proteins from the nanoparticle compositions. Methods of using the compositions, as well as kits useful for carrying out the methods are also provided.

10 Claims, 9 Drawing Sheets

(56) References Cited

U.S. PATENT DOCUMENTS

| | | |
|---|---|---|
| 5,498,421 A | 3/1996 | Grinstaff et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,750,361 A | 5/1998 | Prusiner et al. |
| 5,916,596 A | 6/1999 | Desai et al. |
| 5,997,904 A | 12/1999 | Magdassi et al. |
| 6,096,331 A | 8/2000 | Desai et al. |
| 6,150,172 A | 11/2000 | Schmerr et al. |
| 6,506,405 B1 | 1/2003 | Desai et al. |
| 6,528,067 B1 | 3/2003 | Magdassi et al. |
| 6,537,579 B1 | 3/2003 | Desai et al. |
| 6,565,842 B1 | 5/2003 | Desai et al. |
| 6,652,884 B2 | 11/2003 | Falciani |
| 6,749,868 B1 | 6/2004 | Desai et al. |
| 6,753,006 B1 | 6/2004 | Desai et al. |
| 7,393,658 B2 | 7/2008 | Carbonell et al. |
| 7,771,751 B2 | 8/2010 | Desai et al. |
| 7,780,984 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,034,375 B2 | 10/2011 | Desai et al. |
| 8,034,765 B2 | 10/2011 | De et al. |
| 8,137,684 B2 | 3/2012 | Desai et al. |
| 8,138,229 B2 | 3/2012 | Desai et al. |
| 8,257,733 B2 | 9/2012 | Desai et al. |
| 8,268,348 B2 | 9/2012 | Desai et al. |
| 8,314,156 B2 | 11/2012 | Desai et al. |
| 8,735,394 B2 | 5/2014 | Desai et al. |
| 8,846,771 B2 | 9/2014 | Desai et al. |
| 8,853,260 B2 | 10/2014 | Desai et al. |
| 8,911,786 B2 | 12/2014 | Desai et al. |
| 8,927,019 B2 | 1/2015 | Desai et al. |
| 8,999,396 B2 | 4/2015 | Desai et al. |
| 9,012,518 B2 | 4/2015 | Desai et al. |
| 9,012,519 B2 | 4/2015 | Desai et al. |
| 9,061,014 B2 | 6/2015 | Seward et al. |
| 9,101,543 B2 | 8/2015 | Desai et al. |
| 9,149,455 B2 | 10/2015 | Desai et al. |
| 2002/0041859 A1 | 4/2002 | Prusiner et al. |
| 2003/0199425 A1 | 10/2003 | Desai et al. |
| 2004/0033224 A1 | 2/2004 | Van Holten et al. |
| 2004/0229280 A1* | 11/2004 | Hammond et al. ............ 435/7.1 |
| 2005/0004002 A1 | 1/2005 | Desai et al. |
| 2006/0263434 A1 | 11/2006 | Desai et al. |
| 2007/0082838 A1* | 4/2007 | De et al. ..................... 514/2 |
| 2007/0087022 A1 | 4/2007 | Desai et al. |
| 2007/0093547 A1 | 4/2007 | Desai et al. |
| 2007/0116774 A1 | 5/2007 | Desai et al. |
| 2007/0117744 A1 | 5/2007 | Desai et al. |
| 2007/0129448 A1 | 6/2007 | Desai et al. |
| 2007/0166388 A1 | 7/2007 | Desai et al. |
| 2008/0063724 A1 | 3/2008 | Desai et al. |
| 2008/0153738 A1 | 6/2008 | Desai et al. |
| 2008/0161382 A1 | 7/2008 | Desai et al. |
| 2008/0213370 A1 | 9/2008 | Desai et al. |
| 2008/0269224 A1 | 10/2008 | Pearson et al. |
| 2008/0280987 A1 | 11/2008 | Desai et al. |
| 2009/0098210 A1 | 4/2009 | Desai et al. |
| 2009/0196933 A1 | 8/2009 | De et al. |
| 2009/0263483 A1 | 10/2009 | Desai et al. |
| 2009/0304805 A1 | 12/2009 | Desai et al. |
| 2010/0035800 A1 | 2/2010 | Desai et al. |
| 2010/0048499 A1 | 2/2010 | Desai et al. |
| 2010/0112077 A1 | 5/2010 | Desai et al. |
| 2010/0166869 A1 | 7/2010 | Desai et al. |
| 2010/0183728 A1 | 7/2010 | Desai et al. |
| 2010/0196490 A1 | 8/2010 | Desai et al. |
| 2010/0215751 A1 | 8/2010 | Desai et al. |
| 2010/0226996 A1 | 9/2010 | Desai et al. |
| 2010/0297243 A1 | 11/2010 | Desai et al. |
| 2011/0052708 A1 | 3/2011 | Soon-Shiong et al. |
| 2011/0118342 A1 | 5/2011 | De et al. |
| 2011/0151012 A1 | 6/2011 | Desai et al. |
| 2012/0070502 A1 | 3/2012 | Desai et al. |
| 2012/0076862 A1 | 3/2012 | Desai et al. |
| 2012/0128732 A1 | 5/2012 | Trieu et al. |
| 2012/0189701 A1 | 7/2012 | Desai et al. |
| 2012/0231082 A1 | 9/2012 | Desai et al. |
| 2012/0283205 A1 | 11/2012 | Desai et al. |
| 2012/0308612 A1 | 12/2012 | De et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017316 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0134257 A1 | 5/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199403 A1 | 7/2014 | Desai et al. |
| 2014/0199404 A1 | 7/2014 | Heise et al. |
| 2014/0199405 A1 | 7/2014 | Pierce et al. |
| 2014/0271871 A1 | 9/2014 | Desai et al. |
| 2014/0296279 A1 | 10/2014 | Seward et al. |
| 2014/0296353 A1 | 10/2014 | Desai et al. |
| 2014/0302157 A1 | 10/2014 | Desai et al. |
| 2015/0050356 A1 | 2/2015 | Desai et al. |
| 2015/0079177 A1 | 3/2015 | Desai et al. |
| 2015/0079181 A1 | 3/2015 | Desai et al. |
| 2015/0104521 A1 | 4/2015 | Desai et al. |
| 2015/0111960 A1 | 4/2015 | Desai et al. |
| 2015/0157722 A1 | 6/2015 | Foss et al. |
| 2015/0165047 A1 | 6/2015 | Desai et al. |
| 2015/0190519 A1 | 7/2015 | Desai et al. |

FOREIGN PATENT DOCUMENTS

| | | |
|---|---|---|
| CN | 101023066 A | 8/2007 |
| CN | 101291658 A | 10/2008 |
| JP | 2002-539081 A | 11/2002 |
| JP | 2008-508245 A | 3/2008 |
| JP | 2008-516260 A | 5/2008 |
| JP | 2009-506126 A | 2/2009 |
| WO | WO-94/18954 A1 | 9/1994 |
| WO | WO-97/10887 A1 | 3/1997 |
| WO | WO-98/14174 A1 | 4/1998 |
| WO | WO-98/14175 A1 | 4/1998 |
| WO | WO-99/00113 A1 | 1/1999 |
| WO | WO-00/40966 A1 | 7/2000 |
| WO | WO-00/43782 A2 | 7/2000 |
| WO | WO-00/43782 A3 | 7/2000 |
| WO | WO-00/66437 A1 | 11/2000 |
| WO | WO-00/71079 A2 | 11/2000 |
| WO | WO-00/71079 A3 | 11/2000 |
| WO | WO-01/89522 A1 | 11/2001 |

(56) References Cited

FOREIGN PATENT DOCUMENTS

| | | |
|---|---|---|
| WO | WO-02/087545 A1 | 11/2002 |
| WO | WO-03/096944 A1 | 11/2003 |
| WO | WO-2004/050851 A2 | 6/2004 |
| WO | WO-2004/050851 A3 | 6/2004 |
| WO | WO-2004/052401 A2 | 6/2004 |
| WO | WO-2004/052401 A3 | 6/2004 |
| WO | WO-2004/090102 A2 | 10/2004 |
| WO | WO-2004/090102 A3 | 10/2004 |
| WO | WO-2006/010915 A1 | 2/2006 |
| WO | WO 2006010915 A1 * | 2/2006 |
| WO | WO-2006/044459 A2 | 4/2006 |
| WO | WO-2006/044459 A3 | 4/2006 |
| WO | WO-2006/089290 A1 | 8/2006 |
| WO | WO-2007/027819 A2 | 3/2007 |
| WO | WO-2007/027819 A3 | 3/2007 |
| WO | WO-2007/027941 A2 | 3/2007 |
| WO | WO-2007/027941 A3 | 3/2007 |
| WO | WO-2008/027055 A1 | 3/2008 |
| WO | WO-2008/057562 A1 | 5/2008 |
| WO | WO-2008/076373 A1 | 6/2008 |
| WO | WO-2008/109163 A1 | 9/2008 |
| WO | WO-2008/137148 A2 | 11/2008 |
| WO | WO-2008/137148 A3 | 11/2008 |
| WO | WO-2008/150532 A1 | 12/2008 |
| WO | WO-2009/126175 A1 | 10/2009 |
| WO | WO-2009/126401 A1 | 10/2009 |
| WO | WO-2009/126938 A1 | 10/2009 |
| WO | WO-2010/068925 A1 | 6/2010 |
| WO | WO-2010/105172 A1 | 9/2010 |
| WO | WO-2010/118365 A1 | 10/2010 |
| WO | WO-2010/121000 A1 | 10/2010 |
| WO | WO-2011/025838 A1 | 3/2011 |

OTHER PUBLICATIONS

Aguzzi, A. et al. (Jul. 2007). "Insights Into Prion Strains and Neurotoxicity," *Nat. Rev. Mol. Cell Biol.* 8(7):552-561.
Anonymous. (Jan. 19, 2007). "Fourth Case of Transfusion-Associated Varian—CJD Infection," *Health Protection Report issued by Health Protection Agency*, available at <http://www.hpa.org.uk/hpr/archives/2007/news2007/news0307.htm>, last visited Nov. 2, 2010, vol. 1, No. 3, 3 pages.
Anonymous. (Oct. 21, 2004). "Committee for Medicinal Products for Human Use (CHMP): Guideline on the Investigation of Manufacturing Processes for Plasma-Derived Medicinal Products with Regard to vCJD Risk," *European Medicines Agency*, available at <http://www.emea.europa.eu/pdfs/human/bwp/513603en.pdf>, last visited on Nov. 2, 2010, 10 pages total.
Barletta, J. M. et al. (2005). "Detection of Ultra-Low Levels of Pathologic Prion Protein in Scrapie Infected Hamster Brain Homogenates Using Real-Time Immuno-PCR," *Journal of Virology Methods* 127:154-164.
Brown, P. et al. (Sep. 1998). "The Distribution of Infectivity in Blood Components and Plasma Derivatives in Experimental Models of Transmissible Spongiform Encephalopathy," *Transfusion* 38(9):810-816.
Brown, P. (2006). "Blood Infectivity in the Transmissible Spongiform Encephalopathies," Chapter 4 in *Creutzfeldt-Jakob Disease: Managing the Risk of Transmission by Blood, Plasma, and Tissues*, Turner, M.L. ed., AABB Press, Bethesda, Maryland, pp. 95-118.
Caughey, B. et al. (Apr. 1994). "Binding of the Protease-Sensitive Form of Prion Protein PrP to Sulfated Glycosaminoglycan and Congo Red," *J. Virology* 68(4):2135-2141.
Diringer, H. et al. (1984). "Sustained Viremia in Experimental Hamster Scrapie," *Archives of Virology* 82(1-2):105-109.
Fischer, M. B. et al. (Nov. 23, 2000). "Binding of Disease-Associated Prion Protein to: Plasminogen," *Nature* 408:479-483.
Ingrosso, L. et al. (Jan. 1995). "Congo Red Prolongs the Incubation Period in Scrapie-Infected Hamsters," *Journal of Virology* 69(1):506-508.
Kascsak, R. J. et al. (1997). "Immunodiagnosis of Prion Disease," *Immunological Investigations* 26(1 &2):259-268.

Llewelyn, C. A. et al. (Feb. 7, 2004). "Possible Transmission of Variant Creutzfeldt-Jakob Disease by Blood Transfusion," *Lancet* 363(9407):417-421.
Manuelidis, E. E. et al. (Feb. 23, 1978). "Transmission of Creutzfeldt-Jakob Disease with Scrapie-Like Syndromes to Mice," *Nature* 271(5647):778-779.
Peden, A. H. et al. (Aug. 7-13, 2004). "Preclinical vCJD After Blood Transfusion in a PRNP Codon 129 Heterozygous Patient," *Lancet* 364(9433):527-529.
Priola, S. A. et al. (Feb. 18, 2000). "Porphyrin and Phthalocyanine Antiscrapie Compounds," *Science* 287(5456):1503-1506.
Prusiner, S. B. (Nov. 1998). "Prions," *Proc. Natl. Acad. Sci. USA* 95:13363-13383.
Seitz, R. et al. (2007). "Impact of vCJD on Blood Supply," *Biologicals* 35:79-97.
Soto, C. et al. (Jan. 15, 2000). "Reversion of Prion Protein Conformational Changes by Synthetic β-Sheet Breaker Peptides," *The Lancet* 355(9199):192-197.
Stöckel, J. et al. (1998). "Prion Protein Selectively Binds Copper(II) Ions," *Biochemistry* 37(20):7185-7193.
Tagliavini, F. et al. (May 16, 1997). "Effectiveness of Anthracycline Against Experimental Prion Diseases in Syrian Hamsters," *Science* 276(5315):1119-1122.
Will, R. G. et al. (Apr. 6, 1996). "A New Variant of Creutzfeldt-Jakob Disease in the UK," *Lancet* 347(9006):921-925.
Wroe, S. J. et al. (Dec. 9-15, 2006). "Clinical Presentation and Pre-Mortem Diagnosis of Variant Creutzfeldt-Jakob Disease Associated with Blood Transfusion: A Case Report," *Lancet* 368(9552):2061-2067.
International Search Report mailed on Jun. 2, 2010, for PCT Patent Application No. PCT/US2010/031197 filed on Apr. 15, 2010, published as WO 2010/12100 on Oct. 21, 2010, 5 pages.
Written Opinion mailed on Jun. 2, 2010, for PCT Patent Application No. PCT/US2010/031197 filed on Apr. 15, 2010, published as WO 2010/12100 on Oct. 21, 2010, 6 pages.
Final Office Action mailed on Feb. 7, 2013, for U.S. Appl. No. 12/761,292, filed Apr. 15, 2010, 10 pages.
Non Final Office Action mailed on Aug. 24, 2012, for U.S. Appl. No. 12/761,292, filed Apr. 15, 2010, 9 pages.
Non Final Office Action mailed on Aug. 27, 2013, for U.S. Appl. No. 12/761,292, filed Apr. 15, 2010, 11 pages.
U.S. Appl. No. 09/446,783, filed May 16, 2000, for Desai et al.
U.S. Appl. No. 09/937,840, filed Jan. 28, 2002, for Desai et al.
U.S. Appl. No. 12/479,710, filed Jun. 5, 2009 for Desai et al.
U.S. Appl. No. 12/818,099, filed Jun. 17, 2010 for De et al.
U.S. Appl. No. 12/824,014, filed Jun. 25, 2010 for Desai et al.
U.S. Appl. No. 12/874,965, filed Sep. 2, 2010, for De et al.
U.S. Appl. No. 12/832,876, filed Jul. 8, 2010, for Desai et al.
U.S. Appl. No. 12/910,693, filed Oct. 22, 1010, for Desai et al.
U.S. Appl. No. 13/038,287, filed on Mar. 1, 2011, for Desai et al.
U.S. Appl. No. 13/263,723, internationally filed on Apr. 9, 2010, for Desai et al.
U.S. Appl. No. 13/564,633, filed Aug. 1, 2012, for Desai et al.
U.S. Appl. No. 13/583,603, filed Mar. 25, 2011, for Yeo et al.
U.S. Appl. No. 13/585,696, filed Aug. 14, 2012, for Desai et al.
U.S. Appl. No. 13/649,987, filed Oct. 11, 2012, for Desai et al.
U.S. Appl. No. 13/701,001, internationally filed on May 20, 2011, for Desai et al.
U.S. Appl. No. 13/701,002, internationally filed on May 20, 2011, for Desai et al.
U.S. Appl. No. 13/701,003, internationally filed on May 20, 2011, for Desai et al.
U.S. Appl. No. 13/743,212, filed Jan. 16, 2013, for for Desai et al.
U.S. Appl. No. 13/776,481, filed Feb. 25, 2013, for Desai et al.
U.S. Appl. No. 13/776,484, filed Feb. 25, 2013, for Desai et al.
U.S. Appl. No. 13/777,980, filed Feb. 26, 2013, for Desai et al.
U.S. Appl. No. 13/777,988, filed Feb. 26, 2013, for Desai et al.
U.S. Appl. No. 13/779,625, filed Feb. 27, 2013, for Desai et al.
U.S. Appl. No. 13/779,624, filed Feb. 27, 2013, for Desai et al.
U.S. Appl. No. 13/779,621, filed Feb. 27, 2013, for Desai et al.
U.S. Appl. No. 13/781,482, filed Feb. 28, 2013 for Desai et al.
U.S. Appl. No. 13/781,479, filed Feb. 28, 2013, for Desai et al.
U.S. Appl. No. 13/781,489, filed Feb. 28, 2013, for Trieu et al.

(56) References Cited

OTHER PUBLICATIONS

U.S. Appl. No. 13/781,480, filed Feb. 28, 2013, for Yeo et al.
U.S. Appl. No. 13/782,984, filed Mar. 1, 2013, for Desai et al.
U.S. Appl. No. 13/782,988, filed Mar. 1, 2013, for Desai et al.
U.S. Appl. No. 13/782,990, filed Mar. 1, 2013, for Desai et al.
U.S. Appl. No. 13/782,992, filed Mar. 1, 2013, for Desai et al.
U.S. Appl. No. 13/783,122, filed Mar. 1, 2013, for Desai et al.
U.S. Appl. No. 13/791,841, filed Mar. 12, 2013, for Desai et al.
U.S. Appl. No. 13/794,480, filed Mar. 12, 2013, for Desai et al.
U.S. Appl. No. 13/794,486, filed Mar. 12, 2013, for Heise et al.
U.S. Appl. No. 13/794,705, filed Mar. 12, 2013, for Desai et al.
U.S. Appl. No. 13/794,712, filed Mar. 11, 2013, for Pierce et al.
U.S. Appl. No. 14/714,131, filed May 15, 2015, by Seward et al.
U.S. Appl. No. 14/834,331, filed Aug. 24, 2015, by Desai et al.
U.S. Appl. No. 14/835,485, filed Aug. 25, 2015, by Desai et al.
U.S. Appl. No. 14/771,783, internationally filed Mar. 10, 2014, by Benettaib et al.
U.S. Appl. No. 14/772,335, internationally filed on Mar. 10, 2014, by Desai et al.
U.S. Appl. No. 14/772,725, internationally filed on Mar. 13, 2014, for Desai et al.
Gregori, L. et al. (Dec. 23, 2006). "Reduction in Infectivity of Endogenous Transmissible Spongiform Encephalopathies Present in Blood by Adsorption to Selective Affinity Resins," *Lancet* 368(9554):2226-2230.

\* cited by examiner

Figure 3
20% Alb/0.01% SBH
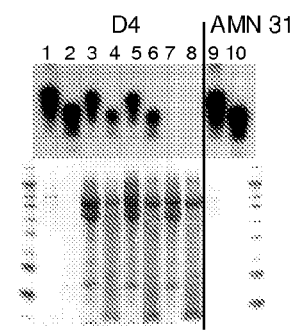
20% Alb/0.005% SBH
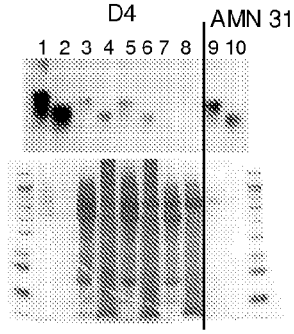
Loading Pattern:
1. 0.1% SBH (buffer) −PK
2. 0.1% SBH (buffer) +PK
3. D4 Column #1 −PK
4. D4 Column #1 +PK
5. D4 Column #2 −PK
6. D4 Column #2 +PK
7. D4 Column #3 −PK
8. D4 Column #3 +PK
9. AMN 31 Column #1 −PK
10. AMN 31 column #1 +PK
25% Alb/0.01% SBH
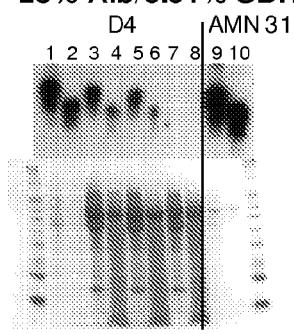
25% Alb/0.005% SBH
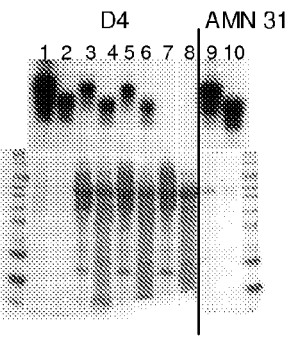

TSE Removal by the Prion Reduction Resin Column (PRDT Column) for 20% Albumin

TSE Removal by the Prion Reduction Resin Column (PRDT Column) for 25% Albumin

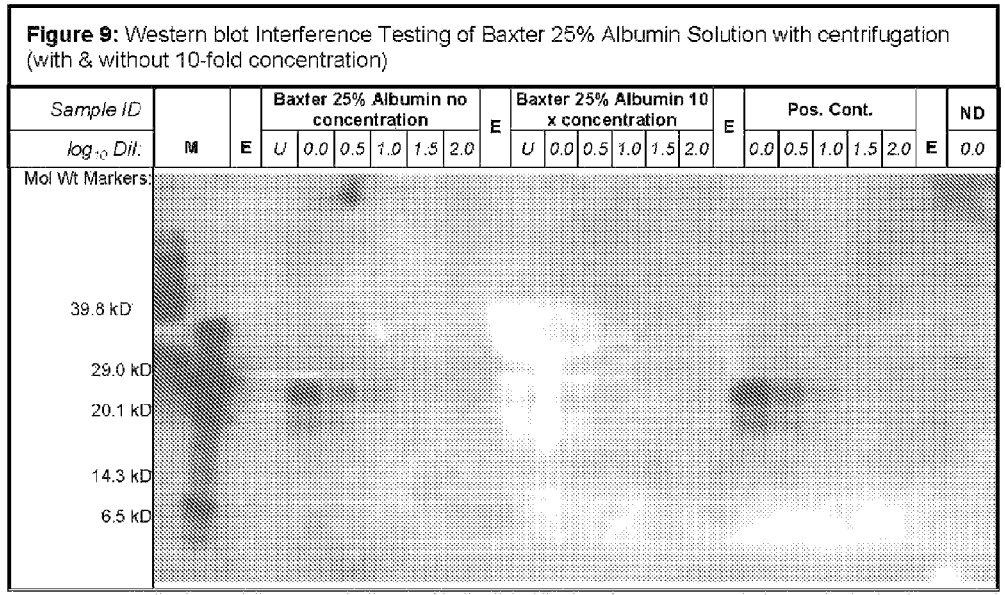

SEQUENCE LISTING

<160> NUMBER OF SEQ ID NOS: 246

<210> SEQ ID NO 1
<211> LENGTH: 7
<212> TYPE: PRT

<213> ORGANISM: Artificial Sequence
<220> FEATURE:
<223> OTHER INFORMATION: Synthetic Construct

<400> SEQUENCE: 1

Lys Ile His Lys Phe Leu Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Gly Thr His Asp Phe Gln Ala
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Lys Phe Gly Ser Thr His Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Construct

<400> SEQUENCE: 4

Phe Val Asn Glu Ile Glu Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Gly Leu His Phe Lys Ser Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Gly Arg Val Leu His His Ala
1               5

<210> SEQ ID NO 7
<211> LENGTH: 7
<212> TYPE: PRT
<213> ORGANISM: Artificial Sequence

```
<220> FEATURE:
<223> OTHER INFORMATION: Synthetic Construct

<400> SEQUENCE: 7

Gln Lys Asn Ser Glu Trp Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

His Ala Tyr Phe Thr His Ala
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Trp Pro Lys Gly Ala Val Ala
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Arg Pro Trp Lys Lys Ala Ala
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Pro Lys His Ile Trp Pro Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

His Lys Leu Trp Gly Val Ala
1               5

<210> SEQ ID NO 13
<211> LENGTH: 7
<212> TYPE: PRT
<213> ORGANISM: Artificial Sequence
<220> FEATURE:
```

```
<223> OTHER INFORMATION: Synthetic Construct

<400> SEQUENCE: 13

Gly Gly Tyr Lys Pro Tyr Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Glu Asn Val Ser Gln Asn Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

His Thr Tyr Tyr Asn Gly Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct

<400> SEQUENCE: 16

Lys Lys Lys Ser Asp His Ala
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

His His Leu Lys Gly Thr Ala
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Lys Lys His Gly Val Trp Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 19

Asp Gly Thr Gln Ala His Ala
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

Ala Pro His Arg Asn Asn Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

His His Gly His Asn Ile Ala
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

His Thr Trp His Gly Gln Ala
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

His Val Phe Val Thr Trp Ala
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Thr His His Phe Tyr Ile Ala
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: VARIANT
<222> LOCATION: 6
<223> OTHER INFORMATION: Xaa = Ala or Gly

<400> SEQUENCE: 25

Lys Leu Gly Trp Gly Xaa Ala
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Construct

<400> SEQUENCE: 26

Gly Ser Lys Lys Lys Glu Ala
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Pro Leu Leu Val Val Trp Ala
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Trp Leu Leu Val Gly Gly Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Trp or Gly

<400> SEQUENCE: 29

Xaa Gln Val Leu Val Tyr Ala
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Arg Arg His Gln Arg Gln Ala
1               5
```

```
<210> SEQ ID NO 31
<211> LENGTH: 7
<212> TYPE: PRT
<213> ORGANISM: Artificial Sequence
<220> FEATURE:
<223> OTHER INFORMATION: Synthetic Construct

<400> SEQUENCE: 31

Leu Pro Trp Thr Phe Gly Ala
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Ile Phe Ile Ile Ile Thr Ala
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Unknown

<400> SEQUENCE: 33

Pro Xaa Ile Glu Pro His Ala
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Glu Trp Gly Ile Ile Trp Ala
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct

<400> SEQUENCE: 35

Gly Trp Tyr Ile Tyr Phe Ala
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Thr Leu Ile Leu Phe His Ala
```

1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Phe Leu Leu Ser Asn His Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct

<400> SEQUENCE: 38

Trp Gln Ile Arg Phe Phe Ala
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

Val Leu Leu Val Phe Glu Ala
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

Gly Trp Val Leu Glu Ile Ala
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

Phe Leu Leu Ile Asp Thr Ala
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Construct

<400> SEQUENCE: 42

Gly Phe Leu Phe Lys Phe Ala
1               5

```
<210> SEQ ID NO 43
<211> LENGTH: 7
<212> TYPE: PRT
<213> ORGANISM: Artificial Sequence
<220> FEATURE:
<223> OTHER INFORMATION: Synthetic Construct

<400> SEQUENCE: 43

Pro Trp Thr Ile Tyr Ile Ala
1               5

<210> SEQ ID NO 44
<211> LENGTH: 2
<212> TYPE: PRT
<213> ORGANISM: Artificial Sequence
<220> FEATURE:
<223> OTHER INFORMATION: Synthetic Construct

<400> SEQUENCE: 44

Trp His
1

<210> SEQ ID NO 45
<211> LENGTH: 2
<212> TYPE: PRT
<213> ORGANISM: Artificial Sequence
<220> FEATURE:
<223> OTHER INFORMATION: Synthetic Construct

<400> SEQUENCE: 45

Trp Trp
1

<210> SEQ ID NO 46
<211> LENGTH: 2
<212> TYPE: PRT
<213> ORGANISM: Artificial Sequence
<220> FEATURE:
<223> OTHER INFORMATION: Synthetic Construct

<400> SEQUENCE: 46

Leu Trp
1

<210> SEQ ID NO 47
<211> LENGTH: 3
<212> TYPE: PRT
<213> ORGANISM: Artificial Sequence
<220> FEATURE:
<223> OTHER INFORMATION: Synthetic Construct

<400> SEQUENCE: 47

Trp Asn Ala
1

<210> SEQ ID NO 48
<211> LENGTH: 3
<212> TYPE: PRT
<213> ORGANISM: Artificial Sequence
<220> FEATURE:
<223> OTHER INFORMATION: Synthetic Construct

<400> SEQUENCE: 48

Glu Phe Trp
1
```

<210> SEQ ID NO 49
<211> LENGTH: 3
<212> TYPE: PRT
<213> ORGANISM: Artificial Sequence
<220> FEATURE:
<223> OTHER INFORMATION: Synthetic Construct

<400> SEQUENCE: 49

Leu Pro Trp
1

<210> SEQ ID NO 50
<211> LENGTH: 3
<212> TYPE: PRT
<213> ORGANISM: Artificial Sequence
<220> FEATURE:
<223> OTHER INFORMATION: Synthetic Construct

<400> SEQUENCE: 50

Tyr Glu Tyr
1

<210> SEQ ID NO 51
<211> LENGTH: 3
<212> TYPE: PRT
<213> ORGANISM: Artificial Sequence
<220> FEATURE:
<223> OTHER INFORMATION: Synthetic Construct

<400> SEQUENCE: 51

Trp Pro Ala
1

<210> SEQ ID NO 52
<211> LENGTH: 3
<212> TYPE: PRT
<213> ORGANISM: Artificial Sequence
<220> FEATURE:
<223> OTHER INFORMATION: Synthetic Construct

<400> SEQUENCE: 52

Phe Asn Gln
1

<210> SEQ ID NO 53
<211> LENGTH: 3
<212> TYPE: PRT
<213> ORGANISM: Artificial Sequence
<220> FEATURE:
<223> OTHER INFORMATION: Synthetic Construct

<400> SEQUENCE: 53

Tyr His Glu
1

<210> SEQ ID NO 54
<211> LENGTH: 3
<212> TYPE: PRT
<213> ORGANISM: Artificial Sequence
<220> FEATURE:
<223> OTHER INFORMATION: Synthetic Construct

<400> SEQUENCE: 54

Leu Phe Ala
1

```
<210> SEQ ID NO 55
<211> LENGTH: 3
<212> TYPE: PRT
<213> ORGANISM: Artificial Sequence
<220> FEATURE:
<223> OTHER INFORMATION: Synthetic Construct

<400> SEQUENCE: 55

Asn His Tyr
1

<210> SEQ ID NO 56
<211> LENGTH: 3
<212> TYPE: PRT
<213> ORGANISM: Artificial Sequence
<220> FEATURE:
<223> OTHER INFORMATION: Synthetic Construct

<400> SEQUENCE: 56

Thr Leu Gly
1

<210> SEQ ID NO 57
<211> LENGTH: 3
<212> TYPE: PRT
<213> ORGANISM: Artificial Sequence
<220> FEATURE:
<223> OTHER INFORMATION: Synthetic Construct

<400> SEQUENCE: 57

Trp Val Asp
1

<210> SEQ ID NO 58
<211> LENGTH: 5
<212> TYPE: PRT
<213> ORGANISM: Artificial Sequence
<220> FEATURE:
<223> OTHER INFORMATION: Synthetic Construct

<400> SEQUENCE: 58

Tyr Trp Asp Gln Ala
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic Construct

<400> SEQUENCE: 59

Tyr Val His Glu Ala
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Construct

<400> SEQUENCE: 60

Trp Phe Asp Glu Ala
1               5

<210> SEQ ID NO 61
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 61

Leu Gln Trp Tyr Asp Ala
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic Construct

<400> SEQUENCE: 62

Tyr Thr His Ser Glu Ala
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic Construct

<400> SEQUENCE: 63

Trp Ile Asp Tyr Glu Ala
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic Construct

<400> SEQUENCE: 64

Val Trp Ile Asp Ala Ala
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Trp Asp Glu Ala Glu Glu Ala
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic Construct

<400> SEQUENCE: 66

Tyr Asp Ser Tyr Asp Asp Ala
1               5

<210> SEQ ID NO 67
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 67

Asn Asp Phe Ile Asp Phe Ala
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic Construct

<400> SEQUENCE: 68

Tyr Glu Pro Trp Gly Ser Ala
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic Construct

<400> SEQUENCE: 69

Glu Tyr Gly Asp Trp Trp Ala
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct

<400> SEQUENCE: 70

Trp Asp Tyr Asp Gln Glu Ala
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic Construct

<400> SEQUENCE: 71

Asp Trp Gly Asp Pro Phe Ala
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic Construct

<400> SEQUENCE: 72

Asp Trp Pro Glu Val Trp Ala
1               5

<210> SEQ ID NO 73
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 73

Phe His Asp Phe Ser Glu Ala
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic Construct

<400> SEQUENCE: 74

Asp Thr Phe Trp Asp Tyr Ala
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic Construct

<400> SEQUENCE: 75

Trp Asn Asp Leu Asp Asn Ala
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Construct

<400> SEQUENCE: 76

Ala Ser Ala Leu Val Tyr Ala
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic Construct

<400> SEQUENCE: 77

Leu Ile Asn Ala Gly Gly Ala
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic Construct

<400> SEQUENCE: 78

Trp Glu Ser Tyr Val Thr Ala
1               5

<210> SEQ ID NO 79
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 79

Trp Ser Asp Glu Gly Tyr Ala
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic Construct

<400> SEQUENCE: 80

Tyr Arg Trp Thr Gly Pro Ala
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic Construct

<400> SEQUENCE: 81

Tyr Glu Asp Gln Trp Gln Ala
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic Construct

<400> SEQUENCE: 82

Glu Trp Ala Asp Asp Asn Ala
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic Construct

<400> SEQUENCE: 83

Tyr Glu Ile Asp Tyr Gly Ala
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic Construct

<400> SEQUENCE: 84

Glu Phe Gly Tyr Phe Asp Ala
1               5

<210> SEQ ID NO 85
<211> LENGTH: 7
<212> TYPE: PRT
<213> ORGANISM: Artificial Sequence
<220> FEATURE:
```

```
<223> OTHER INFORMATION: Synthetic Construct

<400> SEQUENCE: 85

Trp Gly Asp Glu Gln Asp Ala
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic Construct

<400> SEQUENCE: 86

His Glu Glu Asp Trp Ala Ala
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic Construct

<400> SEQUENCE: 87

Phe Glu Asp Phe Glu Leu Ala
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic Construct

<400> SEQUENCE: 88

Thr Trp Gly Ile Asp Glu Ala
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic Construct

<400> SEQUENCE: 89

Trp Asp Pro Thr Asp Tyr Ala
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic Construct

<400> SEQUENCE: 90

Asn Asp Lys Ile His Thr Ala
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic Construct
```

-continued

<400> SEQUENCE: 91

Phe Glu Asp Phe Phe Ser Ala
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic Construct

<400> SEQUENCE: 92

Tyr Glu Trp Ala Glu Gln Ala
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic Construct

<400> SEQUENCE: 93

Thr His Val Tyr Phe Leu Ala
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ser, Thr, or Trp
<220> FEATURE:
<221> NAME/KEY: VARIANT
<222> LOCATION: 2
<223> OTHER INFORMATION: Xaa = Unknown

<400> SEQUENCE: 94

Xaa Xaa Asp Phe Ser Asp Ala
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic Construct

<400> SEQUENCE: 95

Tyr Arg Thr Pro Asn Glu Ala
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gly or Leu

<400> SEQUENCE: 96

```
Xaa Arg Ser Glu Thr Ala
1               5

<210> SEQ ID NO 97
<211> LENGTH: 3
<212> TYPE: PRT
<213> ORGANISM: Artificial Sequence
<220> FEATURE:
<223> OTHER INFORMATION: Synthetic Construct

<400> SEQUENCE: 97

Ile His Asn
1

<210> SEQ ID NO 98
<211> LENGTH: 3
<212> TYPE: PRT
<213> ORGANISM: Artificial Sequence
<220> FEATURE:
<223> OTHER INFORMATION: Synthetic Construct

<400> SEQUENCE: 98

Trp Glu Tyr
1

<210> SEQ ID NO 99
<211> LENGTH: 3
<212> TYPE: PRT
<213> ORGANISM: Artificial Sequence
<220> FEATURE:
<223> OTHER INFORMATION: Synthetic Construct

<400> SEQUENCE: 99

Asp Tyr Trp
1

<210> SEQ ID NO 100
<211> LENGTH: 3
<212> TYPE: PRT
<213> ORGANISM: Artificial Sequence
<220> FEATURE:
<223> OTHER INFORMATION: Synthetic Construct

<400> SEQUENCE: 100

Trp Asp Trp
1

<210> SEQ ID NO 101
<211> LENGTH: 3
<212> TYPE: PRT
<213> ORGANISM: Artificial Sequence
<220> FEATURE:
<223> OTHER INFORMATION: Synthetic Construct

<400> SEQUENCE: 101

Trp Gln Asp
1

<210> SEQ ID NO 102
<211> LENGTH: 3
<212> TYPE: PRT
<213> ORGANISM: Artificial Sequence
<220> FEATURE:
<223> OTHER INFORMATION: Synthetic Construct

<400> SEQUENCE: 102
```

Tyr Phe Glu
1

<210> SEQ ID NO 103
<211> LENGTH: 3
<212> TYPE: PRT
<213> ORGANISM: Artificial Sequence
<220> FEATURE:
<223> OTHER INFORMATION: Synthetic Construct

<400> SEQUENCE: 103

Asn Tyr Glu
1

<210> SEQ ID NO 104
<211> LENGTH: 3
<212> TYPE: PRT
<213> ORGANISM: Artificial Sequence
<220> FEATURE:
<223> OTHER INFORMATION: Synthetic Construct

<400> SEQUENCE: 104

Ser Tyr Ala
1

<210> SEQ ID NO 105
<211> LENGTH: 3
<212> TYPE: PRT
<213> ORGANISM: Artificial Sequence
<220> FEATURE:
<223> OTHER INFORMATION: Synthetic Construct

<400> SEQUENCE: 105

Trp Asp Leu
1

<210> SEQ ID NO 106
<211> LENGTH: 3
<212> TYPE: PRT
<213> ORGANISM: Artificial Sequence
<220> FEATURE:
<223> OTHER INFORMATION: Synthetic Construct

<400> SEQUENCE: 106

Trp Leu Glu
1

<210> SEQ ID NO 107
<211> LENGTH: 3
<212> TYPE: PRT
<213> ORGANISM: Artificial Sequence
<220> FEATURE:
<223> OTHER INFORMATION: Synthetic Construct

<400> SEQUENCE: 107

Val Gln Arg
1

<210> SEQ ID NO 108
<211> LENGTH: 3
<212> TYPE: PRT
<213> ORGANISM: Artificial Sequence
<220> FEATURE:
<223> OTHER INFORMATION: Synthetic Construct

<400> SEQUENCE: 108

Tyr Ile Asp

<210> SEQ ID NO 109
<211> LENGTH: 3
<212> TYPE: PRT
<213> ORGANISM: Artificial Sequence
<220> FEATURE:
<223> OTHER INFORMATION: Synthetic Construct

<400> SEQUENCE: 109

Arg Trp Asp
1

<210> SEQ ID NO 110
<211> LENGTH: 3
<212> TYPE: PRT
<213> ORGANISM: Artificial Sequence
<220> FEATURE:
<223> OTHER INFORMATION: Synthetic Construct

<400> SEQUENCE: 110

Asp Val Arg
1

<210> SEQ ID NO 111
<211> LENGTH: 3
<212> TYPE: PRT
<213> ORGANISM: Artificial Sequence
<220> FEATURE:
<223> OTHER INFORMATION: Synthetic Construct

<400> SEQUENCE: 111

Trp Ser Asp
1

<210> SEQ ID NO 112
<211> LENGTH: 3
<212> TYPE: PRT
<213> ORGANISM: Artificial Sequence
<220> FEATURE:
<223> OTHER INFORMATION: Synthetic Construct

<400> SEQUENCE: 112

His Trp Asp
1

<210> SEQ ID NO 113
<211> LENGTH: 3
<212> TYPE: PRT
<213> ORGANISM: Artificial Sequence
<220> FEATURE:
<223> OTHER INFORMATION: Synthetic Construct

<400> SEQUENCE: 113

Trp Gln Asp
1

<210> SEQ ID NO 114
<211> LENGTH: 3
<212> TYPE: PRT
<213> ORGANISM: Artificial Sequence
<220> FEATURE:
<223> OTHER INFORMATION: Synthetic Construct

<400> SEQUENCE: 114

Trp Asp Asp
1

```
<210> SEQ ID NO 115
<211> LENGTH: 3
<212> TYPE: PRT
<213> ORGANISM: Artificial Sequence
<220> FEATURE:
<223> OTHER INFORMATION: Synthetic Construct

<400> SEQUENCE: 115

Trp Glu Asp
1

<210> SEQ ID NO 116
<211> LENGTH: 3
<212> TYPE: PRT
<213> ORGANISM: Artificial Sequence
<220> FEATURE:
<223> OTHER INFORMATION: Synthetic Construct

<400> SEQUENCE: 116

Ile Thr Asn
1

<210> SEQ ID NO 117
<211> LENGTH: 3
<212> TYPE: PRT
<213> ORGANISM: Artificial Sequence
<220> FEATURE:
<223> OTHER INFORMATION: Synthetic Construct

<400> SEQUENCE: 117

Tyr Glu Asp
1

<210> SEQ ID NO 118
<211> LENGTH: 6
<212> TYPE: PRT
<213> ORGANISM: Artificial Sequence
<220> FEATURE:
<223> OTHER INFORMATION: Synthetic Construct

<400> SEQUENCE: 118

Val Ala Asp Glu Glu Ala
1               5

<210> SEQ ID NO 119
<211> LENGTH: 6
<212> TYPE: PRT
<213> ORGANISM: Artificial Sequence
<220> FEATURE:
<223> OTHER INFORMATION: Synthetic Construct

<400> SEQUENCE: 119

Tyr Tyr Val Asp Ala Ala
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic Construct

<400> SEQUENCE: 120

Gln Asp Phe Asn Leu Ala
1               5
```

<210> SEQ ID NO 121
<211> LENGTH: 6
<212> TYPE: PRT
<213> ORGANISM: Artificial Sequence
<220> FEATURE:
<223> OTHER INFORMATION: Synthetic Construct

<400> SEQUENCE: 121

Asp Asn Pro Ile Asp Ala
1               5

<210> SEQ ID NO 122
<211> LENGTH: 6
<212> TYPE: PRT
<213> ORGANISM: Artificial Sequence
<220> FEATURE:
<223> OTHER INFORMATION: Synthetic Construct

<400> SEQUENCE: 122

Phe Asn Glu His Glu Ala
1               5

<210> SEQ ID NO 123
<211> LENGTH: 6
<212> TYPE: PRT
<213> ORGANISM: Artificial Sequence
<220> FEATURE:
<223> OTHER INFORMATION: Synthetic Construct

<400> SEQUENCE: 123

Trp Gly Ala Asp Gly Ala
1               5

<210> SEQ ID NO 124
<211> LENGTH: 6
<212> TYPE: PRT
<213> ORGANISM: Artificial Sequence
<220> FEATURE:
<223> OTHER INFORMATION: Synthetic Construct

<400> SEQUENCE: 124

Val Ile Tyr Ser His Ala
1               5

<210> SEQ ID NO 125
<211> LENGTH: 6
<212> TYPE: PRT
<213> ORGANISM: Artificial Sequence
<220> FEATURE:
<223> OTHER INFORMATION: Synthetic Construct

<400> SEQUENCE: 125

His Ile Leu Glu Glu Ala
1               5

<210> SEQ ID NO 126
<211> LENGTH: 6
<212> TYPE: PRT
<213> ORGANISM: Artificial Sequence
<220> FEATURE:
<223> OTHER INFORMATION: Synthetic Construct

<400> SEQUENCE: 126

Pro His Glu Asn Phe Ala
1               5

```
<210> SEQ ID NO 127
<211> LENGTH: 6
<212> TYPE: PRT
<213> ORGANISM: Artificial Sequence
<220> FEATURE:
<223> OTHER INFORMATION: Synthetic Construct

<400> SEQUENCE: 127

Glu Asp Asn Gly Gly Ala
1               5

<210> SEQ ID NO 128
<211> LENGTH: 6
<212> TYPE: PRT
<213> ORGANISM: Artificial Sequence
<220> FEATURE:
<223> OTHER INFORMATION: Synthetic Construct

<400> SEQUENCE: 128

Asp Ser Glu Gly Pro Ala
1               5

<210> SEQ ID NO 129
<211> LENGTH: 6
<212> TYPE: PRT
<213> ORGANISM: Artificial Sequence
<220> FEATURE:
<223> OTHER INFORMATION: Synthetic Construct

<400> SEQUENCE: 129

Phe Gln Glu Phe Thr Ala
1               5

<210> SEQ ID NO 130
<211> LENGTH: 6
<212> TYPE: PRT
<213> ORGANISM: Artificial Sequence
<220> FEATURE:
<223> OTHER INFORMATION: Synthetic Construct

<400> SEQUENCE: 130

Glu Gly Asp Glu Ile Ala
1               5

<210> SEQ ID NO 131
<211> LENGTH: 6
<212> TYPE: PRT
<213> ORGANISM: Artificial Sequence
<220> FEATURE:
<223> OTHER INFORMATION: Synthetic Construct

<400> SEQUENCE: 131

Ile Tyr Ala Glu Thr Ala
1               5

<210> SEQ ID NO 132
<211> LENGTH: 6
<212> TYPE: PRT
<213> ORGANISM: Artificial Sequence
<220> FEATURE:
<223> OTHER INFORMATION: Synthetic Construct

<400> SEQUENCE: 132

Arg Val Arg Glu Thr Ala
1               5

<210> SEQ ID NO 133
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 133

Glu Glu Pro Gln Trp Ala
1               5

<210> SEQ ID NO 134
<211> LENGTH: 6
<212> TYPE: PRT
<213> ORGANISM: Artificial Sequence
<220> FEATURE:
<223> OTHER INFORMATION: Synthetic Construct

<400> SEQUENCE: 134

Glu Gly Glu Glu Phe Ala
1               5

<210> SEQ ID NO 135
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Thr or Leu

<400> SEQUENCE: 135

Xaa Phe Asn Ile His Ala
1               5

<210> SEQ ID NO 136
<211> LENGTH: 3
<212> TYPE: PRT
<213> ORGANISM: Artificial Sequence
<220> FEATURE:
<223> OTHER INFORMATION: Synthetic Construct

<400> SEQUENCE: 136

Tyr Asp Trp
1

<210> SEQ ID NO 137
<211> LENGTH: 3
<212> TYPE: PRT
<213> ORGANISM: Artificial Sequence
<220> FEATURE:
<223> OTHER INFORMATION: Synthetic Construct

<400> SEQUENCE: 137

Asn Tyr Thr
1

<210> SEQ ID NO 138
<211> LENGTH: 3
<212> TYPE: PRT
<213> ORGANISM: Artificial Sequence
<220> FEATURE:
<223> OTHER INFORMATION: Synthetic Construct

<400> SEQUENCE: 138

Ser Tyr Thr
1
```

<210> SEQ ID NO 139
<211> LENGTH: 3
<212> TYPE: PRT
<213> ORGANISM: Artificial Sequence
<220> FEATURE:
<223> OTHER INFORMATION: Synthetic Construct

<400> SEQUENCE: 139

Trp Ala Asp
1

<210> SEQ ID NO 140
<211> LENGTH: 3
<212> TYPE: PRT
<213> ORGANISM: Artificial Sequence
<220> FEATURE:
<223> OTHER INFORMATION: Synthetic Construct

<400> SEQUENCE: 140

Gln Trp Gly
1

<210> SEQ ID NO 141
<211> LENGTH: 3
<212> TYPE: PRT
<213> ORGANISM: Artificial Sequence
<220> FEATURE:
<223> OTHER INFORMATION: Synthetic Construct

<400> SEQUENCE: 141

Trp Gly Asp
1

<210> SEQ ID NO 142
<211> LENGTH: 3
<212> TYPE: PRT
<213> ORGANISM: Artificial Sequence
<220> FEATURE:
<223> OTHER INFORMATION: Synthetic Construct

<400> SEQUENCE: 142

Glu Tyr Phe
1

<210> SEQ ID NO 143
<211> LENGTH: 3
<212> TYPE: PRT
<213> ORGANISM: Artificial Sequence
<220> FEATURE:
<223> OTHER INFORMATION: Synthetic Construct

<400> SEQUENCE: 143

Trp Glu His
1

<210> SEQ ID NO 144
<211> LENGTH: 3
<212> TYPE: PRT
<213> ORGANISM: Artificial Sequence
<220> FEATURE:
<223> OTHER INFORMATION: Synthetic Construct

<400> SEQUENCE: 144

Leu Tyr Asp
1

```
<210> SEQ ID NO 145
<211> LENGTH: 3
<212> TYPE: PRT
<213> ORGANISM: Artificial Sequence
<220> FEATURE:
<223> OTHER INFORMATION: Synthetic Construct

<400> SEQUENCE: 145

Asp Tyr Tyr
1

<210> SEQ ID NO 146
<211> LENGTH: 3
<212> TYPE: PRT
<213> ORGANISM: Artificial Sequence
<220> FEATURE:
<223> OTHER INFORMATION: Synthetic Construct

<400> SEQUENCE: 146

Phe Tyr Glu
1

<210> SEQ ID NO 147
<211> LENGTH: 3
<212> TYPE: PRT
<213> ORGANISM: Artificial Sequence
<220> FEATURE:
<223> OTHER INFORMATION: Synthetic Construct

<400> SEQUENCE: 147

Glu Tyr Tyr
1

<210> SEQ ID NO 148
<211> LENGTH: 3
<212> TYPE: PRT
<213> ORGANISM: Artificial Sequence
<220> FEATURE:
<223> OTHER INFORMATION: Synthetic Construct

<400> SEQUENCE: 148

Tyr Asp Tyr
1

<210> SEQ ID NO 149
<211> LENGTH: 3
<212> TYPE: PRT
<213> ORGANISM: Artificial Sequence
<220> FEATURE:
<223> OTHER INFORMATION: Synthetic Construct

<400> SEQUENCE: 149

Trp Asp His
1

<210> SEQ ID NO 150
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = 2-naphthyl-alanine

<400> SEQUENCE: 150
```

Arg Glu Ser Xaa Asn Val Ala
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = 2-naphthyl-alanine

<400> SEQUENCE: 151

Glu Ser Xaa Pro Arg Gln Ala
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic Construct

<400> SEQUENCE: 152

Val Ala Arg Glu Asn Ile Ala
1               5

<210> SEQ ID NO 153
<211> LENGTH: 7
<212> TYPE: PRT
<213> ORGANISM: Artificial Sequence
<220> FEATURE:
<223> OTHER INFORMATION: Synthetic Construct

<400> SEQUENCE: 153

Arg Trp Glu Arg Glu Asp Ala
1               5

<210> SEQ ID NO 154
<211> LENGTH: 6
<212> TYPE: PRT
<213> ORGANISM: Artificial Sequence
<220> FEATURE:
<223> OTHER INFORMATION: Synthetic Construct

<400> SEQUENCE: 154

Glu Trp Trp Glu Thr Val
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic Construct

<400> SEQUENCE: 155

Ser Val Tyr Gln Leu Asp Ala
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic Construct

```
<220> FEATURE:
<221> NAME/KEY: VARIANT
<222> LOCATION: 1
<223> OTHER INFORMATION: Xaa = 2-naphthyl-alanine

<400> SEQUENCE: 156

Xaa His Glu Phe Tyr Gly Ala
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 4
<223> OTHER INFORMATION: Xaa = 2-naphthyl-alanine

<400> SEQUENCE: 157

His Glu Xaa Xaa Leu Val Ala
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 6
<223> OTHER INFORMATION: Xaa = 2-naphthyl-alanine

<400> SEQUENCE: 158

Ala Xaa Val Pro Val Xaa Ala
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic Construct

<400> SEQUENCE: 159

Tyr Phe Asp Tyr Trp Leu Ala
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = 2-naphthyl-alanine

<400> SEQUENCE: 160

Phe Glu Xaa His Arg Gln Ala
1               5

<210> SEQ ID NO 161
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 161

Trp Arg His Glu Pro Ala Ala
1               5

<210> SEQ ID NO 162
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = 2-naphthyl-alanine

<400> SEQUENCE: 162

Ser Ser Xaa Lys Lys Asp Ala
1               5

<210> SEQ ID NO 163
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = 2-naphthyl-alanine

<400> SEQUENCE: 163

Arg Xaa Asp Lys Glu Ala Ala
1               5

<210> SEQ ID NO 164
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = 2-naphthyl-alanine

<400> SEQUENCE: 164

Xaa His Glu Ile Phe Pro Ala
1               5

<210> SEQ ID NO 165
<211> LENGTH: 7
<212> TYPE: PRT
<213> ORGANISM: Artificial Sequence
<220> FEATURE:
<223> OTHER INFORMATION: Synthetic Construct

<400> SEQUENCE: 165

Lys Trp Tyr His His Arg Ala
1               5

<210> SEQ ID NO 166
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 166

His Trp Trp Pro His Asn Ala
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic Construct

<400> SEQUENCE: 167

His Trp Gln Val Phe Tyr Ala
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = 2-naphthyl-alanine

<400> SEQUENCE: 168

Phe His Glu Xaa Glu Ile Ala
1               5

<210> SEQ ID NO 169
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = 2-naphthyl-alanine

<400> SEQUENCE: 169

His Ala Asp Phe Xaa Gln Ala
1               5

<210> SEQ ID NO 170
<211> LENGTH: 7
<212> TYPE: PRT
<213> ORGANISM: Artificial Sequence
<220> FEATURE:
<223> OTHER INFORMATION: Synthetic Construct

<400> SEQUENCE: 170

Ala Leu His Phe Glu Thr Ala
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic Construct

<400> SEQUENCE: 171

Asp Asp Pro Thr Gly Phe Ala
1               5
```

```
<210> SEQ ID NO 172
<211> LENGTH: 7
<212> TYPE: PRT
<213> ORGANISM: Artificial Sequence
<220> FEATURE:
<223> OTHER INFORMATION: Synthetic Construct

<400> SEQUENCE: 172

Val Ala Pro Gly Leu Gly Ala
1               5

<210> SEQ ID NO 173
<211> LENGTH: 7
<212> TYPE: PRT
<213> ORGANISM: Artificial Sequence
<220> FEATURE:
<223> OTHER INFORMATION: Synthetic Construct

<400> SEQUENCE: 173

Ile Phe Arg Leu Ile Glu Ala
1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic Construct

<400> SEQUENCE: 174

Gly Leu Glu Arg Pro Glu Ala
1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic Construct

<400> SEQUENCE: 175

Ile Val Val Arg Leu Trp Ala
1               5

<210> SEQ ID NO 176
<211> LENGTH: 7
<212> TYPE: PRT
<213> ORGANISM: Artificial Sequence
<220> FEATURE:
<223> OTHER INFORMATION: Synthetic Construct

<400> SEQUENCE: 176

Trp His Asn Pro His Tyr Ala
1               5

<210> SEQ ID NO 177
<211> LENGTH: 7
<212> TYPE: PRT
<213> ORGANISM: Artificial Sequence
<220> FEATURE:
<223> OTHER INFORMATION: Synthetic Construct

<400> SEQUENCE: 177

Leu Ile Tyr Lys Ser Asp Ala
1               5
```

```
<210> SEQ ID NO 178
<211> LENGTH: 7
<212> TYPE: PRT
<213> ORGANISM: Artificial Sequence
<220> FEATURE:
<223> OTHER INFORMATION: Synthetic Construct

<400> SEQUENCE: 178

Glu Lys Pro Ile Phe Asn Ala
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic Construct

<400> SEQUENCE: 179

His Trp Ser Glu Pro Ala Ala
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic Construct

<400> SEQUENCE: 180

Gly His Asn Trp Lys Glu Ala
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic Construct

<400> SEQUENCE: 181

Tyr Trp His His Asp Asp Ala
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic Construct

<400> SEQUENCE: 182

Gly Tyr Pro Lys Glu Asn Ala
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic Construct

<400> SEQUENCE: 183

Pro Val Tyr Trp Leu Tyr Ala
1               5

<210> SEQ ID NO 184
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 184

Phe Gly Glu His Thr Pro Ala
1               5

<210> SEQ ID NO 185
<211> LENGTH: 7
<212> TYPE: PRT
<213> ORGANISM: Artificial Sequence
<220> FEATURE:
<223> OTHER INFORMATION: Synthetic Construct

<400> SEQUENCE: 185

Phe Gln Gly Thr Arg Glu Ala
1               5

<210> SEQ ID NO 186
<211> LENGTH: 7
<212> TYPE: PRT
<213> ORGANISM: Artificial Sequence
<220> FEATURE:
<223> OTHER INFORMATION: Synthetic Construct

<400> SEQUENCE: 186

Thr Gly Thr Asn Arg Tyr Ala
1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic Construct

<400> SEQUENCE: 187

Lys Trp Ala Thr Arg Tyr Ala
1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic Construct

<400> SEQUENCE: 188

Asn Ser Thr Lys Phe Asp Ala
1               5

<210> SEQ ID NO 189
<211> LENGTH: 7
<212> TYPE: PRT
<213> ORGANISM: Artificial Sequence
<220> FEATURE:
<223> OTHER INFORMATION: Synthetic Construct

<400> SEQUENCE: 189

Leu Ile Tyr Lys Glu Glu Ala
1               5

<210> SEQ ID NO 190
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 190

Glu His Ala Thr Tyr Arg Ala
1               5

<210> SEQ ID NO 191
<211> LENGTH: 3
<212> TYPE: PRT
<213> ORGANISM: Artificial Sequence
<220> FEATURE:
<223> OTHER INFORMATION: Synthetic Construct

<400> SEQUENCE: 191

His Asn Asp
1

<210> SEQ ID NO 192
<211> LENGTH: 3
<212> TYPE: PRT
<213> ORGANISM: Artificial Sequence
<220> FEATURE:
<223> OTHER INFORMATION: Synthetic Construct

<400> SEQUENCE: 192

His Glu Arg
1

<210> SEQ ID NO 193
<211> LENGTH: 3
<212> TYPE: PRT
<213> ORGANISM: Artificial Sequence
<220> FEATURE:
<223> OTHER INFORMATION: Synthetic Construct

<400> SEQUENCE: 193

His Gly Asp
1

<210> SEQ ID NO 194
<211> LENGTH: 3
<212> TYPE: PRT
<213> ORGANISM: Artificial Sequence
<220> FEATURE:
<223> OTHER INFORMATION: Synthetic Construct

<400> SEQUENCE: 194

His Ser Asp
1

<210> SEQ ID NO 195
<211> LENGTH: 3
<212> TYPE: PRT
<213> ORGANISM: Artificial Sequence
<220> FEATURE:
<223> OTHER INFORMATION: Synthetic Construct

<400> SEQUENCE: 195

His Phe Asp
1

<210> SEQ ID NO 196
<211> LENGTH: 3
<212> TYPE: PRT
```

```
<213> ORGANISM: Artificial Sequence
<220> FEATURE:
<223> OTHER INFORMATION: Synthetic Construct

<400> SEQUENCE: 196

Trp Asn Asp
1

<210> SEQ ID NO 197
<211> LENGTH: 3
<212> TYPE: PRT
<213> ORGANISM: Artificial Sequence
<220> FEATURE:
<223> OTHER INFORMATION: Synthetic Construct

<400> SEQUENCE: 197

Tyr Glu His
1

<210> SEQ ID NO 198
<211> LENGTH: 3
<212> TYPE: PRT
<213> ORGANISM: Artificial Sequence
<220> FEATURE:
<223> OTHER INFORMATION: Synthetic Construct

<400> SEQUENCE: 198

His Trp Asp
1

<210> SEQ ID NO 199
<211> LENGTH: 3
<212> TYPE: PRT
<213> ORGANISM: Artificial Sequence
<220> FEATURE:
<223> OTHER INFORMATION: Synthetic Construct

<400> SEQUENCE: 199

Tyr His Asp
1

<210> SEQ ID NO 200
<211> LENGTH: 3
<212> TYPE: PRT
<213> ORGANISM: Artificial Sequence
<220> FEATURE:
<223> OTHER INFORMATION: Synthetic Construct

<400> SEQUENCE: 200

Tyr Asp Trp
1

<210> SEQ ID NO 201
<211> LENGTH: 3
<212> TYPE: PRT
<213> ORGANISM: Artificial Sequence
<220> FEATURE:
<223> OTHER INFORMATION: Synthetic Construct

<400> SEQUENCE: 201

Trp Asp Tyr
1

<210> SEQ ID NO 202
<211> LENGTH: 3
<212> TYPE: PRT
<213> ORGANISM: Artificial Sequence
```

```
<220> FEATURE:
<223> OTHER INFORMATION: Synthetic Construct

<400> SEQUENCE: 202

His Tyr Asp
1

<210> SEQ ID NO 203
<211> LENGTH: 3
<212> TYPE: PRT
<213> ORGANISM: Artificial Sequence
<220> FEATURE:
<223> OTHER INFORMATION: Synthetic Construct

<400> SEQUENCE: 203

His Trp Asp
1

<210> SEQ ID NO 204
<211> LENGTH: 3
<212> TYPE: PRT
<213> ORGANISM: Artificial Sequence
<220> FEATURE:
<223> OTHER INFORMATION: Synthetic Construct

<400> SEQUENCE: 204

Trp Thr Asp
1

<210> SEQ ID NO 205
<211> LENGTH: 3
<212> TYPE: PRT
<213> ORGANISM: Artificial Sequence
<220> FEATURE:
<223> OTHER INFORMATION: Synthetic Construct

<400> SEQUENCE: 205

Phe Pro Lys
1

<210> SEQ ID NO 206
<211> LENGTH: 3
<212> TYPE: PRT
<213> ORGANISM: Artificial Sequence
<220> FEATURE:
<223> OTHER INFORMATION: Synthetic Construct

<400> SEQUENCE: 206

His Trp Lys
1

<210> SEQ ID NO 207
<211> LENGTH: 3
<212> TYPE: PRT
<213> ORGANISM: Artificial Sequence
<220> FEATURE:
<223> OTHER INFORMATION: Synthetic Construct

<400> SEQUENCE: 207

Trp Glu Glu
1

<210> SEQ ID NO 208
<211> LENGTH: 3
<212> TYPE: PRT
<213> ORGANISM: Artificial Sequence
<220> FEATURE:
```

```
<223> OTHER INFORMATION: Synthetic Construct

<400> SEQUENCE: 208

Leu Leu Arg
1

<210> SEQ ID NO 209
<211> LENGTH: 3
<212> TYPE: PRT
<213> ORGANISM: Artificial Sequence
<220> FEATURE:
<223> OTHER INFORMATION: Synthetic Construct

<400> SEQUENCE: 209

Ser Tyr Phe
1

<210> SEQ ID NO 210
<211> LENGTH: 3
<212> TYPE: PRT
<213> ORGANISM: Artificial Sequence
<220> FEATURE:
<223> OTHER INFORMATION: Synthetic Construct

<400> SEQUENCE: 210

Glu Tyr Tyr
1

<210> SEQ ID NO 211
<211> LENGTH: 7
<212> TYPE: PRT
<213> ORGANISM: Artificial Sequence
<220> FEATURE:
<223> OTHER INFORMATION: Synthetic Construct

<400> SEQUENCE: 211

Asp Arg Asp Leu Thr Phe Ala
1               5

<210> SEQ ID NO 212
<211> LENGTH: 7
<212> TYPE: PRT
<213> ORGANISM: Artificial Sequence
<220> FEATURE:
<223> OTHER INFORMATION: Synthetic Construct

<400> SEQUENCE: 212

His Asn Trp Trp Ile Ile Ala
1               5

<210> SEQ ID NO 213
<211> LENGTH: 7
<212> TYPE: PRT
<213> ORGANISM: Artificial Sequence
<220> FEATURE:
<223> OTHER INFORMATION: Synthetic Construct

<400> SEQUENCE: 213

Glu Val Lys Ile Gly Asn Ala
1               5

<210> SEQ ID NO 214
<211> LENGTH: 3
<212> TYPE: PRT
<213> ORGANISM: Artificial Sequence
<220> FEATURE:
<223> OTHER INFORMATION: Synthetic Construct
```

<210> SEQ ID NO 215
<211> LENGTH: 3
<212> TYPE: PRT
<213> ORGANISM: Artificial Sequence
<220> FEATURE:
<223> OTHER INFORMATION: Synthetic Construct

<400> SEQUENCE: 215

Ala Tyr Pro
1

<210> SEQ ID NO 216
<211> LENGTH: 7
<212> TYPE: PRT
<213> ORGANISM: Artificial Sequence
<220> FEATURE:
<223> OTHER INFORMATION: Synthetic Construct

<400> SEQUENCE: 216

Glu Val Ala Asp Glu Glu Ala
1               5

<210> SEQ ID NO 217
<211> LENGTH: 7
<212> TYPE: PRT
<213> ORGANISM: Artificial Sequence
<220> FEATURE:
<223> OTHER INFORMATION: Synthetic Construct

<400> SEQUENCE: 217

Glu Tyr Tyr Val Asp Ala Ala
1               5

<210> SEQ ID NO 218
<211> LENGTH: 7
<212> TYPE: PRT
<213> ORGANISM: Artificial Sequence
<220> FEATURE:
<223> OTHER INFORMATION: Synthetic Construct

<400> SEQUENCE: 218

Tyr Asp Asn Pro Ile Asp Ala
1               5

<210> SEQ ID NO 219
<211> LENGTH: 7
<212> TYPE: PRT
<213> ORGANISM: Artificial Sequence
<220> FEATURE:
<223> OTHER INFORMATION: Synthetic Construct

<400> SEQUENCE: 219

Tyr Phe Asn Glu His Glu Ala
1               5

<210> SEQ ID NO 220
<211> LENGTH: 7
<212> TYPE: PRT
<213> ORGANISM: Artificial Sequence
<220> FEATURE:
<223> OTHER INFORMATION: Synthetic Construct

<400> SEQUENCE: 220

Glu Trp Gly Ala Asp Gly Ala
1               5

<210> SEQ ID NO 221
<211> LENGTH: 7
<212> TYPE: PRT
<213> ORGANISM: Artificial Sequence
<220> FEATURE:
<223> OTHER INFORMATION: Synthetic Construct

<400> SEQUENCE: 221

Asp Val Ile Tyr Ser His Ala
1               5

<210> SEQ ID NO 222
<211> LENGTH: 7
<212> TYPE: PRT
<213> ORGANISM: Artificial Sequence
<220> FEATURE:
<223> OTHER INFORMATION: Synthetic Construct

<400> SEQUENCE: 222

Trp His Ile Leu Glu Glu Ala
1               5

<210> SEQ ID NO 223
<211> LENGTH: 7
<212> TYPE: PRT
<213> ORGANISM: Artificial Sequence
<220> FEATURE:
<223> OTHER INFORMATION: Synthetic Construct

<400> SEQUENCE: 223

Asn Pro His Glu Asn Phe Ala
1               5

<210> SEQ ID NO 224
<211> LENGTH: 7
<212> TYPE: PRT
<213> ORGANISM: Artificial Sequence
<220> FEATURE:
<223> OTHER INFORMATION: Synthetic Construct

<400> SEQUENCE: 224

His Glu Asp Asn Gly Gly Ala
1               5

<210> SEQ ID NO 225
<211> LENGTH: 7
<212> TYPE: PRT
<213> ORGANISM: Artificial Sequence
<220> FEATURE:
<223> OTHER INFORMATION: Synthetic Construct

<400> SEQUENCE: 225

Ser Asp Ser Glu Gly Pro Ala
1               5

<210> SEQ ID NO 226
<211> LENGTH: 7
<212> TYPE: PRT
<213> ORGANISM: Artificial Sequence
<220> FEATURE:
<223> OTHER INFORMATION: Synthetic Construct

<400> SEQUENCE: 226

```
Glu Phe Gln Glu Phe Thr Ala
1               5

<210> SEQ ID NO 227
<211> LENGTH: 7
<212> TYPE: PRT
<213> ORGANISM: Artificial Sequence
<220> FEATURE:
<223> OTHER INFORMATION: Synthetic Construct

<400> SEQUENCE: 227

Gln Glu Gly Asp Glu Ile Ala
1               5

<210> SEQ ID NO 228
<211> LENGTH: 7
<212> TYPE: PRT
<213> ORGANISM: Artificial Sequence
<220> FEATURE:
<223> OTHER INFORMATION: Synthetic Construct

<400> SEQUENCE: 228

Asp Ile Tyr Ala Glu Thr Ala
1               5

<210> SEQ ID NO 229
<211> LENGTH: 7
<212> TYPE: PRT
<213> ORGANISM: Artificial Sequence
<220> FEATURE:
<223> OTHER INFORMATION: Synthetic Construct

<400> SEQUENCE: 229

Asp Arg Val Arg Glu Thr Ala
1               5

<210> SEQ ID NO 230
<211> LENGTH: 7
<212> TYPE: PRT
<213> ORGANISM: Artificial Sequence
<220> FEATURE:
<223> OTHER INFORMATION: Synthetic Construct

<400> SEQUENCE: 230

Phe Glu Glu Pro Gln Trp Ala
1               5

<210> SEQ ID NO 231
<211> LENGTH: 7
<212> TYPE: PRT
<213> ORGANISM: Artificial Sequence
<220> FEATURE:
<223> OTHER INFORMATION: Synthetic Construct

<400> SEQUENCE: 231

Phe Glu Gly Glu Glu Phe Ala
1               5

<210> SEQ ID NO 232
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
```

```
<223> OTHER INFORMATION: Xaa = Thr or Leu

<400> SEQUENCE: 232

Xaa Phe Asn Ile His Ala
1               5

<210> SEQ ID NO 233
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Gly, Pro, or Asn

<400> SEQUENCE: 233

Arg Tyr Pro Xaa Gln
1               5

<210> SEQ ID NO 234
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 6
<223> OTHER INFORMATION: Xaa = Gly, Pro, or Asn
<220> FEATURE:
<221> NAME/KEY: VARIANT
<222> LOCATION: 5
<223> OTHER INFORMATION: Arg or Gln

<400> SEQUENCE: 234

Xaa Xaa Tyr Tyr Xaa Xaa
1               5

<210> SEQ ID NO 235
<211> LENGTH: 5
<212> TYPE: PRT
<213> ORGANISM: Artificial Sequence
<220> FEATURE:
<223> OTHER INFORMATION: Synthetic Construct

<400> SEQUENCE: 235

Arg Tyr Pro Gly Gln
1               5

<210> SEQ ID NO 236
<211> LENGTH: 6
<212> TYPE: PRT
<213> ORGANISM: Artificial Sequence
<220> FEATURE:
<223> OTHER INFORMATION: Synthetic Construct

<400> SEQUENCE: 236

Asp Arg Tyr Tyr Arg Asp
1               5

<210> SEQ ID NO 237
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 237

Gln Ala Tyr Tyr Gln Arg
1               5

<210> SEQ ID NO 238
<211> LENGTH: 6
<212> TYPE: PRT
<213> ORGANISM: Artificial Sequence
<220> FEATURE:
<223> OTHER INFORMATION: Synthetic Construct

<400> SEQUENCE: 238

Gln Val Tyr Tyr Arg Pro
1               5

<210> SEQ ID NO 239
<211> LENGTH: 8
<212> TYPE: PRT
<213> ORGANISM: Artificial Sequence
<220> FEATURE:
<223> OTHER INFORMATION: Synthetic Construct

<400> SEQUENCE: 239

Pro His Gly Gly Gly Trp Gly Gln
1               5

<210> SEQ ID NO 240
<211> LENGTH: 8
<212> TYPE: PRT
<213> ORGANISM: Artificial Sequence
<220> FEATURE:
<223> OTHER INFORMATION: Synthetic Construct

<400> SEQUENCE: 240

Pro His Gly Gly Ser Trp Gly Gln
1               5

<210> SEQ ID NO 241
<211> LENGTH: 8
<212> TYPE: PRT
<213> ORGANISM: Artificial Sequence
<220> FEATURE:
<223> OTHER INFORMATION: Synthetic Construct

<400> SEQUENCE: 241

Pro His Gly Gly Gly Trp Ser Gln
1               5

<210> SEQ ID NO 242
<211> LENGTH: 9
<212> TYPE: PRT
<213> ORGANISM: Artificial Sequence
<220> FEATURE:
<223> OTHER INFORMATION: Synthetic Construct

<400> SEQUENCE: 242

Pro His Gly Gly Gly Gly Trp Ser Gln
1               5

<210> SEQ ID NO 243
<211> LENGTH: 10
<212> TYPE: PRT
<213> ORGANISM: Artificial Sequence
<220> FEATURE:
<223> OTHER INFORMATION: Synthetic Construct
```

-continued

```
<400> SEQUENCE: 243

Pro His Gly Gly Gly Ser Asn Trp Gly Gln
1               5                   10

<210> SEQ ID NO 244
<211> LENGTH: 6
<212> TYPE: PRT
<213> ORGANISM: Artificial Sequence
<220> FEATURE:
<223> OTHER INFORMATION: Synthetic Construct

<400> SEQUENCE: 244

Pro His Asn Pro Gly Tyr
1               5

<210> SEQ ID NO 245
<211> LENGTH: 6
<212> TYPE: PRT
<213> ORGANISM: Artificial Sequence
<220> FEATURE:
<223> OTHER INFORMATION: Synthetic Construct

<400> SEQUENCE: 245

Pro His Asn Pro Ser Tyr
1               5

<210> SEQ ID NO 246
<211> LENGTH: 6
<212> TYPE: PRT
<213> ORGANISM: Artificial Sequence
<220> FEATURE:
<223> OTHER INFORMATION: Synthetic Construct

<400> SEQUENCE: 246

Pro His Asn Pro Gly Tyr
1               5
```

PRION FREE NANOPARTICLE COMPOSITIONS AND METHODS OF MAKING THEREOF

RELATED APPLICATIONS

This application is a continuation of U.S. patent application Ser. No. 12/761,292, filed Apr. 15, 2010, which claims priority benefit to U.S. Provisional Patent Application No. 61/169,665, filed Apr. 15, 2009, and U.S. Provisional Patent Application No. 61/238,052, filed Aug. 28, 2009, the disclosures of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 638772010701_SEQUENCE_LISTING.txt, date recorded: Feb. 25, 2014, size: 41,293 bytes).

TECHNICAL FIELD

The present invention relates to prion-free compositions comprising nanoparticles comprising albumin and substantially water insoluble drugs, methods of making, and methods of using thereof.

BACKGROUND

Prion diseases, also known as transmissible spongiform encephalopathies (TSEs), are a group of fatal, transmittable neurodegenerative diseases. Specific examples of TSE include scrapie, which affects sheep and goats, bovine spongiform encephalopathy (BSE), transmissible mink encephalopathy, feline spongiform encephalopathy and chronic wasting disease (CWD). In humans, TSE diseases may present themselves as kuru, Creutzfeldt-Jekob disease (CJD), Gerstmann-Straussler-Scheinker Syndrome (GSS), fatal insomnia and variant Creutzfeldt-Jekob disease (vCJD). vCJD emerged in humans as a result of the BSE epidemic in Britain and is most probably caused by the consumption of food products derived from cattle infected with BSE or "mad cow disease." (Will et al. (1996) *Lancet* 347:921-925) Because the incubation period for the orally contracted disease may be more than 20 years in human, the true incidence of vCJD may not become apparent for many years.

In addition to ingestion of infected products of bovine origin, blood transfusion and organ transplantation represent another mode of transmission of vCJD among humans (Brown et al. (1998) *Transfusion* 38:810-816; Diringer et al. (1984) *Archives of Virology* 82:105-109; Manuelidis et al. (1978) *Nature* 271:778-779). Major concerns were raised since the mid-1990s that vCJD can be transmitted through blood transfusion or other blood products from TSE-infected individuals. These individuals may be asymptomatic during the long pre-clinical and incubation phase of vCJD, and blood obtained from such donors may be able to transmit the disease to persons receiving the blood or blood products derived from the donor.

There are so far at least four reported human cases of blood transfusion acquired vCJD in the United Kingdom. Of 64 people who received whole blood from 22 donors, 4 people went on to develop vCJD. In the first incidence, the recipient became ill 7 years after receiving red cells from the donor who remained asymptomatic and only showed signs of vCJD until 3 years after the donation (Llewely et al. (2004) *Lancet* 363:417-421). In the second incidence, the donor died of vCJD two years after donation, and the recipient died of an aneurysm (not vCJD) 5 years after donation (Peden et al. (2004) *Lancet* 364:527-529). On autopsy of the recipient, PrPsc was present in lymph node and spleen, but not the brain. In the third incidence, the recipient died of vCJD seven and half years after transfusion from a donor who developed vCJD 20 months after the donation (Wroe et al. (2006) *Lancet* 368:2061-2067). The fourth incident occurred in a recipient eight and half years after a transfusion from the same donor in the third case (Health Protection Agency-*Health Protection Report*, (2007) Vol 1, No 3, 26. Available at: http://www.hpa.org.uk/hpr/archives/2007/news2007/news0307.htm).

A common feature of all prion diseases is the conversion of the normal cellular prion protein (PrPc) into an abnormal isoform (PrPsc). The difference between PrPc and PrPsc are believed to be purely conformational, with PrPc having primarily alpha-helical structures and PrPsc having primarily beta sheets that frequently assemble to form aggregates. PrPsc acts as a template to induce normal protein molecules to convert into the same abnormal isoform, which then in turn covert more PrPc into PrPsc (Prusiner et al. (1998) *Proc. Natl. Acad. Sci. USA* 95:13363-13383). This autocatalytic process leads to exponential formation of neurotoxic PrPsc aggregates (Aguzzi et al. (2007) *Nat Rev Mol. Cell. Biol.* 8:552-561). Prion protein ligands and uses thereof have been described in WO04/050851, WO06/010915, WO04/090102, and WO06/044459.

Studies have shown that the earliest appearance of prion infectivity in the blood may occur during the early stage of the incubation period of the disease (Brown et al. (2006) *Blood infectivity in the transmissible spongiform encephalopathies.* Chapter 4 In: Turner M L, ed. 95-118). Because it can be a long time before the onset of disease symptoms, silently infected individuals may still be considered as healthy active blood donors. Furthermore, some individuals may be permanently or transiently infected without developing the disease. It is thus difficult if not impossible to ensure that sources of blood for blood derived products are prion free.

Albumin-based nanoparticle compositions have been developed as a drug delivery system for delivering substantially water insoluble drugs. See, for example, U.S. Pat. Nos. 5,916,596; 6,506,405; 6,749,868, and 6,537,579 and also in U.S. Pat. Pub. Nos. 2005/0004002 and 2007/0082838. The albumin-based nanoparticle technology utilizes the unique natural properties of the protein albumin to transport and deliver substantially water insoluble drugs to the site of disease. These nanoparticles are readily incorporated into the body's own transport processes and are able to exploit the tumors' attraction to albumin, enabling the delivery of higher concentrations of the active drug to the target site. In addition, the albumin-based nanoparticle technology offers the ability to improve a drug's solubility by avoiding the need for toxic chemicals, such as solvents, in the administration process, thus potentially improving safety through the elimination of solvent-related side effects.

The disclosures of all publications, patents, patent applications and published patent applications referred to herein are hereby incorporated herein by reference in their entirety.

BRIEF SUMMARY OF THE INVENTION

The present invention in one aspect provides prion-free nanoparticle compositions (such as pharmaceutical compositions). In some embodiments, there is provided a composition comprising nanoparticles comprising albumin and a substantially water insoluble pharmacologically active agent, wherein the composition is substantially free of a prion protein. In some embodiments, the composition is sterile. In some embodiments, the composition is sterile filterable. In some embodiments, the composition further comprises a pharmaceutically acceptable carrier.

In some embodiments, the composition has less than about 100 fg/ml prion protein. In some embodiments, the composition has a prion infectivity of less than about 10 IU-ic/ml. In some embodiments, the composition has a prion infectivity of less than about 1 $LD_{50}$/ml.

In some embodiments, the composition does not show the presence of a prion protein based on a protein misfolding cyclic amplification (PMCA) assay. In some embodiments, the composition does not show the presence of a prion protein based on an IPCR assay. In some embodiments, the composition has a prion infectivity of less than about 10 IU-ic/ml and does not show the presence of a prion protein based on a PMCA assay. In some embodiments, the composition has a prion infectivity of less than about 10 IU-ic/ml and does not show the presence of a prion protein based on an IPRC assay.

The compositions described herein are generally substantially free of PrPsc. In some embodiments, the composition is also substantially free of PrPc. In some embodiments, the molar ratio of PrPsc and PrPc in the composition is no greater than about 1:1, such as no great than about any one of 1:10, 1:100, 1:1000, 1:10000, or 1:100000.

The composition described herein in some embodiments contains an amount (for example, a trace amount) of substances introduced during a prion-removal process. For example, in some embodiments, there is provided a composition comprising nanoparticles comprising albumin and a substantially water insoluble pharmacologically active agent, wherein the composition is substantially free of a prion protein, and wherein the composition comprises an amount (for example, a trace amount) of a ligand capable of binding to a prion protein. In some embodiments, there is provided a composition comprising nanoparticles comprising albumin and a substantially water insoluble pharmacologically active agent, wherein the composition is substantially free of a prion protein, and wherein the composition comprises an amount (for example, a trace amount) of a supporting material (such as supporting material described herein, including a resin). In some embodiments, there is provided a composition comprising nanoparticles comprising albumin and a substantially water insoluble pharmacologically active agent, wherein the composition is substantially free of a prion protein, and wherein the composition comprises an amount of a PRDT resin (for example, a trace amount of a PRDT resin). In some embodiments, there is provided a composition comprising nanoparticles comprising albumin and a substantially water insoluble pharmacologically active agent, wherein the composition is substantially free of a prion protein, and wherein the composition comprises an amount of a DVR resin (for example, a trace amount of a DVR resin).

In some embodiments, the level of an albumin stabilizer in the composition is less than that of a composition wherein the albumin has not been cleared by a prion-removal process. These albumin stabilizers include, for example, N-acetyl tryptophanate and sodium caprylate.

In some embodiments, the composition is bioequivalent to a composition wherein the albumin has not been cleared by a prion-removal process.

In some embodiments, there is provided a composition comprising nanoparticles comprising albumin and a substantially water insoluble pharmacologically active agent, wherein the albumin in the composition was obtained by a method comprising a prion-removal process, said prion removal process comprising contacting an initial albumin composition with a ligand capable of binding to a prion protein. In some embodiments, the prion-removal process further comprises removing said ligand and proteins bound thereto from said albumin composition.

In some embodiments, there is provided a composition comprising nanoparticles comprising albumin and a substantially water insoluble pharmacologically active agent, wherein the albumin in the composition was obtained by a method comprising: a) contacting an initial albumin composition with a ligand capable of binding to a prion protein to cause formation of a complex between the ligand and a prion protein, and b) removing the complex from the initial composition.

In some embodiments, the initial albumin composition is a blood derived product. In some embodiments, the initial albumin composition is an albumin composition prepared from a body fluid (such as blood). In some embodiments, the albumin is human serum albumin.

In some embodiments, the ligand is a peptide (such as any peptides provided in Table 1). In some embodiments, the ligand is an antibody recognizing a prion protein. In some embodiments, the ligand is a chemical compound (such as triazine-based compounds). In some embodiments, the ligand comprises an amino group, such as an amino group on an amino resin.

The ligand can be attached to a supporting material, including, for example, column, bead, matrix, filter, and membrane.

In another aspect, there are provided methods of producing prion-free nanoparticle compositions. For example, in some embodiments, there is provided a method of producing a composition comprising nanoparticles comprising albumin and a substantially water insoluble pharmacologically active agent, said method comprising subjecting a mixture comprising an albumin solution and an organic phase containing said substantially water insoluble pharmacologically active agent dispersed in an organic solvent to a high shear condition, wherein the albumin was obtained by a method comprising removing a prion protein from an initial albumin composition. In some embodiments, there is provided a method of producing a composition comprising nanoparticles comprising albumin and a substantially water insoluble pharmacologically active agent, said method comprising subjecting a mixture comprising an albumin solution and an organic phase containing said substantially water insoluble pharmacologically active agent dispersed in an organic solvent to a high shear condition, wherein the albumin was obtained by a method comprising contacting an initial albumin composition with a ligand capable of binding to a prion protein. In some embodiments, there is provided a method of producing a composition comprising nanoparticles comprising albumin and a substantially water insoluble pharmacologically active agent, said method comprising subjecting a mixture comprising an albumin solution and an organic phase containing said substantially water insoluble pharmacologically active agent dispersed in an organic solvent to a high shear condition, wherein the albumin was obtained by a method comprising: a) contacting an initial albumin composition with a ligand capable of binding to a prion protein, and b) removing the ligand and protein bound thereto from the initial composition.

In some embodiments, there is provided a method of producing a composition comprising nanoparticles comprising albumin and a substantially water insoluble pharmacologically active agent, said method comprising: a) removing a prion protein from an initial albumin composition; b) subjecting a mixture comprising a solution comprising the prion-removed albumin and an organic phase comprising said substantially water insoluble pharmacologically active agent dispersed in an organic solvent to a high shear condition. In some embodiments, there is provided a method of producing a composition comprising nanoparticles comprising albumin and a substantially water insoluble pharmacologically active agent, said method comprising: a) contacting an initial albumin composition with a ligand capable of binding to a prion protein to cause formation of a complex between the ligand and a prion protein, b) removing the complex from the albumin initial composition; and c) subjecting a mixture comprising a solution comprising the prion-removed albumin and an organic phase comprising said substantially water insoluble pharmacologically active agent dispersed in an organic solvent to a high shear condition.

In some embodiments, there is provided a method of producing a composition comprising nanoparticles comprising albumin and a substantially water insoluble pharmacologically active agent, comprising: a) contacting an albumin solution with a ligand capable of binding to a prion protein, b) removing the ligand and proteins bound thereto from the albumin solution, and c) subjecting a mixture comprising said albumin solution and an organic phase comprising said substantially water insoluble pharmacologically active agent dispersed in an organic solvent to a high shear condition. In some embodiments, the mixture contains substantially no surfactants.

The prions can be removed during the formation of the nanoparticles. For example, in some embodiments, there is provided a method of producing a composition comprising nanoparticles comprising albumin and a substantially water insoluble pharmacologically active agent, comprising: a) contacting a mixture comprising an albumin solution and an organic phase comprising said substantially water insoluble pharmacologically active agent dispersed in an organic solvent with a ligand capable of binding to a prion protein. In some embodiments, the method further comprises: b) removing the ligand and proteins bound thereto from the mixture. In some embodiments, the method further comprises c) subjecting the mixture to a high shear condition. In some embodiments, the mixture contains substantially no surfactants.

The prion proteins can also be removed after the formation of the nanoparticle composition. For example, in some embodiments, there is provided a method of producing a composition comprising nanoparticles comprising albumin and a substantially water insoluble pharmacologically active agent, comprising contacting a mixture comprising an organic phase comprising said substantially water insoluble pharmacologically active agent dispersed in an organic solvent and an albumin solution with a ligand capable of binding to a prion protein, wherein the mixture has been subjected to a high shear condition prior to contacting with the ligand. In some embodiments, there is provided a method of producing a composition comprising nanoparticles comprising albumin and a substantially water insoluble pharmacologically active agent, comprising: a) subjecting a mixture comprising an organic phase comprising said substantially water insoluble pharmacologically active agent dispersed in an organic solvent and an albumin solution to a high shear condition, and b) contacting the mixture with a ligand capable of binding to a prion protein. In some embodiments, the method further comprises: c) removing the ligand and proteins bound thereto from the mixture. In some embodiments, the mixture is substantially free of surfactants.

In some embodiments, there is provided a method of removing a prion protein from a composition suspected of containing a prion protein comprising nanoparticles comprising albumin and a substantially water insoluble pharmacologically active agent, said method comprising a) contacting the nanoparticle composition with a ligand capable of binding to a prion protein, b) removing the ligand and proteins bound thereto from the nanoparticle composition. In some embodiments, there is provided a method of removing a prion protein from an albumin composition suspected of containing an abnormal prion protein, comprising: a) contacting the composition comprising albumin with a ligand capable of binding to a prion protein, b) removing the ligand and proteins bound thereto from the albumin composition, wherein said albumin composition is used to produce a composition comprising nanoparticles comprising nanoparticles comprising albumin and a substantially water insoluble pharmacologically active agent.

In some embodiments, there is provided a method of removing a prion protein from a composition comprising nanoparticles comprising albumin and a substantially water insoluble pharmacologically active agent, comprising: a) determining the presence or absence of a prion protein in the composition, b) contacting the composition with a ligand capable of binding to a prion protein, and c) removing the ligand and proteins bound thereto from the composition.

Also provided are compositions made during the prion removal process. For example, in some embodiments, there is provided a composition comprising nanoparticles comprising albumin and a substantially water insoluble pharmacologically active agent, further comprising a ligand capable of binding to a prion protein. In some embodiments, there is provided a mixture comprising nanoparticle comprising albumin and a substantially water insoluble pharmacologically active agent, and a ligand capable of binding to a prion protein attached to a supporting material, such as one or more supporting materials described herein. In some embodiments, there is provided a column loaded with a composition comprising nanoparticles comprising albumin and a substantially water insoluble pharmacologically active agent, wherein the column comprises a ligand capable of binding to a prion protein.

Also provided are compositions made by methods described herein. Also provided are methods of using the prion-free compositions described herein. For example, in some embodiments, there is provided a method of administering a composition comprising nanoparticles comprising albumin and a substantially water insoluble pharmacologically active agent, wherein the composition is substantially free of a prion protein. In some embodiments, there is provided a method of treating a disease (such as cancer) comprising administering a composition comprising nanoparticles comprising albumin and a substantially water insoluble pharmacologically active agent, wherein the composition is substantially free of a prion protein.

In some embodiments, there is provided a method of administering a composition comprising nanoparticles comprising albumin and a substantially water insoluble pharmacologically active agent, wherein the albumin in the composition was obtained by a method comprising a prion-removal process, said prion-removal process comprising contacting an initial albumin composition with a ligand capable of binding to a prion protein. In some embodiments, the prion removal process further comprises removing said ligand and proteins bound thereto from said albumin composition. In some embodiments, there is provided a method of treating a disease (such as cancer) comprising administering a composition comprising nanoparticles comprising albumin and a substantially water insoluble pharmacologically active agent, wherein the albumin in the composition was obtained by a method comprising a prion-removal process, said prion removal process comprising contacting an initial albumin composition with a ligand capable of binding to a prion protein.

Also provided are kits and dosage forms (such as vials for example sealed vials) comprising the prion-free nanoparticle compositions described herein and kits useful for methods described herein. Further provided are systems (including apparatus) for carrying out one or more methods described herein.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF FIGURES

FIG. 3 provides western blots and SDS-PAGE gels of D4 resin challenged with 0.01% and 0.005% scrapie hamster brain homogenate in 20% or 25% albumin AMN31 was the positive control resin. The signal observed was the bound fraction. "–PK" and "+PK" denotes absence or presence of Proteinase K digestion.

FIG. 9 shows the Western blot interference testing of 25% albumin solution with centrifugation (with and without 10-fold concentration).

DETAILED DESCRIPTION OF THE INVENTION

Figure 1:
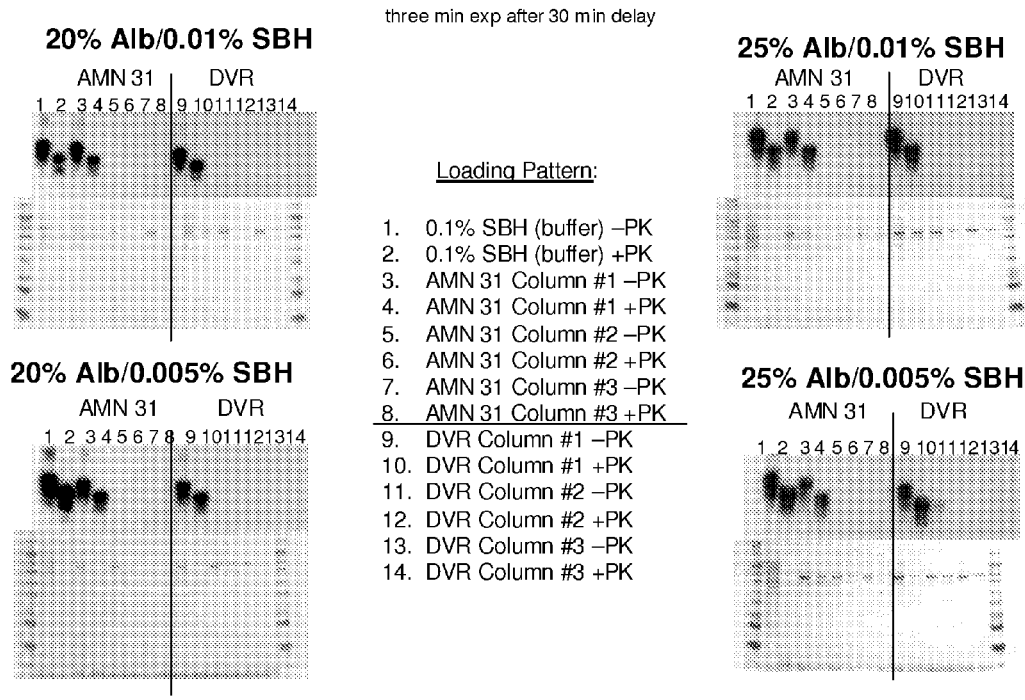
FIG. 1 provides western blots and SDS-PAGE gels of DVR resin challenged with 0.01% and 0.005% scrapie hamster brain homogenate in 20% or 25% albumin AMN31 was the positive control resin. The signal observed was the bound fraction. "–PK" and "+PK" denotes absence or presence of Proteinase K digestion.

The present invention provides prion-free compositions (such as pharmaceutical compositions) comprising nanoparticles comprising albumin and substantially water insoluble pharmacologically active agents and methods of making prion-free compositions.

The present invention in one aspect provides compositions (such as pharmaceutical compositions) comprising nanoparticles comprising albumin and substantially water insoluble pharmacologically active agents, wherein the composition is substantially free of a prion protein.

In another aspect, there is provided a method of making a prion-free composition (such as pharmaceutical compositions) comprising nanoparticles comprising albumin and substantially water insoluble pharmacologically active agent. Compositions made during the method of making process are also provided.

In another aspect, there is provided a method of using a prion-free composition (such as pharmaceutical compositions) comprising nanoparticles comprising albumin and substantially water insoluble pharmacologically active agent.

Also provided are kits and dosage forms (such as vials for example sealed vials) comprising the prion-free nanoparticle compositions described herein and kits and systems (including apparatus) useful for methods described herein.

"Prion free" is used herein for convenience and generally to describe the inventive compositions and is meant to encompass all embodiments described herein.

Reference to "about" a value or parameter herein includes (and describes) embodiments that are directed to that value or parameter per se. For example, description referring to "about X" includes description of "X."

It is understood that aspect and embodiments of the invention described herein include "consisting" and/or "consisting essentially of" aspects and embodiments.

Prion-Free Nanoparticle Compositions

The present invention provides a composition (such as a pharmaceutical composition) comprising nanoparticles comprising albumin and a substantially water insoluble pharmacologically active agent, wherein the composition is substantially free of a prion protein. In some embodiments, the composition is sterile. In some embodiments, the composition is sterile filterable. In some embodiments, the composition further comprises a pharmaceutically acceptable carrier.

In some embodiments, a prion protein cannot be detected in the composition by a detection method having a detection sensitivity of about 100 fg/ml or higher, that is, the test result is negative in an assay using a method having a detection sensitivity of about 100 fg/ml or higher (for example a detection sensitivity of about 50 fg/ml, about 10 fg/ml, about 1 fg/ml, about 0.1 fg/ml). The prion content in the composition can be determined directly from the composition. Alternatively, the composition can be processed prior to the determination, for example, concentrated or enriched in order to facilitate the detection and quantitation of the prion protein in the composition.

One way of determining whether or not a composition is substantially free of a prion protein is in vivo infectivity assay. For example, in vivo infectivity can be demonstrated by inoculation of the testing composition in mouse, mink, hamster, or goat models. Infectivity can be determined by lethal dose (LD50), i.e., the dose which when administered by a given route (such as by intracerebral route) induces disease in 50% of exposed animals. Alternatively, infectivity can be determined by infectious units, i.e., the minimal infectious dose capable of transmitting the disease to one experimental animal to another by a given route. Generally, 100 IU-ic/ml (infectious unit determined by intracerebral route) corresponds to about 10 LD50/ml and 1 pg/ml of prion protein.

Another method for determining a prion protein in the composition is immuno-polymerase chain reaction (IPCR), a technique whereby the exponential amplification ability of PCR is coupled to the detection of proteins by antibodies in an ELISA format and is applied in a modified real-time IPCR method to detect ultra-low levels of prion protein. See Barletta et al., J. Virology Method, 127 (2005):154-104. Using IPCR, recombinant hamster PrPc was consistently detected at 1 fg/ml and proteinase K (PK)-digested scrapie infected hamster brain homogenates diluted to $10^{-8}$ (approximately 10-100 infectious units) was detected with a semi-quantitative dose response.

In some embodiments, the prion protein in the composition is determined by Protein Misfolding Cyclic Amplification (PMCA). This method has been used to detect PrPsc in the blood. Other methods suitable for determining a prion protein in the composition include, but not limited to: quantitative sandwich ELISA using time-resolved dissociation-enhanced fluorescence technology; dual-color fluorescent confocal scanning; conformation dependent immunoassay (CDI). Western blotting, bead blot, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods can also be developed to detect prion proteins in the composition.

In some embodiments, the composition is substantially free of a prion protein based on one of the assays for detecting prion proteins (such as any one of the assays described above). In some embodiments, two or more assays are used to analyze the composition, and the correlation between these different assays is used to determine whether or not the composition is free of a prion protein.

Thus, in some embodiments, there is provided a composition comprising nanoparticles comprising albumin and a substantially water insoluble pharmacologically active agent, wherein the composition is substantially free of a prion protein. In some embodiments, the composition has a prion infectivity of less than about 100 fg/ml. In some embodiments, the composition has a prion infectivity of less than about 10 IU-ic/ml. In some embodiments, the composition has a prion infectivity of less than about 1 LD50/ml. In some embodiments, the composition does not show the presence of a prion protein based on the protein misfolding cyclic amplification (PMCA) assay. In some embodiments, the composition does not show the presence of a prion protein based on the IPCR assay. In some embodiments, the composition has a prion infectivity of less than about 10 IU-ic/ml and does not show the presence of a prion protein based on the PMCA assay. In some embodiments, the In some embodiments, the composition has a prion infectivity of less than about 10 IU-ic/ml and does not show the presence of a prion protein based on the IPRC assay. In some embodiments, the composition is free of prion protein based on the standard provided in the Guideline for the Investigation of Manufacturing Processes for Plasma-Derived Medicinal Products with Regard to vCJD Risk (CPMP5136/03), available at http://www.emea.europa.eu/pdfs/human/bwp/513603en.pdf, the content of which is incorporated herein in its entirety.

The compositions described herein are generally substantially free of PrPsc. In some embodiments, the composition is also substantially free of PrPc. In some embodiments, the molar ratio of PrPsc and PrPc in the composition is no greater than about 1:1, such as no great than about any one of 1:10, 1:100, 1:1000, 1:10000, or 1:100000.

In some embodiments, the composition is substantially free of a prion protein from human, bovine, sheep, and rodent (such as hamster, mice, and mink). In some embodiments, the composition is substantially free of the H-type prion protein, the L-type prion protein, or both. In some embodiments, the composition is substantially free of cell-bound of prion protein, the free prion protein, or both.

The term "PrPc" used herein refers to the native prion protein molecule which is naturally expressed within the body of the mammalian. The term "PrPsc" used herein refers to the conformationally altered form of the PrPc molecule that is thought to be infectious.

"Albumin" used herein refers to naturally occurring albumin and does not encompass albumin produced recombinantly. Naturally occurring albumin is advantageous over recombinant albumin because it is the natural ligand for albumin receptors in vivo. The albumin used in the methods described herein generally retains the post-translational modifications of albumin and thus has reduced risks of immunogenicity. In some embodiments, the albumin is obtained from a blood-derived composition. "Blood derived composition" used herein include whole blood, red blood cell concentrate, plasma, serum, platelet rich and platelet poor fraction, platelet concentrate, while blood cell, blood plasma precipitate, blood plasma fractionation precipitate and supernatant, plasma fractionation intermediate, various other substances which are derived from blood, and the like. In some embodiments, the albumin is from human. In some embodiments, the albumin is from an animal such as bovine, sheep, and rodent (such as mouse, hamster, and mink). In some embodiments, the albumin is obtained from a population of individuals (such as human) at least some of which have been infected with prions. In some embodiments, the albumin is obtained from a population of individuals (such as human) at least some of which are suspected of having been infected with prions. In some embodiments, the albumin is obtained from a large batch-size pool of individuals.

The composition described herein in some embodiments contains a trace amount of substances introduced during the prion-removal process. For example, in some embodiments, there is provided a composition comprising nanoparticles comprising albumin and a substantially water insoluble pharmacologically active agent, wherein the composition is substantially free of a prion protein, and wherein the composition comprises a trace amount of a ligand capable of binding to a prion protein. In some embodiments, there is provided a composition comprising nanoparticles comprising albumin and a substantially water insoluble pharmacologically active agent, wherein the composition is substantially free of a prion protein, and wherein the composition comprises a trace amount of a supporting material (such as material from a supporting material described herein, including a resin). In some embodiments, there is provided a composition comprising nanoparticles comprising albumin and a substantially water insoluble pharmacologically active agent, wherein the composition is substantially free of a prion protein, and wherein the composition comprises a trace amount of a ligand capable of binding to a prion protein and a trace amount of a supporting material (such as material from a supporting material described herein, including a resin).

"Trace amount" refers to a detectable amount that does not affect the property of the composition, for example in terms of bioavailability and/or bioequivalency.

In some embodiments, the composition is bioequivalent to a composition wherein the albumin has not been cleared by a prion-removal process. Bioequivalence can be established, for example, by a 90% confidence interval of between 0.80 and 1.25 for both Cmax and AUC, or a 90% confidence interval of between 0.80 and 1.25 of AUC and a 90% confidence interval of between 0.70 and 1.43 for Cmax.

In some embodiments, the level of an albumin stabilizer in the composition is less than that of a composition wherein the albumin has not been cleared by a prion-removal process. These albumin stabilizers include, for example, N-acetyl tryptophanate and sodium caprylate.

The compositions described herein generally encompass nanoparticles comprising a substantially water insoluble pharmaceutically active agent and an albumin. In some embodiments, the nanoparticle composition comprises nanoparticles comprising a substantially water insoluble pharmacologically active agent and an albumin. In some embodiments, the nanoparticles in the composition described herein have an average diameter of no greater than about 1000 nm, including for example no greater than about any one of 900, 800, 700, 600, 500, 400, 300, 200, 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of all the nanoparticles in the composition have a diameter of no greater than about 1000 nm, including for example no greater than about any one of 900, 800, 700, 600, 500, 400, 300, 200, 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of all the nanoparticles in the composition fall within the range of about 20 to about 200 nm, including for example any one of about 30 to about 180 nm, and any one of about 40 to about 150, about 50 to about 120, and about 60 to about 100 nm.

In some embodiments, at least about 5% (including for example at least about any one of 10%, 15%, 20%, 25%, 30%, 40%, 50%, 60%, 70%, 80%, or 90%) of the albumin in the nanoparticle portion of the composition are cross-linked (for example crosslinked through one or more disulfide bonds).

In some embodiments, the nanoparticles comprise the substantially water insoluble pharmacologically active agent (such as paclitaxel) coated with an albumin, (e.g., human serum albumin). In some embodiments, the composition comprises substantially water insoluble pharmacologically active agent in both nanoparticle and non-nanoparticle forms, wherein at least about any one of 50%, 60%, 70%, 80%, 90%, 95%, or 99% of the substantially water insoluble pharmacologically active agent in the composition are in nanoparticle form. In some embodiments, the substantially water insoluble pharmacologically active agent in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of substantially water insoluble pharmacologically active agent that is substantially free of polymeric materials (such as polymeric matrix).

In some embodiments, the nanoparticle composition is substantially free (such as free) of surfactants or organic solvent (such as Cremophor®, Tween 80, or any other organic solvents used for the administration of substantially water insoluble pharmacologically active agents). In some embodiments, the nanoparticle composition contains less than about any one of 20%, 15%, 10%, 7.5%, 5%, 2.5%, 1% or less organic solvent.

The removal of prion from the albumin-containing composition makes it possible to administer higher amounts of albumin without being concerned about prions. The present invention thus also contemplates compositions (such as pharmaceutical compositions) comprising nanoparticles comprising albumin and substantially water insoluble pharmacologically active agent, wherein the weight ratio of albumin to the substantially water insoluble pharmaceutical agent is about 20:1 or more, such as about any of about 30:1 or more, about 40:1 or more, or about 50:1 or more. Exemplary ratios include, for example, about 20:1 to about 40:1, about 40:1 to about 60:1, about 60:1 to about 80:1, or about 90:1 to about 100:1. In some embodiments, the weight ratio of albumin and substantially water insoluble pharmacologically active agent in the nanoparticle composition is about 18:1 or less, such as about 15:1 or less, for example about 10:1 or less. In some embodiments, the weight ratio of albumin and substantially water insoluble pharmacologically active agent in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of albumin and substantially water insoluble pharmacologically active agent in the nanoparticle portion of the composition is about any one of 1:2, 1:3, 1:4, 1:5, 1:6, 1:7, 1:8, 1:9, 1:10, 1:11, 1:12, 1:13, 1:14, 1:15, or less.

In some embodiments, the particle composition comprises one or more of the above characteristics.

In some embodiments, the nanoparticle composition is Abraxane™. Nanoparticle compositions comprising other substantially water insoluble pharmacologically active agents (such as docetaxel and ortataxel) may also comprise one or more of the above characteristics.

In some embodiments, there is provided a composition comprising nanoparticles comprising albumin and a substantially water insoluble pharmacologically active agent, wherein the albumin in the composition was obtained by a method comprising a prion-removal process, said prion removal process comprising contacting an initial albumin composition with a ligand capable of binding to a prion protein. In some embodiments, the prion-removal process further comprises removing said ligand and proteins bound thereto from said albumin composition.

In some embodiments, there is provided a composition comprising nanoparticles comprising albumin and a substantially water insoluble pharmacologically active agent, wherein the albumin in the composition was obtained by a method comprising: a) contacting an initial composition comprising albumin with a ligand capable of binding to a prion protein to cause formation of a complex between the ligand and a prion protein, and b) removing the complex from the initial composition.

Nanoparticles comprising albumins and substantially water insoluble drugs are further described below in more detail. The method of removing prions from a composition (such as an initial albumin composition, a nanoparticle composition comprising albumin and a substantially water insoluble pharmacologically active agent, or an intermediate composition formed during the process of making the nanoparticles) are further described below in more detail. The present invention encompasses compositions produced by any of the methods described herein.

The compositions described herein generally have reduced prion protein level as compared to compositions wherein the albumin has not been cleared by a prion-removal process. For example, in some embodiments, the composition has less than about any of 50%, 40%, 30%, 20%, 10%, 5%, 4%, 3%, 2%, 1%, or less of prion protein than a composition wherein the albumin has not been cleared by a prion-removal process. In some embodiments, the composition has any of about 1, 2, 2.5, 3, 3.5, 4, 4.5, 5, 6, 7, or 8 logs less prion protein than a composition wherein the albumin has not been cleared by a prion-removal process. In some embodiments, the composition has any of about 1, 2, 2.5, 3, 3.5, 4, 4.5, 5, 6, 7, or 8 logs less infectivity than a composition wherein the albumin has not been cleared by a prion-removal process. In some embodiments, the composition of the present invention is bioequivalent to a composition wherein the albumin has not been cleared by a prion-removal process.

Although the present application focuses on albumin, it is to be understood that other proteins normally found in blood or plasma, which include, but are not limited to, immunoglobulin (including IgA and IgG), lipoproteins, apolipoprotein B, alpha-acid glycoprotein, beta-2-macroglobulin, thyroglobulin, transferin, fibronectin, factor VII, factor VIII, factor IX, factor X, and the like, are also contemplated. All relevant descriptions about albumin provided herein are equally applicable to these other proteins to the extent they are utilized in the formation of nanoparticles.

Methods of Making Prion-Free Nanoparticle Compositions

In another aspect, there are provided methods of producing prion-free nanoparticle compositions. For example, in some embodiments, there is provided a method of producing a composition comprising nanoparticles comprising albumin and a substantially water insoluble pharmacologically active agent, said method comprising subjecting a mixture comprising an albumin solution and an organic phase containing said substantially water insoluble pharmacologically active agent dispersed in an organic solvent to a high shear condition, wherein the albumin was obtained by a method comprising removing a prion protein from an initial albumin composition. In some embodiments, there is provided a method of producing a composition comprising nanoparticles comprising albumin and a substantially water insoluble pharmacologically active agent, said method comprising subjecting a mixture comprising an albumin solution and an organic phase containing said substantially water insoluble pharmacologically active agent dispersed in an organic solvent to a high shear condition, wherein the albumin was obtained by a method comprising contacting an initial albumin composition with a ligand capable of binding to a prion protein. In some embodiments, there is provided a method of producing a composition comprising nanoparticles comprising albumin and a substantially water insoluble pharmacologically active agent, said method comprising subjecting a mixture comprising an albumin solution and an organic phase containing said substantially water insoluble pharmacologically active agent dispersed in an organic solvent to a high shear condition, wherein the albumin was obtained by a method comprising: a) contacting an initial albumin composition with a ligand capable of binding to a prion protein, and b) removing the ligand and protein bound thereto from the initial composition.

In some embodiments, there is provided a method of producing a composition comprising nanoparticles comprising albumin and a substantially water insoluble pharmacologically active agent, said method comprising: a) removing a prion protein from an initial albumin composition; b) subjecting a mixture comprising a solution comprising the prion-removed albumin and an organic phase comprising said substantially water insoluble pharmacologically active agent dispersed in an organic solvent to a high shear condition. In some embodiments, there is provided a method of producing a composition comprising nanoparticles comprising albumin and a substantially water insoluble pharmacologically active agent, said method comprising: a) contacting an initial albumin composition with a ligand capable of binding to a prion protein to cause formation of a complex between the ligand and a prion protein, and b) removing the complex from the albumin initial composition; c) subjecting a mixture comprising a solution comprising the prion-removed albumin and an organic phase comprising said substantially water insoluble pharmacologically active agent dispersed in an organic solvent to a high shear condition.

In some embodiments, there is provided a method of producing a composition comprising nanoparticles comprising albumin and a substantially water insoluble pharmacologically active agent, comprising: a) contacting an albumin solution with a ligand capable of binding to a prion protein, b) removing the ligand and proteins bound thereto from the albumin solution, c) subjecting a mixture comprising said albumin solution and an organic phase comprising said substantially water insoluble pharmacologically active agent dispersed in an organic solvent to a high shear condition. In some embodiments, the mixture contains substantially no surfactants.

The prions can be removed during the formation of the nanoparticles. For example, in some embodiments, there is provided a method of producing a composition comprising nanoparticles comprising albumin and a substantially water insoluble pharmacologically active agent, comprising: a) contacting a mixture comprising an albumin solution and an organic phase comprising said substantially water insoluble pharmacologically active agent dispersed in an organic solvent with a ligand capable of binding to a prion protein. In some embodiments, the method further comprises: b) removing the ligand and proteins bound thereto from the mixture. In some embodiments, the method further comprises c) subjecting the mixture to a high shear condition. In some embodiments, the method further comprises removing the organic solvent from the mixture. In some embodiments, the mixture contains substantially no surfactants.

In some embodiments, there is provided a method of producing a composition comprising nanoparticles comprising albumin and a substantially water insoluble pharmacologically active agent, comprising: a) subjecting a mixture comprising an albumin solution and an organic phase comprising a substantially water insoluble pharmacologically active agent dispersed in an organic solvent to a high shear condition; and b) contacting the mixture with a ligand capable of binding to a prion protein. In some embodiments, the method further comprises: c) removing the ligand and proteins bound thereto from the mixture. In some embodiments, the method further comprises removing the organic solvent from the mixture. In some embodiments, the mixture contains substantially no surfactants.

In some embodiments, there is provided a method of producing a composition comprising nanoparticles comprising albumin and a substantially water insoluble pharmacologically active agent, comprising contacting a mixture comprising an organic phase comprising said substantially water insoluble pharmacologically active agent dispersed in an organic solvent and an albumin solution with a ligand capable of binding to a prion protein, wherein the mixture has been subjected to a high shear condition prior to contacting with the ligand. In some embodiments, there is provided a method of producing a composition comprising nanoparticles comprising albumin and a substantially water insoluble pharmacologically active agent, comprising: a) subjecting a mixture comprising an organic phase comprising said substantially water insoluble pharmacologically active agent dispersed in an organic solvent and an albumin solution to a high shear condition, and b) contacting the mixture with a ligand capable of binding to a prion protein. In some embodiments, the method further comprises: c) removing the ligand and proteins bound thereto from the mixture. In some embodiments, the method further comprises: d) removing the aqueous phase from the mixture. In some embodiments, the mixture is substantially free of surfactants.

In some embodiments, there is provided a method of producing a composition comprising nanoparticles comprising albumin and a substantially water insoluble pharmacologically active agent, comprising: a) subjecting a mixture comprising an organic phase comprising said substantially water insoluble pharmacologically active agent dispersed in an organic solvent and an albumin solution to a high shear condition, b) removing said organic solvent, and c) contacting the mixture with organic solvent removed with a ligand capable of binding to a prion protein. In some embodiments, the method further comprises: d) removing the ligand and proteins bound thereto from the mixture. In some embodiments, the method further comprises: d) removing the aqueous phase from the mixture. In some embodiments, the mixture is substantially free of surfactants.

In some embodiments, there is provided a method of producing a composition comprising nanoparticles comprising albumin and a substantially water insoluble pharmacologically active agent, comprising: a) subjecting a mixture comprising an organic phase comprising said substantially water insoluble pharmacologically active agent dispersed in an organic solvent and an albumin solution to a high shear condition, b) removing said organic solvent, c) adding albumin to the mixture, and d) contacting the mixture with a ligand capable of binding to a prion protein. In some embodiments, the method further comprises: e) removing the ligand and proteins bound thereto from the mixture. In some embodiments, the method further comprises: f) removing the aqueous phase from the mixture. In some embodiments, the mixture is substantially free of surfactants.

The methods described herein generally include the step of subjecting a mixture comprising an organic phase comprising the substantially water insoluble pharmacologically active agent dispersed in an organic solvent and an albumin solution to a high shear condition. In some embodiments, the high shear condition is high pressure homogenization, for example at a pressure in the range of about 3000 to about 30,000 psi, including for example about 6000 to about 25,000 psi, about 9000 to about 18,000 psi, about 10,000 to about 25,000 psi, about 15,000 to about 25,000 psi. In some embodiments, organic solvent is a mixture of a substantially water immiscible organic solvent (such as chloroform or methylene chloride) and a water soluble organic solvent (such as a water soluble alcohol, including ethanol and t-butanol). In some embodiments, the ratio (v/v) of the substantially water immiscible organic solvent and the water soluble organic solvent (for example the ratio of chloroform/ethanol or chloroform/butanol) is about any of 1:9, 1:8, 1:7, 1:6, 1:5, 1:4, 1:3, 1:2, 1:1, 2:1, 3:1, 4:1, 5:1, 6:1, 7:1, 8:1, or 9:1, or with a ratio of about any of 3:7, 5:7, 4:6. 6:4, 5:5, 6:5, 8:5, 9:5, 9.5:5, 5:3, 7:3, 6:4, or 9.5:0.5.

In some embodiments, the method further comprises removing the organic phase from the mixture (such as removal by evaporation under reduced pressure). In some embodiments, the method further comprises removing the aqueous phase from the mixture. In some embodiments, the method further comprises sterile filtering the nanoparticles formed by the method described above.

In some embodiments, there is provided a method of removing a prion protein from a composition suspected of containing a prion protein comprising nanoparticles comprising albumin and a substantially water insoluble pharmacologically active agent, said method comprising: a) contacting the nanoparticle composition with a ligand capable of binding to a prion protein, b) removing the ligand and proteins bound thereto from the nanoparticle composition. In some embodiments, there is provided a method of removing a prion protein from an albumin composition suspected of containing an abnormal prion protein, comprising: a) contacting the composition comprising albumin with a ligand capable of binding to a prion protein, b) removing the ligand and proteins bound thereto from the albumin composition, wherein said albumin composition is used to produce a composition comprising nanoparticles comprising nanoparticles comprising albumin and a substantially water insoluble pharmacologically active agent.

In some embodiments, there is provided a method of removing a prion protein from a composition comprising nanoparticles comprising albumin and a substantially water insoluble pharmacologically active agent, comprising: a) determining the presence or absence of a prion protein in the composition, b) contacting the composition with a ligand capable of binding to a prion protein, and c) removing the ligand and proteins bound thereto from the composition.

In some embodiments, one or more steps of the methods described herein are carried out in batch mode. In some embodiments, one of more steps of the methods described herein are carried out in continuous mode.

Removing Prion Prior to the Formation of Nanoparticles

The prion protein can be removed from an initial albumin composition before the albumin-containing nanoparticle compositions are made. Generally, the method comprises contacting an initial albumin composition with a ligand capable of binding to a prion protein, and removing the ligand and protein bound thereto from the albumin composition. This process can be repeated one or more times, with the same or a different ligand. Two or more ligands can also be used simultaneously during the prion removal process.

In some embodiments, the initial albumin composition is a blood derived composition. For example, in some embodiments, the initial albumin composition is whole blood, red blood cell concentrate, plasma, serum, platelet rich and platelet poor fraction, platelet concentrate, while blood cell, blood plasma precipitate, blood plasma fractionation precipitate and supernatant, or plasma fractionation intermediate. In some embodiments, the initial albumin composition is obtained from human. In some embodiments, the initial albumin composition is from an animal such as bovine, sheep, and rodent (such as mouse, hamster, and mink). In some embodiments, the initial albumin composition is obtained from a population of individuals (such as human) at least some of which have been infected with prions. In some embodiments, the initial albumin composition is obtained from a population of individuals (such as human) at least some of which are suspected of having been infected with prions.

In some embodiments, the initial albumin composition is an albumin composition prepared from a body fluid (such as blood) by any of various methods common in the art including ion exchange, affinity, gel permeation, and/or hydrophobic chromatography and/or by differential precipitation. In some embodiments, the initial composition is an albumin composition purified from the blood (such as human blood). In some embodiments, the initial albumin composition is an albumin composition purified from serum (such as human serum). In some embodiments, the initial albumin composition has a prion infectivity of about 100 IU-ic/ml, 90 IU-ic/ml, 50 IU-ic/ml, or 10 IU-ic/ml. In some embodiments, the concentration of albumin in the initial albumin composition is about 1% (w/v), including for example about 2%, 3%, 4%, 5%, 6%, 7%, 8%, 9%, 10%, 15%, 20%, 25%, or 30%.

During the prion-removal process, the ligand is brought into contact with the initial albumin composition and allowed to bind to prion proteins in the initial albumin composition. Conditions suitable for the binding can be determined and optimized to facilitate binding of the ligand to a prion protein based on the nature of the ligand and its binding specificity to the prion protein. The binding in some embodiments is carried out at a temperature of about 0° C. to about 39° C., including for example about 20° C. to about 25° C. The binding can be carried out at pH of about 4 to about 10, including for example about 5 to about 9, about 6 to about 8, about 6.8 to about 7.5, about 6.9 to about 7.4, or about 7. Optionally, blocking agents can be used to reduce non-specific binding to the ligand.

After the contacting step, the ligand and proteins bound thereto are removed from the rest of the composition. The term "removing" as used herein refers to the separation of the ligand and protein bound thereto from the albumin-containing composition. The separation can be carried out in a variety of ways, depending on the nature of the ligand and the supporting material (if any) used to facilitate the separation. For example, the ligand and proteins bound thereto can be separated out by chromatography, such as, but not limited to, thin-layer, column and batch chromatography; solid support and membrane separation; reactor separation; magnetic separation, immunoseparation; colloidal separation; sedimentation; precipitation; or centrifugation.

In some embodiments, ligand may be attached to a supporting material such as a bead or a membrane, which in turn is allowed to contact the initial albumin composition. Ligand-immobilized support is allowed to contact the initial albumin composition under a condition sufficient to cause formation of a prion-ligand complex. The solid phase is then separated from the composition, thereby removing the prion protein bound to the ligand from the sample. For example, in one exemplary embodiment, the ligands are immobilized in a column, such as a chromatography column, a sample (such as the initial albumin composition) is then passed through the column either due to the force of gravity or under pressure, such as in a high pressure liquid chromatography column. Prion proteins in the sample will bind to the ligand immobilized on the column, and the sample passing through can be collected. This process can repeat several times to achieve the desired result, using the same or different ligands.

The flow rate of a sample (such as the initial albumin composition) in a column can be adjusted to maximize the binding of the ligand and the prion proteins in a sample. In some embodiments, the binding is carried out at a flow rate of about 0.1 ml per minute to about 5.0 ml per minute, about 0.1 ml per minute to about 2.5 ml per minute, about 0.1 ml per minute to about 0.25 ml per minute, about 0.25 per minute to about 0.5 ml per minute, about 0.5 ml per minute to about 1.0 ml per minute, about 1.0 ml per minute to about 1.5 ml per minute, about 1.5 ml per minute to about 2.0 ml per minute, about 2.0 ml per minute to about 2.5 ml per minute, about 2.5 ml per minute to about 3.0 ml per minute, about 3.0 ml per minute to about 3.5 ml per minute, about 3.5 ml per minute to about 4.0 ml per minute, about 4.0 ml per minute to about 4.5 ml per minute, or about 4.5 ml per minute to about 5.0 ml per minute, including for example about 0.1 ml per minute, 0.25 ml per minute, 0.5 ml per minute, 1.0 ml per minute, 1.5 ml per minute, 1.7 ml per minute, 1.8 ml per minute, 1.9 ml per minute, 2.0 ml per minute, 2.1 ml per minute, 2.3 ml per minute, 2.5 ml per minute, 2.7 ml per minute, 3.0 ml per minute, 3.5 ml per minute, 4.0 ml per minute, 4.5 ml per minute, or 5.0 ml per minute. In some embodiments, the flow rate is at least about 10 ml per minute, such as at least about any of 20 ml per minute, 30 ml per minute, 40 ml per minute, 50 ml per minute.

The total flow-through volume or total flow-through time during a binding process can also be adjusted to maximize the binding of the ligand and the prion proteins in a sample (such as the initial albumin composition). In some embodiments, the total flow-through volume is about 1 time to about 1000 times of the column volume, including for example about 2 times to about 10 times of the column volume, about 10 times to about 20 times of the column volume, about 20 times to about 30 times of the column volume, about 30 times to about 40 times of the column volume, about 40 times to about 50 times of the column volume, about 50 times to about 1000 times of the column volume, about 50 times to about 500 times of the column volume, about 100 times to about 600 times of the column volume, or about 200 times to about 800 times of the column volume. In some embodiments, the total flow-through volume is about 100 times of the column volume. In other embodiments, the total flow-through volume is about 500 times of the column volume. In some embodiments, the total flow-through time is about 1 hour to about 30 hours, including for example about 2 hours to about 25 hours, about 3 hours to about 20 hours, or about 3 hours to about 17 hours. In some embodiments, the total flow-through time is any of about 3 hours, 4 hours, 6 hours, 8 hours, 10 hours, 12 hours, 14 hours, 16 hours, 17 hours, 18 hours, 19 hours, or 20 hours. In some embodiments, the total flow through time is more than about 24 hours. In some embodiments, the total flow through time is less than about 8, including for example any of 7, 6, 5, 4, 3, 2, 1, or 0.5 hours.

Alternatively, the ligand can first be brought into contact with the initial albumin composition, under a condition sufficient to cause formation of a prion-ligand complex. The prion-ligand complex is then subsequently removed by using a column, such as an affinity-based chromatography. To facilitate the separation, the ligand may be conjugated to a binding partner so that the ligand/prion complex can be removed via the binding partner, for example by using an affinity column containing a molecule that recognizes the binding partner.

In addition to batch or column chromatography, a variety of other configurations, modifications and variations of the use of the ligands for binding prion proteins are also envisioned. Such variations and modifications include, but are not limited to: batch processes, continuous processes, moving bed chromatography processes; low, medium, or high pressure processes; or small, medium or large scale processes. In some embodiments, the ligands are on a membrane, fibers bead, impregnated into a non-woven mesh, or coating fibers contained within a filter housing.

In some embodiments, the removal step does not significantly result in yield loss and/or change in the property and/or stability of the albumin. In some embodiments, the recovery of the albumin in its original biological state is substantially maintained at least to a level in excess of 50%, including for example 80%, or 90%, or more. In some embodiments, the recovery rate of albumin from the prion removal process is higher than any of about 80%, 90%, 95%, or 99%. In some embodiments, the concentration of albumin in the initial albumin composition is adjusted or controlled prior to the prion removal step in order to minimize non-specific binding and loss of albumin during the process. For example, the concentration of albumin can be in the range of about 1% to about 50%, about 5% to about 25%, about 5% to about 30%, about 5% to about 40%, about 5% to about 10%, about 10% to about 15%, about 15% to about 20%, about 20% to about 25%, about 25% to about 30% etc., including for example about 5%, 10%, 15%, 20%, 25%, or 30% albumin.

The resulting albumin composition can be analyzed to determine the clearance rate of the prion removal process. The ligand with bound prion proteins may also be analyzed (directly or after elution) to determine the clearance rate.

The removal of prion proteins can be evaluated based on reduction of prion protein or reduction of infectivity. In some embodiments, at least about 50%, including for example at least about 60%, 70%, 80%, 90%, 95%, 99%, or 100% of the prion proteins are removed from the initial albumin composition. In some embodiments, the infectivity of the post-removal albumin composition is at least about 10×, 20×, 30×, 40×, 50×, 80×, 100×, 200×, 500×, 1000×, $10^4$×, $10^5$×, $10^6$×, $10^7$×, $10^8$×, $10^9$× less than that of the initial albumin composition.

In some embodiments, serial infectivity is used to determine the clearance rate of the prion removal process. Serial dilutions of a samples are made and dilutions are examined for infectious activity, for example in an assay animal. The dilution at which half of the animals become infected is the infectious titer. For example, if a 5 fold dilution is required, the sample may be defined as having 5 logs of infectivity. By comparing the log infectivity of the initial albumin composition and that of the post-removal albumin composition, one can determine the clearance rate of the prion removal process. In some embodiments, the prion removal method results in a reduction of any one of 1, 1.1, 1.2, 1.3, 1.4, 1.5, 1.6, 1.7, 1.8, 1.9, 2, 3, or 4, 5, 6, 7, 8, 9, or 10 logs of infectivity.

In some embodiments, the clearance rate of the prion-removal process is determined based on spiking experiments with infectious materials by following steps described herein for the prion-removal method. Suitable spiking agents include, but are not limited to, brain homogenates, microsomes, caveolae-like domains, purified PrPsc, and prion fibrils. In some embodiments, the spiking agent is detergent solublized (such as sarkosyl solubilized). In some embodiments, the spiking ratio in the composition is in the range of about 0.001% to about 5%, about 0.001% to about 0.25%, about 0.001% to about 0.1%, about 0.001% to about 0.005%, about 0.005% to about 0.075%, about 0.075% to about 0.01%, about 0.01% to about 0.1%, about 0.1% to about 0.5%, about 0.5% to about 0.75%, about 0.75% to about 1%, about 1% to about 2%, about 2% to about 3%, or about 3% to about 5%, including for example about 0.001%, 0.005%, 0.075%, 0.01%, 0.1%, 0.5%, 0.75%, 1%, 2%, 3%, or 5%.

In some embodiments, the reduction factors (RF) is used to determine the clearance rate of the prion removal process. The RF can be calculated using the formula:

$$RF=(V_1 \times T_1)/(V_2 \times T_2)$$

or $$Log_{10}[RF]=[Log_{10}(V_2)+Log_{10}(T_2)]-[Log_{10}(V_2)+Log_{10}(T_2)].$$

Wherein $V_1$ and $T_1$ are the volume and titre of the initial albumin composition, respectively, and $V_2$ and $T_2$ are the volume and titre of the post-removal albumin composition. Reduction factors can be rounded to 1 decimal place after the final calculation. In some embodiments, a reduction factor of at least about 1.0, 1.5, 2.0, 2.5, 3.0, 3.5, 4.0, 4.5, 5.0, 5.5, 6.0, 6.5, 7.0, 7.5, or 8.0 $log_{10}$ infectivity of the prion proteins is removed from the initial albumin composition. For example, the prion protein can be removed by a reduction factor of greater than or equal to 2.5 $log_{10}$ in a 0.5% sarkosyl solubilized fraction spiked into a 20% albumin composition. As another example, the prion protein can also be removed by a reduction factor of greater than or equal to 2.0 $log_{10}$ in a 0.5% sarkosyl solubilized fraction spiked into a 25% albumin composition.

The removal of prions can be evaluated by standard Western blot analysis. For example, the post-binding ligands can first be treated with Proteinase K, which digests all PrPc but not PrPsc. The digest is then run on SDS gel and transblotted to a sheet of nitrocellulose or PVDF membrane. The separated PrPsc bands are then visualized using 3F4 or 6H4. 3F4 reacts with amino acid residues 109-112 PrP from humans, hamsters, and felines. In one exemplary embodiment, incubation was carried out at a concentration of 0.6 ug/ml for a minimum of one hour, after which excess antibody was washed away and the membranes incubated with a rabbit anti-mouse horse-radish peroxidase conjugate (1:1000 dilution) for a minimum of one hour. After extensive washing with TTBS, the membranes were developed using enhanced chemiluminescence. In some embodiments, the removal of prion proteins is evaluated according to the Guideline for the Investigation of Manufacturing Processes for Plasma-Derived Medicinal Products with Regard to vCJD Risk (CPMP5136/03).

Ligands Capable of Binding to a Prion Protein and Supporting Material

"Ligand" used herein refers to a molecule to which a prion protein or peptide binds. A "ligand capable of binding to a prion protein" refers to a ligand that specifically binds to a prion protein under suitable conditions. In some embodiments, the ligand specifically binds to a human prion protein. In some embodiments, the ligand specifically binds to a hamster prion protein. In some embodiments, the ligand specifically binds to a mouse protein. In some embodiments, the ligand has binds to prion proteins from multiple species. For example, in some embodiments, the ligand binds to human prion protein, hamster prion protein, and mouse prion protein.

In some embodiments, the ligand binds to the prion protein (such as a human prion protein, hamster prion protein, and/or mouse prion protein) with a high binding affinity. For example, in some embodiments, the ligand has a binding Kassociation of more than about any of $10^7$, $10^8$, $10^9$, $10^{10}$, or $10^{11}$.

A number of ligands have been identified that bind to prion protein and thus can be used in methods of the present invention. See, e.g., WO04/090102, WO04/050851, WO06/

010915, and WO06/044459. These include, for example, peptides, chemical compounds, and antibodies that specifically recognize a prion protein. The ligand can be used to remove all forms of prion proteins from a composition or can be selectively chosen to detect or remove a single form of prion protein.

In some embodiments, the ligand for removing prion is a peptide, such as peptides described in PCT published application No. WO04/050851. For example, in some embodiments, the ligand is a peptide having an amino acid of any of SEQ ID NOs: 1-232 as shown in Table 1. In some embodiments, the ligand is a tripeptide, such as peptides having an amino acid sequence of any one of SEQ ID NO:48, 102, 105, 108, 109, 110, 111, 143, 148, 193, 194, 195, 202, 203, 204, or 210. In some embodiments, the ligand is a peptide with six amino acids, such as 6-mers having an amino acid sequence of any one of SEQ ID NO: 152, 153, 180, 181, 182, 183, 185, 186, 187, 188, 189, or 190. In some embodiments, the ligand has an amino acid sequence of SEQ ID NO:150 or 151.

TABLE 1

Amino acid sequences binding to prion sequences

| | | | | |
|---|---|---|---|---|
| KIHKFLA (SEQ ID NO: 1) | WPA (SEQ ID NO: 51) | WQD (SEQ ID NO: 101) | ES(na)PRQA (SEQ ID NO: 151) | WDY (SEQ ID NO: 201) |
| GTHDFQA (SEQ ID NO: 2) | FNQ (SEQ ID NO: 52) | YFE (SEQ ID NO: 102) | VARENIA (SEQ ID NO: 152) | HYD (SEQ ID NO: 202) |
| KFGSTHA (SEQ ID NO: 3) | YHE (SEQ ID NO: 53) | NYE (SEQ ID NO: 103) | RWEREDA (SEQ ID NO: 153) | HWD (SEQ ID NO: 203) |
| FVNEIEA (SEQ ID NO: 4) | LFA (SEQ ID NO: 54) | SYA (SEQ ID NO: 104) | EWWETV (SEQ ID NO: 154) | WTD (SEQ ID NO: 204) |
| GLHFKSA (SEQ ID NO: 5) | NHY (SEQ ID NO: 55) | WDL (SEQ ID NO: 105) | SVYQLDA (SEQ ID NO: 155) | FPK (SEQ ID NO: 205) |
| GRVLHHA (SEQ ID NO: 6) | TLG (SEQ ID NO: 56) | WLE (SEQ ID NO: 106) | (na)HEFYGA (SEQ ID NO: 156) | HWK (SEQ ID NO: 206) |
| QKNSEWA (SEQ ID NO: 7) | WVD (SEQ ID NO: 57) | VQR (SEQ ID NO: 107) | HE(na)(na)LVA (SEQ ID NO: 157) | WEE (SEQ ID NO: 207) |
| HAYFTHA (SEQ ID NO: 8) | YWDQA (SEQ ID NO: 58) | YID (SEQ ID NO: 108) | A(na)VPV(na)A (SEQ ID NO: 158) | LLR (SEQ ID NO: 208) |
| WPKGAVA (SEQ ID NO: 9) | YVHEA (SEQ ID NO: 59) | RWD (SEQ ID NO: 109) | YFDYWLA (SEQ ID NO: 159) | SYF (SEQ ID NO: 209) |
| RPWKKAA (SEQ ID NO: 10) | WFDEA (SEQ ID NO: 60) | DVR (SEQ ID NO: 110) | FE(na)HRQA (SEQ ID NO: 160) | EYY (SEQ ID NO: 210) |
| PKHIWPA (SEQ ID NO: 11) | LQWYDA (SEQ ID NO: 61) | WSD (SEQ ID NO: 111) | WRHEPAA (SEQ ID NO: 161) | DRDLTFA (SEQ ID NO: 211) |
| HKLWGVA (SEQ ID NO: 12) | YTHSEA (SEQ ID NO: 62) | HWD (SEQ ID NO: 112) | SS(na)KKDA (SEQ ID NO: 162) | HNVVWIIA (SEQ ID NO: 212) |
| GGYKPYA (SEQ ID NO: 13) | WIDYEA (SEQ ID NO: 63) | WQD (SEQ ID NO: 113) | R(na)DKEAA (SEQ ID NO: 163) | EVKIGNA (SEQ ID NO: 213) |
| ENVSQNA (SEQ ID NO: 14) | VWIDAA (SEQ ID NO: 64) | WDD (SEQ ID NO: 114) | (na)HEIFPA (SEQ ID NO: 164) | SIV (SEQ ID NO: 214) |
| HTYYNGA (SEQ ID NO: 15) | WDEAEEA (SEQ ID NO: 65) | WED (SEQ ID NO: 115) | KWYHHRA (SEQ ID NO: 165) | AYP (SEQ ID NO: 215) |
| KKKSDHA (SEQ ID NO: 16) | YDSYDDA (SEQ ID NO: 66) | ITN (SEQ ID NO: 116) | HWWPHNA (SEQ ID NO: 166) | EVADEEA (SEQ ID NO: 216) |
| HHLKGTA (SEQ ID NO: 17) | NDFIDFA (SEQ ID NO: 67) | YED (SEQ ID NO: 117) | HWQVFYA (SEQ ID NO: 167) | EYYVDAA (SEQ ID NO: 217) |
| KKHGVWA (SEQ ID NO: 18) | YEPWGSA (SEQ ID NO: 68) | VADEEA (SEQ ID NO: 118) | FHE(na)EIA (SEQ ID NO: 168) | YDNPIDA (SEQ ID NO: 218) |
| DGTQAHA (SEQ ID NO: 19) | EYGDWWA (SEQ ID NO: 69) | YYVDAA (SEQ ID NO: 119) | HADF(na)QA (SEQ ID NO: 169) | YFNEHEA (SEQ ID NO: 219) |
| APHRNNA (SEQ ID NO: 20) | WDYDQEA (SEQ ID NO: 70) | QDFNLA (SEQ ID NO: 120) | ALHFETA (SEQ ID NO: 170) | EWGADGA (SEQ ID NO: 220) |
| HHGHNIA (SEQ ID NO: 21) | DWGDPFA (SEQ ID NO: 71) | DNPIDA (SEQ ID NO: 121) | DDPTGFA (SEQ ID NO: 171) | DVIYSHA (SEQ ID NO: 221) |
| HTWHGQA (SEQ ID NO: 22) | DWPEVWA (SEQ ID NO: 72) | FNEHEA (SEQ ID NO: 122) | VAPGLGA (SEQ ID NO: 172) | WHILEEA (SEQ ID NO: 222) |

TABLE 1-continued

Amino acid sequences binding to prion sequences

| | | | | |
|---|---|---|---|---|
| HVFVTWA (SEQ ID NO: 23) | FHDFSEA (SEQ ID NO: 73) | WGADGA (SEQ ID NO: 123) | IFRL1EA (SEQ ID NO: 173) | NPHENFA (SEQ ID NO: 223) |
| THHFYIA (SEQ ID NO: 24) | DTFWDYA (SEQ ID NO: 74) | VIYSHA (SEQ ID NO: 124) | GLERPEA (SEQ ID NO: 174) | HEDNGGA (SEQ ID NO: 224) |
| KLGWG(A/G)A (SEQ ID NO: 25) | WNDLDNA (SEQ ID NO: 75) | HILEEA (SEQ ID NO: 125) | IVVRLWA (SEQ ID NO: 175) | SDSEGPA (SEQ ID NO: 225) |
| GSKKKEA (SEQ ID NO: 26) | ASALVYA (SEQ ID NO: 76) | PHENFA (SEQ ID NO: 126) | WHNPHYA (SEQ ID NO: 176) | EFQEFTA (SEQ ID NO: 226) |
| PLLVVWA (SEQ ID NO: 27) | LINAGGA (SEQ ID NO: 77) | EDNGGA (SEQ ID NO: 127) | LIYKSDA (SEQ ID NO: 177) | QEGDEIA (SEQ ID NO: 227) |
| WLLVGGA (SEQ ID NO: 28) | WESYVTA (SEQ ID NO: 78) | DSEGPA (SEQ ID NO: 128) | EKPIFNA (SEQ ID NO: 178) | DIYAETA (SEQ ID NO: 228) |
| (W/G)QVLVYA (SEQ ID NO: 29) | WSDEGYA (SEQ ID NO: 79) | FQEFTA (SEQ ID NO: 129) | HWSEPAA (SEQ ID NO: 179) | DRVRETA (SEQ ID NO: 229) |
| RRHQRQA (SEQ ID NO: 30) | YRWTGPA (SEQ ID NO: 80) | EGDEIA (SEQ ID NO: 130) | GHNWKEA (SEQ ID NO: 180) | FEEPQWA (SEQ ID NO: 230) |
| LPWTFGA (SEQ ID NO: 31) | YEDQWQA (SEQ ID NO: 81) | IYAETA (SEQ ID NO: 131) | YWHHDDA (SEQ ID NO: 181) | FEGEEFA (SEQ ID NO: 231) |
| IFIIITA (SEQ ID NO: 32) | EWADDNA (SEQ ID NO: 82) | RVRETA (SEQ ID NO: 132) | GYPKENA (SEQ ID NO: 182) | (T/L)FNIHA (SEQ ID NO: 232) |
| P(X)IEPHA (SEQ ID NO: 33) | YEIDYGA (SEQ ID NO: 83) | EEPQWA (SEQ ID NO: 133) | PVYWLYA (SEQ ID NO: 183) | |
| EWGIIWA (SEQ ID NO: 34) | EFGYFDA (SEQ ID NO: 84) | EGEEFA (SEQ ID NO: 134) | FGEHTPA (SEQ ID NO: 184) | |
| GWYIYFA (SEQ ID NO: 35) | WGDEQDA (SEQ ID NO: 85) | (T/L)FNIHA (SEQ ID NO: 135) | FQGTREA (SEQ ID NO: 185) | |
| TLILFHA (SEQ ID NO: 36) | HEEDWAA (SEQ ID NO: 86) | YDW (SEQ ID NO: 136) | TGTNRYA (SEQ ID NO: 186) | |
| FLLSNHA (SEQ ID NO: 37) | FEDFELA (SEQ ID NO: 87) | NYT (SEQ ID NO: 137) | KWATRYA (SEQ ID NO: 187) | |
| WQIRFFA (SEQ ID NO: 38) | TWGIDEA (SEQ ID NO: 88) | SYT (SEQ ID NO: 138) | NSTKFDA (SEQ ID NO: 188) | |
| VLLVFEA (SEQ ID NO: 39) | WDPTDYA (SEQ ID NO: 89) | WAD (SEQ ID NO: 139) | LIYKEEA (SEQ ID NO: 189) | |
| GWVLEIA (SEQ ID NO: 40) | NDKIHTA (SEQ ID NO: 90) | QWG (SEQ ID NO: 140) | EHATYRA (SEQ ID NO: 190) | |
| FLLIDTA (SEQ ID NO: 41) | FEDFFSA (SEQ ID NO: 91) | WGD (SEQ ID NO: 141) | HND (SEQ ID NO: 191) | |
| GFLFKFA (SEQ ID NO: 42) | YEWAEQA (SEQ ID NO: 92) | EYF (SEQ ID NO: 142) | HER (SEQ ID NO: 192) | |
| PWTIYIA (SEQ ID NO: 43) | THVYFLA (SEQ ID NO: 93) | WEH (SEQ ID NO: 143) | HGD (SEQ ID NO: 193) | |
| WH (SEQ ID NO: 44) | (S/T/W)XDFSDA (SEQ ID NO: 94) | LYD (SEQ ID NO: 144) | HSD (SEQ ID NO: 194) | |
| WW (SEQ ID NO: 45) | YRTPNEA (SEQ ID NO: 95) | DYY (SEQ ID NO: 145) | HFD (SEQ ID NO: 195) | |
| LW (SEQ ID NO: 46) | (GIL)RSETA (SEQ ID NO: 96) | FYE (SEQ ID NO: 146) | WND (SEQ ID NO: 196) | |
| WNA (SEQ ID NO: 47) | IHN (SEQ ID NO: 97) | EYY (SEQ ID NO: 147) | YEH (SEQ ID NO: 197) | |
| EFW (SEQ ID NO: 48) | WEY (SEQ ID NO: 98) | YDY (SEQ ID NO: 148) | HWD (SEQ ID NO: 198) | |

TABLE 1-continued

Amino acid sequences binding to prion sequences

| LPW (SEQ ID NO: 49) | DYW (SEQ ID NO: 99) | WDH (SEQ ID NO: 149) | YHD (SEQ ID NO: 199) |
|---|---|---|---|
| YEY (SEQ ID NO: 50) | WDW (SEQ ID NO: 100) | RES(na)NVA (SEQ ID NO: 150) | YDW (SEQ ID NO: 200) |

In some embodiments, the ligand is a peptide of the amino acid sequence of DVR, SYA, AMN31, D4, or YVHEA. In some embodiments, the ligand is a peptide that binds to a prion protein at an affinity that is similar to or higher than that of DVR, SYA, AMN31, D4, or YVHEA. In some embodiments, the ligand is DVR. In other embodiments, the ligand is AMN31. In some embodiments, the peptide ligands are provided in the form of resins (such as bound to resins).

In some embodiments, the ligand is an antibody recognizing a prion protein. Antibodies recognizing prion proteins are known in the art. These include, but are not limited to, monoclonal antibodies 3F4, 6H4, or 16A18. In some embodiments, the antibody is a glycoform specific antibody, such as ICSM-4 and ICSM-10. Suitable antibodies useful for the methods described herein include polyclonal and monoclonal antibodies, single chain antibodies, Fab fragments, and Fv fragments.

In some embodiments, the ligand binds to a specific sequence of a prion protein. For example, in some embodiments, the ligand (such as a peptide ligand or an antibody ligand) binds to any one of the prion protein sequences SEQ ID NOs: 133-146 listed on Table 2.

TABLE 2

Prion amino acid sequences

RYPxQ, x is G, P, or N (SEQ ID NO: 233)

xxYYux, x is G, P, or N, u is R or Q (SEQ ID NO: 234)

RYPGQ (SEQ ID NO: 235)

DRYYRD (SEQ ID NO: 236)

QAYYQR (SEQ ID NO: 237)

QVYYRP (SEQ ID NO: 238)

PHGGGWGQ (SEQ ID NO: 239)

PHGGSWGQ (SEQ ID NO: 240)

PHGGGWSQ (SEQ ID NO: 241)

PHGGGGWSQ (SEQ ID NO: 242)

PHGGGSNWGQ (SEQ ID NO: 243)

PHNPGY (SEQ ID NO: 244)

PHNPSY (SEQ ID NO: 245)

PHNPGY (SEQ ID NO: 246)

In some embodiments, the ligand is a chemical compound. Compounds capable of binding to a prion protein can be found, for example, in PCT Application publication No. WO06/010915, which is incorporated herein in its entirety. In some embodiments, the ligand is a substituted triazine. In some embodiments, the ligand is a compound having formula (I):

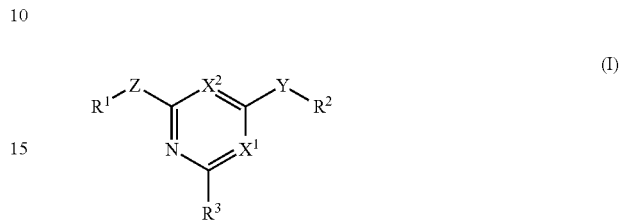

wherein $R^1$ and $R^2$ are the same or different and are each optionally substituted alkyl, optionally substituted cycloalkyl, optionally substituted aryl or optionally substituted heteroaryl groups; $R^3$ is hydrogen or an aryl group substituent or $R^3$ is a solid support optionally attached via a spacer; Z represents an oxygen atom, a sulphur atom or $NR^4$; Y represents an oxygen atom, a sulphur atom or $NR^5$; in which $R^4$ and $R^5$, which may be the same or different, represent hydrogen, optionally substituted alkyl containing 1 to 6 carbon atoms, optionally substituted phenyl, optionally substituted benzyl or optionally substituted β-phenylethyl; and one of $X^1$ and $X^2$ represents a nitrogen atom and the other of $X^1$ and $X^2$ represents a nitrogen atom or $CR^6$, in which $R^6$ represents hydrogen or an aryl group substituent; for the affinity binding of a prion protein.

In some embodiments, the ligand is a compound of formula (II),

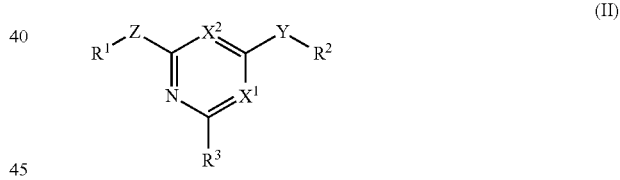

wherein $R^1$ represents a group $-(CH_2)_m-Q^1$, wherein m is from 0 to 7, and $Q^1$ represents $-CR^{11}R^{12}R^{13}$ or $-NR^{11}R^{12}$, in which $R^{11}$, $R^{12}$ and $R^{13}$ independently represent hydrogen, alkyl, cycloalkyl or heterocycloalkyl, or two of $R^{11}$, $R^{12}$ and $R^{13}$, together with the carbon or nitrogen atom to which they are attached, form an optionally substituted cycloalkyl or optionally substituted heterocycloalkyl group; $R^2$ represents a group $-(CH_2)_n-Q^2$, wherein n is from 0 to 7, and $Q^2$ represents $-CR^{21}R^{22}R^{23}$ or $-NR^{21}R^{22}$, in which $R^{21}$, $R^{22}$ and $R^{23}$ independently represent hydrogen, alkyl, cycloalkyl or heterocycloalkyl, or two of $R^{11}$, $R^{12}$ and $R^{13}$, together with the carbon or nitrogen atom to which they are attached, form an optionally substituted cycloalkyl or optionally substituted heterocycloalkyl group, and $R^3$ is hydrogen or an aryl group substituent or $R^3$ is a solid support optionally attached via a spacer; Z represents an oxygen atom, a sulphur atom or $NR^4$; Y represents an oxygen atom, a sulphur atom or $NR^5$; in which $R^4$ and $R^5$, which may be the same or different, represent hydrogen, optionally substituted alkyl containing 1 to 6 carbon atoms, optionally substituted phenyl, optionally substituted benzyl or optionally substituted β-phenylethyl; and one of $X^1$ and $X^2$ represents a nitrogen atom and the other of $X^1$ and $X^2$ represents a nitrogen atom or $CR^6$, in which $R^6$ represents hydrogen or an aryl group substituent; for the affinity binding of a prion protein.

In some embodiments, a)) $X^1$ and $X^2$ are both nitrogen; b) both Z and Y represent $NR^4$, in particular where $R^4$ is hydrogen; c) m is from 0 to 4, more preferably from 0 to 3, and most preferably from 1 to 3; d) $Q^1$ is $—NR^{11}R^{12}$; and $R^{11}$ and $R^{12}$ preferably form, together with the nitrogen atom to which they are attached, a heterocycloalkyl group; e) n is from 0 to 4, more preferably from 0 to 2, and most preferably is 0; and f) $R^{21}$ and $R^{22}$ form, together with the carbon atom or nitrogen atom to which they are attached, a cycloalkyl or heterocycloalkyl group.

In some embodiments, $Q^2$ represents a hydrophobic cycloalkyl or heterocycloalkyl group, especially with ring systems that comprise at least six atoms.

In some embodiments, $Q^1$ represents a heterocycloalkyl group, especially piperidyl, particularly 1-piperidyl, or piperazinyl, particularly 1-piperazinyl.

In some embodiments, the ligand is a compound of formula (III), (III)

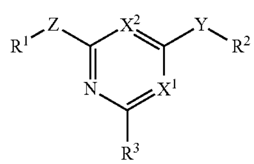

wherein R1 represents an alkylene chain $—(CH_2)_p—CH_3$, wherein p is from 0 to 6, substituted by one or more carboxyl groups and optionally substituted by one or more further alkyl group substituents; $R^2$ represents a group $—(CH_2)_q—Ar$, wherein q is from 0 to 7, and Ar represents an optionally substituted aryl group; and $R^3$ is hydrogen or an aryl group substituent or $R^3$ is a solid support optionally attached via a spacer; Z represents an oxygen atom, a sulphur atom or $NR^4$; Y represents an oxygen atom, a sulphur atom or $NR^5$; in which $R^4$ and $R^5$, which may be the same or different, represent hydrogen, optionally substituted alkyl containing 1 to 6 carbon atoms, optionally substituted phenyl, optionally substituted benzyl or optionally substituted β-phenylethyl; and one of $X^1$ and $X^2$ represents a nitrogen atom and the other of $X^1$ and $X^2$ represents a nitrogen atom or $CR^6$, in which $R^6$ represents hydrogen or an aryl group substituent; for the affinity binding of a prion protein.

In some embodiments, a) $X^1$ and $X^2$ are both nitrogen; b) both Z and Y represent $NR^4$, in particular where $R^4$ is hydrogen; c) p is from 0 to 4, more preferably from 0 to 3; d) $R^1$ is substituted with one or two carboxyl groups, at least one of those carboxyl groups being carried by the terminal carbon atom of the alkylene chain $—(CH_2)_p—CH_3$; e) q is from 0 to 4, more preferably from 0 to 3, and most preferably is 1 or 2; and f) Ar is a monocyclic carbocyclic or heterocyclic aromatic group, optionally substituted by one or more substituents, selected from the group consisting of phenyl, phenoxy, tolyl, chlorobenzyl, methoxybenzyl, fluorobenzyl, pyridyl and indoyl.

In some embodiments, $R^1$ is carboxymethyl, 4-carboxybutyl or 1-(1,3-dicarboxy)propyl.

In some embodiments, Ar is phenyl, 4-hydroxyphenyl or pyridyl, particularly 2-pyridyl.

In some embodiments, $R^3$ is hydrogen or an aryl group substituent or $R^3$ is a solid support optionally attached via a spacer; $X^1$ and $X^2$ are both N; Y and Z both represent NH; m represents 2; $Q^1$ represents piperidyl or piperazinyl; n represents 0 or 2; and $Q^2$ represents 1-piperidyl or adamantyl.

In some embodiments, $R^3$ is hydrogen or an aryl group substituent or $R^3$ is a solid support optionally attached via a spacer; $X^1$ and $X^2$ are both N; Y and Z both represent NH; $R^1$ represents carboxymethyl, 4-carboxybutyl and 1-(1,3-dicarboxy)propyl; q represents 2; and Ar represents phenyl, 2-pyridyl or 4-hydroxyphenyl.

In some embodiments, the ligand is an inorganic compound or component, such as, but not limited to, aluminum (such as aluminum oxide) or silica (such as fused silica). In some embodiments, the inorganic compound is Al203 or SiO2.

In some embodiments, the ligand comprises one or more functional groups. The term "functional group" is used herein to denote chemical groups, subgroups, or substructures that impart characteristic chemical, physical, or physicochemical behaviors to a molecule or a material. Functional groups described herein include, but are not limited to, hydrophilic, such as positively, negatively or uncharged or neutral, or hydrophobic. Amphiphilic or multifunctional functional groups are also envisioned and fall within the scope of the present invention. Functional groups include organic and inorganic functional groups. Preferred functional groups contain amine, phenyl or sulfite groups. A preferred amine group is a primary, secondary, tertiary, or quaternary ammonium ion such as dimethylaminoethyl (DMAE) or trimethylaminoethyl (TMAE).

Other exemplary functional groups include, but are not limited to: —CH2-CHOH—CH2NH2; —C6H5; —(CH2) 3-CII3; —CH2-CH2-NH(C2H5)2; —SO2-CH2-CF3'-CH2-CH2-H(CH3)2; —CH2-CH2-(CH3)3; —SO32-. Additionally useful functional groups include sulfonyl groups and tresyl groups. It is to be understood that functional groups can be inherently present in a ligand, or can be added to the ligand by chemical modification.

In some embodiments, the ligand contains an amino group. These include, for example, amino resin, such as Toyopearl™ Amino-650M, Toyopearl™ Amino-AMN31, TSK-GEL™-Amino 750C, or functional equivalents thereof. In some embodiments, the ligand comprises a phenyl group. These include, for example, TSK-GEL™ Phenyl-5PW or functional equivalent thereof.

In some embodiments, the ligand is a polymeric material, such as chromatographic resins (for example amino resins), that bind with selectivity and specificity to prion proteins. An example of chromatographic resin is PRDT Prion Reduction Resins (ProMetic Biosciences, Ltd, 211 Cambridge Science Park, Milton Road, Cambridge, CB4 0WA, UK). In some embodiments, the polymeric material contains one or more functional groups, such as functional groups described above. In some embodiments, the ligand is a polymeric material having a methacrylate backbone, such as, but not limited to, a commercially available TSK, TOYOPEARL, or FACTOGEL resin (Tosoh Bioscience, Montgomeryville, Pa.).

Other ligands that can be used in methods of the present invention include, for example, ligands that interact with amyloid plaque e.g., Congo:E;Led (Ingrosso, L., et al., Congo Red: Prolongs the Incubation Period in Scrapie-infected Hamsters. Virology 69:506-508 (1995)); 1,4-iodo, 4-deoxy doxorubicin (Tagliavini, F., et al., Effectiveness of Anthracycline Against Experimental Prion Diseases in Syrian Hamsters. Science 276:1119-1122 (1997)); amphotericin 13, porphyrins and phthalocyanines (Priola, S. A., et al., Porphyrin and Phthalocyanine Antiscrapie Compounds, Science 287:1503-1506 (2000)); metals (Stocker et al., Biochemistry, 37, 7185-7193 (1998)); peptides that interact with PrP to form complexes (see U.S. Pat. No. 5,750,361 to Prusiner et al. and Solo, C. et al., Reversion of Prion Protein Conformational Changes in Synthetic p-sheet Breaker Peptides, Lances, 355:192-197 (2000)); heparin and other polysulphated polyanions (Caughey, B., et al., Binding of the Protease-sensitive Form of Prion Protein PrP to Sulphated Glycosaminoglycan and Congo Red, J. Virology 68:2135-2141 (1994)); antibodies (Kascsak, R. J., et. al., Immunodiagnosis of Prion Disease, Immunological Invest. 26:259-268 (1997)); and other proteins, e.g. plasminogen (Fischer, M. B. et al., Binding of Disease-associated Prion Protein to: Plasminogen., Nature 408:479-483 (2000)).

The ligands may be attached to any supporting materials. "Support material" used herein refer to any compound or material which may provide a physical or chemical means of separating the ligand and proteins bound thereto from the rest of the composition. The supporting material may be particulate or non-particulate, soluble or insoluble, porous or non-porous.

Examples of support materials include, but not limited to, naturally occurring polymers, e.g., a polysaccharide such as agarose, alginate, carrageenan, chitin, cellulose, dextran or starch; synthetic polymers such as polyacrylamide, polystyrene, polyacrolein, polyvinyl alcohol, polymethylacrylate, perfluorocarbon; inorganic compounds such as silica, glass, kieselquhr, alumina, iron oxide or other metal oxides, or copolymers consisting of any combination of two or more naturally occurring polymers, synthetic polymers or inorganic compounds. Also contemplated are soluble support materials comprising polymers such as dextran, polyethylene glycol, polyvinyl alcohol or hydrolysed starch which provide affinity-ligand matrix conjugates for use in liquid partitioning In some embodiments, the supporting material is a solid support such as a column, a bead, a membrane, a cartridge, a filter, a dipstick, a microtiter plate, a test tube, solid powder, a cast or extrusion molded module, a mesh, a magnetic particle composite, or any other solid materials. The solid materials may be coated with a substance such as polyethylene, polypropylene, poly(4-methylbutene), polystyrene, polyacrylate, polyethylene terephthalate, rayon, nylon, poly(vinyl butyrate), polyvinylidene difluoride (PVDF), silicones, polyformaldehyde, cellulose, cellulose acetate, nitrocellulose, and the like. Alternatively, substances that form gels, such as proteins (e.g. gelatins), lipopolysaccharides, silicates, agarose and polyacrylamides are used. Polymers such as dextrans, polyalkylene glycols or surfactants, such as phospholipids, long chain (12-24 carbon atoms) alkyl ammonium salts and the like can also be used. The ligands are attached to or dispersed throughout the support materials.

In some embodiments, the supporting material is activated agarose, silica, cellulose, glass, methacrylate, hydroxyethylmethacrylate, polyacrylamide, styrenedivinylbenzene, Hyper D or perfluorocarbons. In some embodiments, the supporting material is a methacrylate material, of the type sold under the trade name Toyopearl (available from Tosoh Bioscience LLC, 156 Keystone Drive, Montgomeryville, Pa. I 18936, USA). WO 97/10887 describes methods of attaching affinity ligands to support matrices, e.g. the use of activating methods, and methods of attaching the affinity ligand to a matrix via a spacer, e.g. by condensation reactions, to form affinity ligand-matrix conjugates.

In some embodiments, the ligands and/or supporting materials are reusable. In some embodiments, the ligands and/or supporting materials for single use only.

The prion binding capacity of a ligand can be evaluated by determining the infectious titre in a ligand. For example, a dilution series of a reference stock is prepared and tested in the standard Western blot assay. The titres observed from the reference stock are compared with the corresponding titres observed in a bioassay. The Western blot titres can then be converted into infectious titres using the formula: Titre$_{[Bioassay]}$=Titre$_{[WesternBlot]}$+(intercept of a linear regression analysis)/(slope of a linear regression analysis). Once the infectious titre per ml is calculated, the total prion protein bound to the column can be determined. The capacity of the prion binding of a ligand is determined using the amount of prion protein observed directly bound to the ligand. In some embodiments, the prion binding capacity of a ligand is at least about 2.0, 2.5, 3.0, 3.5, 4.0, 4.5, 5.0, 5.5, 6.0, 6.5, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.5, or 10.0 log$_{10}$ ID$_{50}$ per ml of ligand. In some embodiments, the prion binding capacity of a ligand is at least about $10^2$, $10^3$, $10^4$, $10^5$, $10^6$, $10^7$, or $10^8$ ID$_{50}$ per ml of ligand.

Method of Making Nanoparticles

Methods of making compositions containing albumins and substantially water insoluble pharmacologically active agents are known in the art. For example, nanoparticles containing substantially water insoluble pharmacologically active agents and albumins can be prepared under conditions of high shear forces (e.g., sonication, high pressure homogenization, or the like). These methods are disclosed in, for example, U.S. Pat. Nos. 5,916,596; 6,506,405; 6,749,868, and 6,537,579 and also in U.S. Pat. Pub. Nos. 2005/0004002 and 2007/0082838, and PCT Publication WO99/00113, which are each hereby incorporated by reference in their entireties.

In one exemplary embodiment, the substantially water insoluble pharmacologically active agent (e.g., paclitaxel) is dissolved in an organic solvent. Suitable organic solvents include, for example, ketones, esters, ethers, chlorinated solvents, and other solvents known in the art. For example, the organic solvent can be methylene chloride. In some embodiments, the organic solvent can be a mixture of a water immiscible solvent (such as chloroform) and a water miscible solvent (such as a water miscible alcohol solvent, such as chloroform/methanol, chloroform/ethanol, chloroform/propanol, or chloroform/t-butanol (for example with a ratio (v/v) of about any of 1:9, 1:8, 1:7, 1:6, 1:5, 1:4, 1:3, 1:2, 1:1, 2:1, 3:1, 4:1, 5:1, 6:1, 7:1, 8:1, or 9:1 or with a ratio (v/v) of about any of 3:7, 5:7, 4:6, 5:5, 6:5, 8:5, 9:5, 9.5:5, 5:3, 7:3, 6:4, or 9.5:0.5). The solution is added to an albumin (e.g., human serum albumin). The mixture is subjected to high pressure homogenization (e.g., using standard homogenization devices). The emulsion may be cycled through the high pressure homogenizer for between about 2 to about 100 cycles, such as about 5 to about 50 cycles or about 8 to about 20 cycles (e.g., about any of 8, 10, 12, 14, 16, 18 or 20 cycles). The organic solvent can then be removed by evaporation utilizing suitable equipment known for this purpose, including, but not limited to, rotary evaporators, thin file evaporators, falling film evaporators, wiped film evaporators, spray driers, and the like. The solvent may be removed, for example, at reduced pressure (such as at about any of 5 mm Hg, 10 mm Hg, 15 mm Hg, 20 mm Hg, 25 mm Hg, 30 mm Hg, 40 mm Hg, 50 mm Hg, 100 mm Hg, 200 mm Hg, or 300 mm Hg). The amount of time used to remove the solvent under reduced pressure may be adjusted based on the volume of the formulation. For example, for a formulation produced on a 300 mL scale, the solvent can be removed at about 1 to about 300 mm Hg (e.g., about any of 5-100 mm Hg, 10-50 mm Hg, 20-40 mm Hg, or 25 mm Hg) for about 1 to about 120 minutes, including about 5 to about 60 minutes (e.g., about any of 7, 8, 9, 10, 11, 12, 13, 14, 15 16, 18, 20, 25, or 30 minutes).

If desired, albumin solution (such as prion-removed albumin solution) may be added to the dispersion to adjust the albumin to drug (e.g., paclitaxel) ratio or to adjust the concentration of the taxane (e.g., paclitaxel) in the dispersion. For example, albumin solution (e.g., 25% w/v) can be added to adjust the albumin to substantially water insoluble pharmacologically active agent (e.g., paclitaxel) ratio to about any of 18:1, 15:1 14:1, 13:1, 12:1, 11:1, 10:1, 9:1, 8:1, 7.5:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, or 1:18. For example, albumin solution (e.g., 25% w/v) or another solution is added to adjust the concentration of the substantially water insoluble pharmacologically active agent (e.g., paclitaxel) in the dispersion to about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml. The dispersion may be individually or serially filtered through one or more filters, such as 1.2 µm, 0.8 µm, 0.45 µm, and 0.22 µm filters; combinations of two or more thereof, or the combination with any other filters known in the art.

If desired, a second therapy (e.g., one or more compounds useful for treating cancer), an antimicrobial agent (such as citrate or edetate), sugar (such as sucrose), and/or stabilizing agent can also be included in the composition. This additional agent can either be admixed with the substantially water insoluble pharmacologically active agent (e.g., paclitaxel) and/or the albumin during preparation of the composition, or added after the nanoparticle composition is prepared. In some embodiments, the agent is admixed with the nanoparticle composition prior to lyophilization. In some embodiments, the agent is added to the lyophilized composition. In some embodiments when the addition of the agent changes the pH of the composition, the pH in the composition are generally (but not necessarily) adjusted to a desired pH. Exemplary pH values of the compositions include, for example, in the range of about 5 to about 8.5. In some embodiments, the pH of the composition is adjusted to no less than about 6, including for example no less than any of about 6.5, 7, or 8 (e.g., about 8).

As discussed below in more detail, the prion-removal process can be carried out concurrently with the manufacturing process. For example, the prion-removal process can be carried out after the mixture of albumin and substantially water insoluble pharmacologically active agent is formed and prior to subjecting the mixture to the high shear condition. In some embodiments, the prion-removal process can be carried out after the mixture has been subjected to the high shear condition and prior to the removal of the organic solvent. In some embodiments, the prion-removal process is carried out after the removal of the organic solvent. In some embodiments, additional albumin is added to the post-evaporation suspension prior to the prion-removal process. In some embodiments, the prion-removal process is carried out under a sterile condition. In some embodiments, the prion-removal process is carried out by using a cartridge which simultaneously sterile filters the composition.

Method of Removing Prions from Nanoparticle Compositions or Intermediate Compositions The present invention in one aspect provides methods comprising removing prion proteins from a nanoparticle composition, such as nanoparticle compositions formed by methods described above. In another aspect there are provided methods of removing prion proteins from intermediate compositions generated during the nanoparticle manufacture process (hereinafter referred to as "the intermediate composition").

Generally, the methods comprise contacting a composition comprising albumin and a substantially water insoluble pharmacologically active agent with a ligand capable of binding to a prion protein, and removing the ligand and protein bound thereto from the nanoparticle composition. This process can be repeated one or more times, with the same or a different ligand. Two or more ligands can also be used simultaneously during the prion removal process.

In some embodiments, the nanoparticle composition or the intermediate composition has a prion infectivity of about 100 IU-ic/ml, 90 IU-ic/ml, 50 IU-ic/ml, or 10 IU-ic/ml.

During the prion-removal process, the ligand is brought into contact with the nanoparticle composition or intermediate composition and allowed to bind to prion proteins in the nanoparticle composition or the intermediate composition. Conditions suitable for the binding can be determined and optimized to facilitate binding of the ligand to a prion protein based on the nature of the ligand and its binding specificity to the prion protein. In some embodiments, the binding is carried out at a temperature of about 0° C. to about 39° C., including for example about 20° C. to about 25° C. The binding can be carried out at pH of about 4 to about 10, including for example about 5 to about 9, about 6 to about 8, about 6.8 to about 7.5, about 6.9 to about 7.4, or about 7. Optionally, blocking agents can be used to reduce non-specific binding to the ligand.

After the contacting step, the ligand and proteins bound thereto are removed from the rest of the composition. The removal can be carried out in a variety of ways, depending on the nature of the ligand and the supporting material (if any) used to facilitate the separation. For example, the ligand and proteins bound thereto can be separated out by chromatography, such as, but not limited to, thin-layer, column and batch chromatography; solid support and membrane separation; reactor separation; magnetic separation, immunoseparation; and colloidal separation.

In some embodiments, ligand may be immobilized on a support such as a bead or a membrane, which in turn is allowed to contact the nanoparticle composition or the intermediate composition. Ligand-immobilized support is allowed to contact the nanoparticle composition or the intermediate composition under a condition sufficient to cause formation of a prion-ligand complex. The solid phase is then separated from the composition, thereby removing the prion protein bound to the ligand from the sample. For example, in one exemplary embodiment, the ligands are immobilized to a column, such as a chromatography column, a sample (such as the nanoparticle composition) is then passed through the column either due to the force of gravity or under pressure, such as in a high pressure liquid chromatography column. Prion proteins in the sample will bind to the ligand immobilized on the column, and the sample passing through can be collected. This process can repeat several times to achieve the desired result.

The flow rate of a sample (such as nanoparticle composition or intermediate composition) in a column can be adjusted to maximize the binding of the ligand and the prion proteins in a sample. In some embodiments, the binding is carried out at a flow rate of about 0.1 ml per minute to about 5.0 ml per minute, about 0.1 ml per minute to about 2.5 ml per minute, about 0.1 ml per minute to about 0.25 ml per minute, about 0.25 per minute to about 0.5 ml per minute, about 0.5 ml per minute to about 1.0 ml per minute, about 1.0 ml per minute to about 1.5 ml per minute, about 1.5 ml per minute to about 2.0 ml per minute, about 2.0 ml per minute to about 2.5 ml per minute, about 2.5 ml per minute to about 3.0 ml per minute, about 3.0 ml per minute to about 3.5 ml per minute, about 3.5 ml per minute to about 4.0 ml per minute, about 4.0 ml per minute to about 4.5 ml per minute, or about 4.5 ml per minute to about 5.0 ml per minute, including for example about 0.1 ml per minute, 0.25 ml per minute, 0.5 ml per minute, 1.0 ml per minute, 1.5 ml per minute, 1.7 ml per minute, 1.8 ml per minute, 1.9 ml per minute, 2.0 ml per minute, 2.1 ml per minute, 2.3 ml per minute, 2.5 ml per minute, 2.7 ml per minute, 3.0 ml per minute, 3.5 ml per minute, 4.0 ml per minute, 4.5 ml per minute, or 5.0 ml per minute. In some embodiments, the flow rate is at least about 10 ml per minute, such as at least about any of 20 ml per minute, 30 ml per minute, 40 ml per minute, 50 ml per minute.

The total flow-through volume or total flow-through time during a binding process can also be adjusted to maximize the binding of the ligand and the prion proteins in a sample (such as nanoparticle composition or the intermediate composition). In some embodiments, the total flow-through volume is about 50 times to about 1000 times of the column volume, including for example about 50 times to about 500 times of the column volume, about 100 times to about 600 times of the column volume, or about 200 times to about 800 times of the column volume. In some embodiments, the total flow-through volume is about 100 times of the column volume. In other embodiments, the total flow-through volume is about 500 times of the column volume. In some embodiments, the total flow-through time is about 1 hour to about 30 hours, including for example about 2 hours to about 25 hours, about 3 hours to about 20 hours, or about 3 hours to about 17 hours. In some embodiments, the total flow-through time is any of about 3 hours, 4 hours, 6 hours, 8 hours, 10 hours, 12 hours, 14 hours, 16 hours, 17 hours, 18 hours, 19 hours, or 20 hours. In some embodiments, the total flow through time is more than about 24 hours. In some embodiments, the total flow through time is less than about 8, including for example any of 7, 6, 5, 4, 3, 2, 1, or 0.5 hours.

Alternatively, the ligand can first be brought into contact with the nanoparticle composition or the intermediate composition, under a condition sufficient to cause formation of a prion-ligand complex. The prion-ligand complex is then subsequently removed by using a column, such as an affinity-based chromatography. To facilitate the separation, the ligand may be conjugated to a binding partner so that the ligand/prion complex can be removed by using an affinity column containing a molecule that recognizes the binding partner.

In addition to batch or column chromatography, a variety of configurations, modifications and variations of the use of the ligands for binding prion proteins are also envisioned. Such variations and modifications include, but are not limited to: batch processes, continuous processes, moving bed chromatography processes; low, medium, or high pressure processes; or small, medium or large scale processes. In some embodiments, the ligands are on a membrane, fibers bead, impregnated into a non-woven mesh, or coating fibers contained within a filter housing.

In some embodiments, the removal step does not significantly result in yield loss and/or change in the property and/or stability of the albumin. For practical purposes, the recovery of the albumin in its original biological state should be substantially maintained at least to a level in excess of 50%, including for example 80%, or 90%, or more. In some embodiments, the recovery rate of albumin from the prion process is higher than any of about 80%, 90%, 95%, or 99%. In some embodiments, the concentration of albumin in the nanoparticle composition is adjusted or controlled prior to the prion removal step in order to minimize non-specific binding and loss of albumin during the process. For example, the concentration of albumin can be in the range of about 1% to about 50%, about 5% to about 25%, about 5% to about 30%, about 5% to about 40%, about 5% to about 10%, about 10% to about 15%, about 15% to about 20%, about 20% to about 25%, about 25% to about 30% etc., including for example about 5%, 10%, 15%, 20%, 25%, or 30% albumin.

In some embodiments, the removal step does not significantly result in yield loss and/or change in the property and/or stability of the nanoparticles in the composition.

In some embodiments, the removal step does not significantly result in yield loss and/or change in the property or loading of the substantially water insoluble pharmacologically active agent in the composition.

In some embodiments, the removal step does not significantly result in change in the ratio of albumin to the substantially water insoluble pharmacological agent in the composition.

The prion-removed composition can be analyzed to determine the clearance rate of the prion removal process. The ligand with bound prion proteins may also be analyzed (directly or after elution) to determine the clearance rate.

The removal of prion protein can be determined based on reduction in the prion protein level and/or a reduction in infectivity. In some embodiments, at least about 50%, including for example at least about 60%, 70%, 80%, 90%, 95%, 99%, or 100% of the prion proteins are removed from the nanoparticle composition. In some embodiments, the infectivity of the post-removal albumin composition is at least about 10×, 20×, 30×, 40×, 50×, 80×, 100×, 200×, 500×, 1000×, $10^4$×, $10^5$×, $10^6$× less than that of the nanoparticle composition.

In some embodiments, serial infectivity is used to determine the clearance rate of the prion removal process. Serial dilutions of a samples are made and dilutions are examined for infectious activity, for example in an assay animal. The dilution at which half of the animals become infected is the infectious titer. For example, if a 5 fold dilution is required, the sample may be defined as having 5 logs of infectivity. By comparing the log infectivity of the nanoparticle composition and that of the post-removal nanoparticle composition, one can determine the clearance rate of the prion removal process. In some embodiments, the prion removal method results in a reduction of any one of 1, 1.1, 1.2, 1.3, 1.4, 1.5, 1.6, 1.7, 1.8, 1.9, 2, 3, or 4, 5, 6, 7, 8, 9, or 10 logs of infectivity.

In some embodiments, the clearance rate of the prion-removal process is determined based on spiking experiments with infectious materials by following steps described herein for the prion-removal method. Suitable spiking agents include, but are not limited to, brain homogenates, microsomes, caveolae-like domains, purified PrPsc, and prion fibrils. In some embodiments, the spiking agent is detergent solubilized (such as sarkosyl solubilized). In some embodiments, the spiking ratio in the composition is in the range of about 0.001% to about 5%, about 0.001% to about 0.25%, about 0.001% to about 0.1%, about 0.001% to about 0.005%, about 0.005% to about 0.075%, about 0.075% to about 0.01%, about 0.01% to about 0.1%, about 0.1% to about 0.5%, about 0.5% to about 0.75%, about 0.75% to about 1%, about 1% to about 2%, about 2% to about 3%, or about 3% to about 5%, including for example about 0.001%, 0.005%, 0.075%, 0.01%, 0.1%, 0.5%, 0.75%, 1%, 2%, 3%, or 5%.

In some embodiments, the reduction factors (RF) is used to determine the clearance rate of the prion removal process. The RF can be calculated using the formula:

$$RF = (V_1 \times T_1)/(V_2 \times T_2)$$

or $$Log_{10}[RF] = [Log_{10}(V_1) + Log_{10}(T_1)] - [Log_{10}(V_2) + Log_{10}(T_2)].$$

Wherein $V_1$ and $T_1$ are the volume and titre of the initial albumin composition, respectively, and $V_2$ and $T_2$ are the volume and titre of the post-removal albumin composition. Reduction factors can be rounded to 1 decimal place after the final calculation. In some embodiments, a reduction factor of at least about 1.0, 1.5, 2.0, 2.5, 3.0, 3.5, 4.0, 4.5, 5.0, 5.5, 6.0, 6.5, 7.0, 7.5, or 8.0 $log_{10}$ infectivity of the prion proteins is removed from the initial albumin composition. For example, the prion protein can be removed by a reduction factor of greater than or equal to 2.5 $log_{10}$ in a 0.5% sarkosyl solubilized fraction spiked into a 20% albumin composition. As another example, the prion protein can also be removed by a reduction factor of greater than or equal to 2.0 $\log_{10}$ in a 0.5% sarkosyl solubilized fraction spiked into a 25% albumin composition.

The removal of prions can be evaluated by standard Western blot analysis. For example, the post-binding ligands can first be treated with Proteinase K, which digests all PrPc but not PrPsc. The digest is then run on SDS gel and transblotted to a sheet of nitrocellulose or PVDF membrane. The separated PrPsc bands are then visualized using 3F4 or 6H4. 3F4 reacts with residues 109-112 PrP from humans, hamsters, and felines. In one exemplary embodiment, incubation was carried out at a concentration of 0.6 ug/ml for a minimum of one hour, after which excess antibody was washed away and the membranes incubated with a rabbit anti-mouse horse-radish peroxidase conjugate (1:1000 dilution) for a minimum of one hour. After extensive washing with TTBS, the membranes were developed using enhanced chemiluminescence. In some embodiments, the removal of prion proteins is evaluated according to the Guideline for the Investigation of Manufacturing Processes for Plasma-Derived Medicinal Products with Regard to vCJD Risk (CPMP5136/03).

Also contemplated herein are compositions made during the prion removal process. Thus, in some embodiments, there is provided a composition comprising nanoparticles comprising albumin and a substantially water insoluble pharmacologically active agent, further comprising a ligand capable of binding to a prion protein. In some embodiments, there is provided a mixture comprising nanoparticle comprising albumin and a substantially water insoluble pharmacologically active agent, and a ligand capable of binding to a prion protein attached to a support material, such as one or more supporting materials described herein. In some embodiments, there is provided a column loaded with a composition comprising nanoparticles comprising albumin and a substantially water insoluble pharmacologically active agent, wherein the column comprises a ligand capable of binding to a prion protein. In some embodiments, there is provided a composition comprising nanoparticles comprising albumin and a substantially water insoluble pharmacologically active agent and a resin comprising a ligand capable of binding to a prior protein. For example, in some embodiments, there is provided a composition comprising nanoparticles comprising albumin and a substantially water insoluble pharmacologically active agent and a DVR resin. In some embodiments, there is provided a composition comprising nanoparticles comprising albumin and a substanti8ally water insoluble pharmacologically active agent and a PRDT resin.

In some embodiments, there is provided a composition comprising a mixture of an aqueous albumin solution and a substantially water insoluble pharmacologically active agent dispersed in an organic solvent, further comprising a ligand capable of binding to a prion protein. In some embodiments, there is provided a composition comprising a mixture of an aqueous albumin solution and a substantially water insoluble pharmacologically active agent dispersed in an organic solvent, and a ligand capable of binding to a prion protein attached to a support material, such as one or more supporting materials described herein. In some embodiments, there is provided a column loaded with a composition comprising a mixture of an aqueous albumin solution and a substantially water insoluble pharmacologically active agent dispersed in an organic solvent, wherein the column comprises a ligand capable of binding to a prion protein.

Also provided are compositions made by methods described herein. The composition in some embodiments is bioequivalent to a composition not subject to prion-removal process.

Nanoparticle Compositions

The nanoparticle compositions described herein comprise nanoparticles comprising (in various embodiments consisting essentially of) albumin and a substantially water insoluble pharmacologically active agent (such as paclitaxel). Nanoparticles of poorly water soluble drugs (such as taxane) have been disclosed in, for example, U.S. Pat. Nos. 5,916,596; 6,506,405; 6,749,868, and 6,537,579 and also in U.S. Pat. Pub. Nos. 2005/0004002 and 2007/0082838, and PCT Patent Application WO08/137,148, the content of each of which is incorporated herein in their entirety.

In some embodiments, the composition comprises nanoparticles with an average or mean diameter of no greater than about 1000 nanometers (nm), such as no greater than about any of 900, 800, 700, 600, 500, 400, 300, 200, and 100 nm. In some embodiments, the average or mean diameters of the nanoparticles is no greater than about 200 nm. In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 to about 400 nm. In some embodiments, the average or mean diameter of the nanoparticles is about 40 to about 200 nm. In some embodiments, the nanoparticles are sterile-filterable.

In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of all the nanoparticles in the composition have a diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of all the nanoparticles in the composition fall within the range of about 20 to about 200 nm, including for example any one of about 30 to about 180 nm, and any one of about 40 to about 150, about 50 to about 120, and about 60 to about 100 nm.

In some embodiments, at least about 5% (including for example at least about any one of 10%, 15%, 20%, 25%, 30%, 40%, 50%, 60%, 70%, 80%, or 90%) of the albumin in the nanoparticle portion of the composition are crosslinked (for example crosslinked through one or more disulfide bonds).

In some embodiments, the nanoparticles comprise the substantially water insoluble pharmacologically active agent (such as paclitaxel) coated with an albumin (e.g., human serum albumin). In some embodiments, the composition comprises substantially water insoluble pharmacologically active agent in non-nanoparticle form, wherein at least about any one of 50%, 60%, 70%, 80%, 90%, 95%, or 99% of the substantially water insoluble pharmacologically active agent in the composition are in nanoparticle form. In some embodiments, the substantially water insoluble pharmacologically active agent in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of substantially water insoluble pharmacologically active agent that is substantially free of polymeric materials (such as polymeric matrix).

In some embodiments, the composition comprises albumin in both nanoparticle and non-nanoparticle portions of the composition, wherein at least about any one of 50%, 60%, 70%, 80%, 90%, 95%, or 99% of the albumin in the composition are in the non-nanoparticle portion of the composition.

In some embodiments, the nanoparticle composition is substantially free (such as free) of surfactants (such as Cremophor®, Tween 80, or other organic solvents used for the administration of substantially water insoluble pharmacologically active agents). In some embodiments, the nanoparticle composition contains less than about any one of 20%, 15%, 10%, 7.5%, 5%, 2.5%, 1% or less organic solvent. In some embodiments, the weight ratio of albumin and substantially water insoluble pharmacologically active agent in the nanoparticle composition is about 18:1 or less, such as about 15:1 or less, for example about 10:1 or less. In some embodiments, the weight ratio of albumin and substantially water insoluble pharmacologically active agent in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of albumin and substantially water insoluble pharmacologically active agent in the nanoparticle portion of the composition is about any one of 1:2, 1:3, 1:4, 1:5, 1:10, 1:15, or less. In some embodiments, the weight ratio of the albumin (such as human serum albumin) and the substantially water insoluble pharmacologically active agent in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, or about 1:1.

In some embodiments, the nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises human serum albumin Human serum albumin (HSA) is a highly soluble globular protein of Mr 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock and in conjunction with exchange transfusion in the treatment of neonatal hyperbilirubinemia. Other albumins are contemplated, such as bovine serum albumin. Use of such non-human albumins could be appropriate, for example, in the context of use of these compositions in non-human mammals, such as the veterinary (including domestic pets and agricultural context).

Human serum albumin (HSA) has multiple hydrophobic binding sites (a total of eight for fatty acids, an endogenous ligand of HSA) and binds a diverse set of substantially water insoluble pharmacologically active agents, especially neutral and negatively charged hydrophobic compounds. Two high affinity binding sites have been proposed in subdomains IIA and IIIA of HSA, which are highly elongated hydrophobic pockets with charged lysine and arginine residues near the surface which function as attachment points for polar ligand features.

The albumin in the composition generally serves as a carrier for the substantially water insoluble pharmacologically active agent, i.e., the albumin in the composition makes the substantially water insoluble pharmacologically active agent more readily suspendable in an aqueous medium or helps maintain the suspension as compared to compositions not comprising an albumin. This can avoid the use of toxic solvents (or surfactants) for solubilizing the substantially water insoluble pharmacologically active agent, and thereby can reduce one or more side effects of administration of the substantially water insoluble pharmacologically active agent into an individual (such as a human). Thus, in some embodiments, the composition described herein is substantially free (such as free) of surfactants, such as Cremophor (including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is administered to the individual.

The amount of albumin in the composition described herein will vary depending on other components in the composition. In some embodiments, the composition comprises an albumin in an amount that is sufficient to stabilize the substantially water insoluble pharmacologically active agent in an aqueous suspension, for example, in the form of a stable colloidal suspension (such as a stable suspension of nanoparticles). In some embodiments, the albumin is in an amount that reduces the sedimentation rate of the substantially water insoluble pharmacologically active agent in an aqueous medium. For particle-containing compositions, the amount of the albumin also depends on the size and density of nanoparticles of the substantially water insoluble pharmacologically active agent.

A substantially water insoluble pharmacologically active agent is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the albumin is present in an amount that is sufficient to stabilize the substantially water insoluble pharmacologically active agent in an aqueous suspension at a certain concentration. For example, the concentration of the substantially water insoluble pharmacologically active agent in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the substantially water insoluble pharmacologically active agent is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the albumin is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 25% (w/v), about 30% (w/v), about 40% (w/v), or about 50% (w/v)) of albumin. In some embodiments, the composition, in liquid form, comprises about 0.5% to about 5% (w/v) of albumin.

In some embodiments, the weight ratio of albumin, e.g., albumin, to the substantially water insoluble pharmacologically active agent in the nanoparticle composition is such that a sufficient amount of substantially water insoluble pharmacologically active agent binds to, or is transported by, the cell. While the weight ratio of albumin to substantially water insoluble pharmacologically active agent will have to be optimized for different albumin and substantially water insoluble pharmacologically active agent combinations, generally the weight ratio of albumin, e.g., albumin, to substantially water insoluble pharmacologically active agent (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the albumin to substantially water insoluble pharmacologically active agent weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less.

In some embodiments, the albumin allows the composition to be administered to an individual (such as human) without significant side effects. In some embodiments, the albumin is in an amount that is effective to reduce one or more side effects of administration of the substantially water insoluble pharmacologically active agent to a human. The term "reducing one or more side effects of administration of the substantially water insoluble pharmacologically active agent" refers to reduction, alleviation, elimination, or avoidance of one or more undesirable effects caused by the substantially water insoluble pharmacologically active agent, as well as side effects caused by delivery vehicles (such as solvents that render the substantially water insoluble pharmacologically active agents suitable for injection) used to deliver the substantially water insoluble pharmacologically active agent. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with substantially water insoluble pharmacologically active agents can be reduced.

In some embodiments, the composition comprises Abraxane® (or Nab-paclitaxel). In some embodiments, the composition is Abraxane® (or Nab-paclitaxel). Abraxane® is a formulation of paclitaxel stabilized by human albumin USP, which can be dispersed in directly injectable physiological solution. When dispersed in a suitable aqueous medium such as 0.9% sodium chloride injection or 5% dextrose injection, Abraxane™ forms a stable colloidal suspension of paclitaxel. The mean particle size of the nanoparticles in the colloidal suspension is about 130 nanometers. Since HSA is freely soluble in water, Abraxane™ can be reconstituted in a wide range of concentrations ranging from dilute (0.1 mg/ml paclitaxel) to concentrated (20 mg/ml paclitaxel), including for example about 2 mg/ml to about 8 mg/ml, about 5 mg/ml.

Substantially Water Insoluble Pharmacologically Active Agent

The compositions described herein comprise substantially water insoluble pharmacologically active agents. For example, the solubility in water of the poorly water soluble agent at about 20-25° C. may be less than about 10 mg/ml, including for example less than about any of 5, 2, 1, 0.5, 0.2, 0.1, 0.05, 0.02, or 0.01 mg/ml. In some embodiments, the substantially water insoluble pharmacologically active agent is a solid. In some embodiments, the substantially water insoluble pharmacologically active agent is a liquid. Substantially water insoluble pharmacologically active agents described herein can be, for example, pharmaceutical agent, diagnostic agent, or an agent of nutritional value.

Suitable pharmaceutical agents include, but are not limited to, anticancer or antineoplastic agents, antimicrotubule agents, immunosuppressive agents, anesthetics, hormones, agents for use in cardiovascular disorders, antiarrhythmics, antibiotics, antifungals, antihypertensives, antiasthmatics, anti-inflammatory agents, anti-arthritic agents, vasoactive agents, analgesics/antipyretics, antidepressants, antidiabetics, antifungal agents, anti-inflammatories, antianxiety agents, immunosuppressive agents, antimigraine agents, sedatives, antianginal agents, antipsychotic agents, antimanic agents, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antiviral agents, antimicrobials, anti-infectives, bronchodialators, hormones, hypoglycemic agents, hypolipidemic agents, antiulcer/antireflux agents, antinauseants/antiemetics, and oil-soluble vitamins (e.g., vitamins A, D, E, K, and the like).

In some embodiments, the substantially water insoluble pharmacologically active agent is any one of the following: a tyrosine kinase inhibitor, a series/threonine kinase inhibitor, a hedgehog inhibitor, a topoisomerase inhibitor, an in inhibitor of microtubule assembly, an inhibitor of the AKT kinase pathway, a proteasome inhibitor, an antimetabolite, and a platinum-based agent.

In some embodiments, the substantially water insoluble pharmacologically active agent is an antineoplastic agent. In some embodiments, the substantially water insoluble pharmacologically active agent is a chemotherapeutic agent.

Suitable substantially water insoluble pharmacologically active agents include, but are not limited to, taxanes (such as paclitaxel, docetaxel, ortataxel and other taxanes), epothilones, camptothecins, colchicines, geladanamycins, amiodarones, thyroid hormones, amphotericin, corticosteroids, propofol, melatonin, cyclosporine, rapamycin (sirolimus) and derivatives, tacrolimus, mycophenolic acids, ifosfamide, vinorelbine, vancomycin, gemcitabine, SU5416, thiotepa, bleomycin, diagnostic radiocontrast agents, and derivatives thereof. Other substantially water insoluble pharmacologically active agents that are useful in the inventive compositions are described in, for example, U.S. Pat. Nos. 5,916,596, 6,096,331, 6,749,868, and 6,537,539. Additional examples of substantially water insoluble pharmacologically active agents include those compounds which are poorly water soluble and which are listed in the "Therapeutic Category and Biological Activity Index" of The Merck Index (12$^{th}$ Edition, 1996).

In some embodiments, the substantially water insoluble pharmacologically active agent is any of (and in some embodiments selected from the group consisting of) paclitaxel, docetaxel, CY196, ortataxel or other taxane or taxane analog, 17-allyl amino geldanamycin (17-AAG), 18-derivatized geldanamycin, camptothecin, propofol, amiodarone, cyclosporine, epothilone, radicicol, combretastatin, rapamycin, amphotericin, liothyronine, epothilone, colchicine, thiocolchicine and its dimers, thyroid hormone, vasoactive intestinal peptide, corticosteroids, melatonin, tacrolimus, mycophenolic acids, epothilones, radicicols, combretastatins, and analog or derivative thereof. In some embodiments, the substantially water insoluble pharmacologically active agent is any of (and in some embodiments selected from the group consisting of) paclitaxel, docetaxel, CY196, ortataxel or other taxanes, geldanamycin, 17-allyl amino geldanamycin, thiocolchicine and its dimers, rapamycin, cyclosporine, epothilone, radicicol, and combretastatin. In some embodiments, the substantially water insoluble pharmacologically active agent is rapamycin. In some embodiments, the substantially water insoluble pharmacologically active agent is 17-AAG. In some embodiments, the substantially water insoluble pharmacologically active agent is a thiocolchicine dimer (such as IDN5404). In some embodiments, the substantially water insoluble pharmacologically active agent is a taxane. In some embodiments, the substantially water insoluble pharmacologically active agent is paclitaxel. In some embodiments, the substantially water insoluble pharmacologically active agent is docetaxel. In some embodiments, the substantially water insoluble pharmacologically active agent is CY196.

In some embodiments, the substantially water insoluble pharmacologically active agent is a taxane or derivative thereof, which includes, but is not limited to, paclitaxel, docetaxel and IDN5109 (ortataxel), or a derivative thereof. In some embodiments, the composition comprises a non-crystalline and/or amorphous taxane (such as paclitaxel or a derivative thereof). In some embodiments, the composition is prepared by using an anhydrous taxane (such as anhydrous docetaxel or a derivative thereof). Anhydrous docetaxel has been shown to produce more stable formulation than can be made with a hydrated docetaxel such as docetaxel trihydrate or hemi-hydrate.

Other Components in the Nanoparticle Compositions

The nanoparticles described herein can be present in a composition that includes other agents, excipients, or stabilizers. For example, to increase stability by increasing the negative zeta potential of nanoparticles, certain negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596 and 6,096,331). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Method of Using Prion-Free Nanoparticle Compositions

Also provided are methods of using the prion-free compositions described herein. For example, in some embodiments, there is provided a method of administering a composition comprising nanoparticles comprising albumin and a substantially water insoluble pharmacologically active agent, wherein the composition is substantially free of a prion protein. In some embodiments, there is provided a method of treating a disease (such as cancer) comprising administering an effective amount of a composition comprising nanoparticles comprising albumin and a substantially water insoluble pharmacologically active agent, wherein the composition is substantially free of a prion protein.

In some embodiments, there is provided a method of administering a composition comprising nanoparticles comprising albumin and a substantially water insoluble pharmacologically active agent, wherein the albumin in the composition was obtained by a method comprising a prion-removal process, said prion-removal process comprising contacting an initial albumin composition with a ligand capable of binding to a prion protein. In some embodiments, the prion removal process further comprises removing said ligand and proteins bound thereto from said albumin composition. In some embodiments, there is provided a method of treating a disease (such as cancer) in an individual comprising administering to the individual an effective amount of composition comprising nanoparticles comprising albumin and a substantially water insoluble pharmacologically active agent, wherein the albumin in the composition was obtained by a method comprising a prion-removal process, said prion removal process comprising contacting an initial albumin composition with a ligand capable of binding to a prion protein.

In some embodiments, the individual has vCJD. In some embodiments, the individual has already been infected with a prion protein. In some embodiments, the individual is suspected of having vCJD or being infected with a prion protein. In some embodiments, the individual is an asymptomic carrier of a prion protein. In some embodiments, the individual has received blood transfusion at least once. In some embodiments, the individual is at least 60 years old, such as at least about 65, 70, or 75 years old. In some embodiments, the individual is immunity compromised. In some embodiments, the individual is a cancer patient.

The term "effective amount" used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth). In some embodiments, an effective amount is an amount sufficient to delay development. In some embodiments, an effective amount is an amount sufficient to prevent occurrence and/or recurrence. An effective amount can be administered in one or more administrations.

Cancers to be treated by compositions described herein (such as a composition comprising an antineoplastic agent such as taxane, rapamycin, and 17-AAG) include, but are not limited to, carcinoma, lymphoma, blastoma, sarcoma, and leukemia. Examples of cancers that can be treated by compositions described herein include, but are not limited to, squamous cell cancer, lung cancer (including small cell lung cancer, non-small cell lung cancer, adenocarcinoma of the lung, and squamous carcinoma of the lung, including squamous NSCLC), cancer of the peritoneum, hepatocellular cancer, gastric or stomach cancer (including gastrointestinal cancer), pancreatic cancer (such as advanced pancreatic cancer), glioblastoma, cervical cancer, ovarian cancer, liver cancer (such as hepatocellular carcinoma), bladder cancer, heptoma, breast cancer, colon cancer, melanoma, endometrical or uterine carcinoma, salivary gland carcinoma, kidney or renal cancer, liver cancer, prostate cancer (such as advanced prostate cancer), vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome. In some embodiments, there is provided a method of treating metastatic cancer (that is, cancer that has metastasized from the primary tumor). In some embodiments, there is provided a method of reducing cell proliferation and/or cell migration. In some embodiments, there is provided a method of treating hyperplasia.

In some embodiments, there are provided methods of treating cancer at advanced stage(s). In some embodiments, there are provided methods of treating breast cancer (which may be HER2 positive or HER2 negative), including, for example, advanced breast cancer, stage IV breast cancer, locally advanced breast cancer, and metastatic breast cancer. In some embodiments, the cancer is lung cancer, including, for example, non-small cell lung cancer (NSCLC, such as advanced NSCLC), small cell lung cancer (SCLC, such as advanced SCLC), and advanced solid tumor malignancy in the lung. In some embodiments, the cancer is ovarian cancer, head and neck cancer, gastric malignancies, melanoma (including metastatic melanoma), colorectal cancer, pancreatic cancer, and solid tumors (such as advanced solid tumors). In some embodiments, the cancer is any of (and in some embodiments selected from the group consisting of) breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, gliomas, glioblastomas, neuroblastomas, and multiple myeloma. In some embodiments, the cancer is a solid tumor.

Individual suitable for receiving these compositions depend on the nature of the poorly water soluble pharmaceutical agent, as well as the disease/condition/disorder to be treated and/or prevented. Accordingly, the term individual includes any of vertebrates, mammals, and humans. In some embodiments, the individual is a mammal, including, but not limited to, human, bovine, equine, feline, canine, rodent, or primate. In some embodiments, the individual is human.

The dose of the inventive composition administered to an individual (such as human) will vary with the particular composition, the method of administration, and the particular disease being treated. The dose should be sufficient to effect a desirable response, such as a therapeutic or prophylactic response against a particular disease. For example, the dosage of paclitaxel in the composition can be in the range of 100-400 mg/m$^2$ when given on a 3 week schedule, or 50-250 mg/m$^2$ when given on a weekly schedule. In addition, if given in a metronomic regimen (e.g., daily or a few times per week), the dosage may be in the range of about 5-75 mg/m$^2$.

The compositions described herein can be administered to an individual (such as human) via various routes, including, for example, intravenous, intra-arterial, intrapulmonary, intraportal, intrahepatic, oral, inhalation, intravesicular, intramuscular, intra-tracheal, subcutaneous, intraocular, intrathecal, transmucosal, and transdermal. For example, the inventive composition can be administered by inhalation to treat conditions of the respiratory tract. The composition can be used to treat respiratory conditions such as pulmonary fibrosis, broncheolitis obliterans, lung cancer, bronchoalveolar carcinoma, and the like.

In some embodiments, the administration of the composition is conducted in conjunction with a prion-removal filter.

Also provided herein are methods of reducing side effects associated with administration of the nanoparticle composition. For example, the invention provides methods of reducing various side effects associated with administration of the poorly water soluble pharmaceutical agent, including, but not limited to, myelosuppression, neurotoxicity, hypersensitivity, inflammation, venous irritation, phlebitis, pain, skin irritation, peripheral neuropathy, neutropenic fever, anaphylactic reaction, hematologic toxicity, and cerebral or neurologic toxicity, and combinations thereof. In some embodiments, there is provided a method of reducing hypersensitivity reactions associated with administration of the poorly water soluble pharmaceutical agent, including, for example, severe skin rashes, hives, flushing, dyspnea, tachycardia, and others.

Kits and Systems

The invention also provides kits for use in the instant methods. Kits of the invention include one or more containers comprising the prion-free nanoparticle compositions, and in some embodiments, further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of the invention are in suitable packaging. Suitable packaging include, but is not limited to, vials, bottles, jars, flexible packaging (e.g., seled Mylar or plastic bags), and the like. Kits may optionally provide additional components such as buffers and interpretative information.

The instructions relating to the use of the nanoparticle compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the substantially water insoluble pharmacologically active agent (such as substantially water insoluble pharmacologically active agent) as disclosed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the substantially water insoluble pharmacologically active agent and pharmaceutical compositions and instructions for use and packaged in quantities sufficient for storage and use in pharmacies, for example, hospital pharmacies and compounding pharmacies.

In some embodiments, there is provided a kit for removing a prion protein from a nanoparticle composition comprising albumin and substantially water insoluble pharmacologically active agent, comprising a ligand capable of binding to a prion protein. In some embodiments, the kit further comprises a supporting material. In some embodiments, the kit further comprises an instruction for using the ligand for removing prion from the nanoparticle composition.

Also provided are systems for carrying out methods described herein. For example, in some embodiments, there is provided a system for manufacturing prion-free nanoparticle composition comprising albumin and a substantially water insoluble pharmacologically active agent, said system comprising 1) an apparatus for making the nanoparticle composition; and 2) an apparatus for removing prion proteins from the albumin used for making the nanoparticle composition. In some embodiments, the apparatus for removing prion proteins from said albumin used for making the nanoparticle composition is integrated into the apparatus for making the nanoparticle composition. In some embodiments, the apparatus for making the nanoparticle composition is separated from the apparatus for removing the prion proteins from the albumin used for making the nanoparticle composition.

In some embodiments, there is provided a system for manufacturing prion-free nanoparticle composition comprising albumin and a substantially water insoluble pharmacologically active agent, said system comprising 1) an apparatus for making the nanoparticle composition; and 2) an apparatus for removing prion proteins (for example from an intermediate composition generated during the making of the nanoparticles or from the generated nanoparticle compositions). In some embodiments, the apparatus for removing prion proteins is integrated into the apparatus for making the nanoparticle composition. In some embodiments, the apparatus for making the nanoparticle composition is separated from the apparatus for removing the prion proteins.

Those skilled in the art will recognize that several embodiments are possible within the scope and spirit of this invention.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Embodiments of those preferred embodiments may become apparent to those of ordinary skill in the art upon reading the foregoing description. The inventors expect skilled artisans to employ such embodiments as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible embodiments thereof is encompassed by the invention unless otherwise indicated herein or otherwise clearly contradicted by context.

Exemplary Embodiments of the Present Application

In one aspect, there is provided a composition comprising nanoparticles comprising albumin and a substantially water insoluble pharmacologically active agent, wherein the composition is substantially free of a prion protein. In some embodiments, the composition has a prion infectivity of less than about 100 fg/ml. In some embodiments, the composition is any one of the compositions described above, wherein the composition has a prion infectivity of less than about 10 IU-ic/ml. In some embodiments, the composition is any one of the compositions described above, wherein the composition does not show the presence of a prion protein based on a protein misfolding cyclic amplification (PMCA) assay or based on an IPCR assay. In some embodiments, the composition is any one of the compositions described above, further comprising a trace amount of a ligand capable of binding to a prion protein. In some embodiments, the composition is any one of the compositions described above, further comprising a trace amount of a supporting material.

In another aspect, there is provided a composition comprising nanoparticles comprising albumin and a substantially water insoluble pharmacologically active agent, wherein the albumin in the composition was obtained by a method comprising a prion removal process, said prion removal process comprising contacting an initial albumin composition with a ligand capable of binding to a prion protein. In some embodiments, the prion removal process further comprises removing said ligand and proteins bound thereto from said albumin and composition. In some embodiments, the ligand is a peptide. In some embodiments, the ligand is a trazine-based compound.

In another aspect, there is provided a method of producing a composition comprising nanoparticles comprising albumin and a substantially water insoluble pharmacologically active agent, said method comprising: a) removing a prion protein from an initial albumin composition; b) subjecting a mixture comprising a solution comprising the prion-removed albumin and an organic phase comprising said substantially water insoluble pharmacologically active agent dispersed in an organic solvent to a high shear condition. In some embodiments, step a) comprises: 1) contacting the initial albumin solution with a ligand capable of binding to a prion protein. In some embodiments, step a) further comprises: 2) removing the ligand and proteins bound thereto from the albumin solution. In some embodiments, the method is any of the methods described above, further comprising removing said organic solvent from the mixture. In some embodiments, said removing of the organic solvent is by evaporation. In some embodiments, the method is any one of the methods described above, wherein said ligand is a peptide. In some embodiments, the method is any one of the methods described above, wherein the ligand is a triazine-based compound. In some embodiments, the method is any one of the methods described above, wherein the initial albumin composition is a blood derived product.

In another aspect, there is provided a method of producing a composition comprising nanoparticles comprising albumin and a substantially water insoluble pharmacologically active agent, comprising: a) subjecting a mixture comprising an organic phase comprising said substantially water insoluble pharmacologically active agent and an albumin solution to a high shear condition, and b) removing a prion protein from said mixture. In some embodiments, step b) comprises: 1) contacting the mixture with a ligand capable of binding to a prion protein. In some embodiments, step b) further comprises: 2) removing the ligand and proteins bound thereto from said mixture. In some embodiments, the ligand is a peptide. In some embodiments, the ligand is a triazine-based compound.

Also provided are composition produced by a method of any one of claims 11-23. Also provided are uses of any one of the compositions described above for treating a disease, such as cancer.

In another aspect, there is provide a method of removing a prion protein from a composition suspected of containing a prion protein comprising nanoparticles comprising albumin and a substantially water insoluble pharmacologically active agent, comprising: a) contacting the composition with a ligand capable of binding to a prion protein, b) removing the ligand and proteins bound thereto from the composition. In some embodiments, the ligand is a peptide. In some embodiments, the ligand is a triazine-based compound. Also provided are compositions obtained after the method.

In another aspect, there is provided a composition comprising nanoparticles comprising albumin and a substantially water insoluble pharmacologically active agent, further comprising a ligand capable of binding to a prion protein. In some embodiments, the ligand is a peptide. In some embodiments, the ligand is a triazine-based compound.

The following examples are provided to illustrate, but not to limit, the invention. It is understood that the examples described herein are for illustrative purposes only and that various modifications or changes in light thereof will be suggested to persons skilled in the art and are to be included within the spirit and purview of this application.

EXAMPLES

Example 1

Development of an Affinity Adsorbent for Removal of Prion Protein from Albumin Preparations This study screened a four-resin panel of prion binding ligands by challenging the four-resin panel with two different commercially available albumin preparations (containing 20% w/v or 25% w/v albumin), spiked with scrapie hamster brain homogenate at two different concentrations (0.01% or 0.005%). The four-resin panel was previously identified by PRDT (Pathogen Removal and Diagnostic Technologies Inc; ProMetic Biosciences Ltd., Cambridge, UK) as good prion binders in the presence of 25% albumin Selection of an optimum resin can optimize the incorporation of a prion-reduction step in the production of albumin nanoparticles.

Methodology

Six Protein Isolation Kit for Sorbent Identification (PIKSI™, ProMetic Biosciences Ltd) kits were packed with twelve columns (at about 0.5 mL) of each of the four PRDT resins and the control resin (Toyopearl Amino AMN31). Each resin was challenged with solutions containing 20% and 25% albumin spiked with 0.01% or 0.005% scrapie hamster brain homogenate (SBH) in a three-column series format in an effort to evaluate the binding capacity of each resin to prion proteins. Comparison of resin performance was based on prion protein binding as determined by Western blot and densitometry. Total protein binding profile was determined by SDS-PAGE gels. The bound proteins were stripped from the resins for both the prion protein binding and the total protein binding detection. Albumin binding was determined using NanoDrop® ND-1000 spectrophotometer to measure absorbance at 280 nm. The signals observed in the Western blots and SDS-PAGE gels correspond to the bound fraction of prion protein and total protein, respectively.

The commercial albumin preparations used in this invention were Albumin (Human) U.S.P. Human Albumin Grifols® 20%, Lot No. IBAB8MJ001, and Albumin (Human), USP, 25% solution Baxter, Lot No. LA06D04AA.

Results

Western Blot and SDS-PAGE

Figure 2:
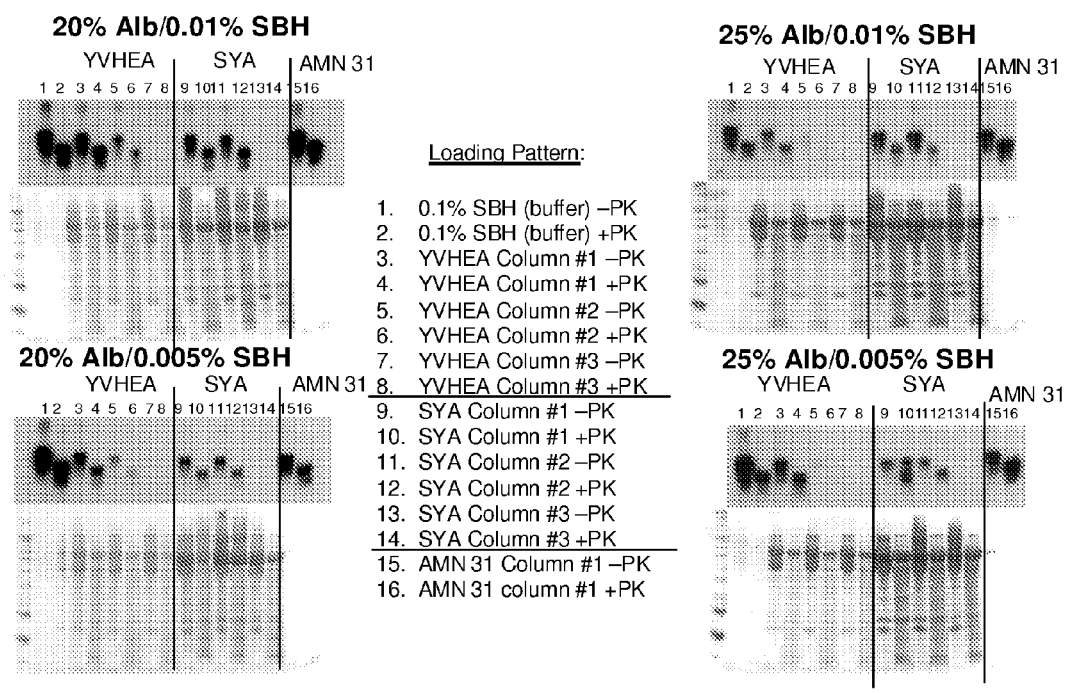
FIG. 2 provides western blots and SDS-PAGE gels of YVHEA and SYA resins challenged with 0.01% and 0.005% scrapie hamster brain homogenate in 20% or 25% albumin AMN31 was the positive control resin. The signal observed was the bound fraction. "–PK" and "+PK" denotes absence or presence of Proteinase K digestion.

The results obtained show that all four resins bound PrPsc spiked into 20% or 25% human albumin solutions. The PrPsc signal intensity in Western blot (FIGS. 1-3) suggests that prion binding was strongest for DVR, followed by YVHEA, SYA, and D4 resins. The control resin, AMN31, had an expected strong signal. The level of signal obtained by using DVR resin suggests that high concentrations of albumin did not interfere in prion binding.

No detectable signal was observed in the second and third columns when using DVR (FIG. 1) at various conditions tested, even when longer exposure times were tested, which indicates that all the detectable PrPsc was captured by the first DVR column.

Signal intensity was weaker for the other resins in the first column, with detection of prion protein in the second column of the series (FIGS. 2 and 3), suggesting a possible interference of albumin to prion protein binding. All three ligands showed no prion signal in the third column, indicating that the resins are capable of selectively removing prions from the SBH spiked albumin solutions. The concentration of PrPsc in hamster brain was about 50 μg/g, equivalent to about 5 ng/mL of PrPsc in 0.01% SBH, spiked into a 250 mg/mL albumin solution, generating a 50,000,000-fold excess of albumin.

The total protein pattern observed in the Coomassie-stained SDS-PAGE gels (FIGS. 1 to 3) shows that DVR had a much lower level of total protein binding than the remaining prion-binding resins, which is considered an advantage, despite the fact that most of the observed bands in the total protein gel came from the brain homogenate spike. As expected, the one visible protein band in the DVR gel has an apparent molecular weight similar to albumin (66.5 KDa).

Densitometry

Prion removal was also assessed indirectly by calculating the ratio of densitometric signal of PrPsc bound to the resin versus the signal present in the albumin solutions spiked with SBH. The ability of DVR resin to bind prion was comparably to the positive control resin, adsorbing approximately all available PrPsc in the first column. Using infectious doses as the measurement for prion binding, the 0.5 mL DVR column was able to remove prion in the 10 mL SBH-spiked albumin solutions, which is equivalent to about $10^6$ $ID_{50}$, considering that 0.1% SBH contains about $10^6$ $ID_{50}$/mL. Similarly to what was observed in the Western blots, DVR had the best performance in prion binding than YVHEA, D4, and SYA. All of three resins required the second column of each series to further bind any detectable prion protein present in SBH-spiked albumin solutions.

Albumin Binding

Albumin concentration was determined using a Nano-Drop® ND-1000 spectrophotometer at absorbance 280 nm for protein quantitation. Each flow-through was measured for the concentration of albumin after passing the SBH-spiked albumin solutions through each of the four resins (DVR, YVHEA, SYA, and D4), and the control resin (AMN31). The protein concentration of commercial albumin solutions at 20% and 25% in the absence or presence of 0.01% or 0.005% SBH spikes was measured before flowing through the resin columns. The results obtained are shown in Table 3.

TABLE 3

Measurement of albumin concentration of commercial albumin solutions (20% w/v or 25% w/v) spiked with or without 0.01% and 0.005% scrapie hamster brain homogenate.

| | Measured Concentration (%) | Measured Concentration (mg/mL) | Average (%) |
|---|---|---|---|
| 20% albumin | 24.8 | 248.0 | 24.6 |
| 20% albumin + 0.01% spike | 24.7 | 247.1 | |
| 20% albumin + 0.005% spike | 24.3 | 243.3 | |
| 25% albumin | 26.8 | 268.1 | 27.6 |
| 25% albumin + 0.01% spike | 28.3 | 282.5 | |
| 25% albumin + 0.005% spike | 27.8 | 278.3 | |

The concentrations of the commercial albumin solutions were measured higher than the commercially labeled value, especially for the preparation containing the 20% w/v albumin solution. However, since the study dealt with comparative values, this was not a concern. The average of three values was obtained, and the amount of the spike was considered negligible when compared to the amount of albumin present in the solutions in determine protein concentration. The concentration of albumin was obtained after flowing SBH-spiked albumin solutions through the resins as shown in Tables 4 and 5.

TABLE 4

Measurement of albumin concentration after flowing commercial albumin solution (20% w/v) spiked with or without 0.01% and 0.005% scrapie hamster brain homogenate through different resin columns.

|  |  | Concentration (mg/mL) | Albumin Loss (%) |
|---|---|---|---|
| DVR | 0.01% spike | 260.4 | ND |
|  | 0.005% spike | 260.4 | ND |
| YVHEA | 0.01% spike | 264.3 | ND |
|  | 0.005% spike | 259.5 | ND |
| SYA | 0.01% spike | 245.5 | 0.2 |
|  | 0.005% spike | 241.7 | 1.7 |
| D4 | 0.01% spike | 263.0 | ND |
|  | 0.005% spike | 265.8 | ND |
| AMN31 | 0.01% spike | 249.8 | ND |
|  | 0.005% spike | 246.9 | ND |

ND = not detected.

TABLE 5

Measurement of albumin concentration after flowing commercial albumin solution (25% w/v) spiked with or without 0.01% and 0.005% scrapie hamster brain homogenate through four different resin columns.

|  |  | Concentration (mg/mL) | Albumin Loss (%) |
|---|---|---|---|
| DVR | 0.01% spike | 268.8 | 2.6 |
|  | 0.005% spike | 284.2 | ND |
| YVHEA | 0.01% spike | 285.7 | ND |
|  | 0.005% spike | 294.2 | ND |
| SYA | 0.01% spike | 280.5 | ND |
|  | 0.005% spike | 262.9 | 4.7 |
| D4 | 0.01% spike | 284.0 | ND |
|  | 0.005% spike | 261.1 | 5.4 |
| AMN31 | 0.01% spike | 272.4 | 1.3 |
|  | 0.005% spike | 282.4 | ND |

ND = not detected.

None of the resins tested showed a significant loss of albumin. In fact, no loss was detected for most of the conditions. The values found indicate a variation of about ±5%. The data suggest that albumin loss is unlikely a factor for choosing one of the resins at this scale, within the range of tested conditions.

Conclusions

Based on the results obtained, DVR is the best resin among the four tested resins for removing prion from commercial albumin solutions. The resin was able to remove around $10^6$ $ID_{50}$ in a 0.5-mL column. This value is similar to the ones obtained in previous trials for other challenges. There was little loss of albumin detected at the tested ratio of challenge with 20 or 25% albumin/resin of 20. Albumin binding should be lower at process conditions, since this ratio is likely to increase.

Example 2

Prion-Removal Feasibility Study of Formulated Suspensions Containing Paclitaxel and of Human Albumin Solution Application of the prion-removal technology in the nanoparticle composition was evaluated using formulated suspensions containing paclitaxel (e.g., Abraxane™) and using human albumin solution containing various percentages of albumin (% w/v).

Experimental Conditions

Study Systems

Formulated Suspensions for Abraxane™ and sugar-paclitaxel formulation were evaluated. Formulated Suspension (FS) for Abraxane™ was formulated with post-evaporated suspension (PE) obtained from the production and human albumin solution (25%, Baxter, Deerfield, Ill.), containing approximately 7 mg/mL paclitaxel and 56 mg/mL human albumin Formulated Suspension (FS) for sugar-paclitaxel formulation was formulated with post-evaporated suspension (PE) obtained from the production, human albumin solution (25%, Baxter), sucrose, sodium chloride and edetate disodium dihydrate, containing approximately 7 mg/ml paclitaxel, 56 mg/ml human albumin; 32 mg/ml sucrose, 8.4 NaCl mg/ml, and 0.07 mg/ml EDTA (ethylenediaminetetraacetic acid).

Human Albumin Solutions in 25%, 20%, and 5% were also evaluated. Human albumin solution in 25% or 250 mg/ml was obtained from Baxter; human albumin solution in 20% or 200 mg/ml (e.g., Grifols®) was obtained from Grifols Biologicals, Inc. (Los Angeles, Calif.). Human albumin solution 5% was made by dilution of 25% human albumin (Baxter) with sterile water for injection.

Prion-Removal Columns

The prion removal columns (1-ml) used in this study were commercially available PIKSI® (Protein isolation Kit for Sorbent Identification) kit columns containing Toyopearl Amino 650CU resin (sample AMN31) supplied by ProMetic Biosciences, Ltd (Cambridge, UK).

Flow-Through Conditions

For the study on formulation suspension, the total flow-through volume was about 500 mL, which was 500 times the column volume (1-ml). The flow rate was about 0.5 ml/min Total flow-through time was more than 16 hours. Samples were taken every two hours. No clogging of the column was observed.

For the study on albumin solution, the total flow-through volume was at least 100 mL, which was 100 times the column volume (1-ml). The flow rate was about 0.5 ml/min Total flow-through time was more than 3 hours. Samples were taken every hour. No clogging of the column was observed.

Results and Discussion

The results from the prion-removal feasibility study on the formulated suspension are summarized in Table 6 and Table 7. The physical and chemical testing results for the formulated suspension for Abraxane™ show no significant differences between the pre and post-column suspension, in terms of particle size, pH, paclitaxel assay and impurities, human albumin assay, and human albumin composition. Likewise, the physical and chemical testing results for the formulated suspension for sugar-paclitaxel formulation show no significant differences between the pre and post-column suspension, in terms of particle size, pH, paclitaxel assay and impurities, human albumin assay, human albumin composition, sucrose, and EDTA.

TABLE 6

Prion-Removal Feasibility Study of Abraxane™ Formulated Suspension

| Physical and Chemical Properties | | Pre-Column | Post Column | | | | | | |
|---|---|---|---|---|---|---|---|---|---|
| | | | #1 | #2 | #3 | #4 | #5 | #6 | #7 |
| Particle Size (nm) | Mean | 131 | 132 | 132 | 133 | 133 | 133 | 131 | 130 |
| | <5% | 82 | 86 | 85 | 86 | 85 | 87 | 84 | 82 |
| | <95% | 193 | 190 | 191 | 192 | 192 | 191 | 191 | 190 |
| | <99.9% | 254 | 250 | 251 | 252 | 253 | 250 | 251 | 250 |
| pH | | 7.0 | 7.0 | 7.1 | 7.0 | 7.0 | 7.0 | 7.0 | 7.0 |
| Paclitaxel (mg/mL) | | 6.9 | 6.9 | 6.9 | 6.8 | 6.8 | 6.8 | 6.8 | 6.8 |
| Human Albumin Composition (%) | Polymer | 3.99 | 3.86 | 3.93 | 3.95 | 3.95 | 3.92 | 3.88 | 3.76 |
| | Oligomer | 1.32 | 1.36 | 1.32 | 1.34 | 1.31 | 1.32 | 1.34 | 1.39 |
| | Dimer | 5.95 | 5.96 | 6.00 | 5.98 | 6.00 | 5.99 | 5.98 | 5.96 |
| | Monomer | 88.29 | 88.37 | 88.24 | 88.27 | 88.27 | 88.28 | 88.29 | 88.38 |
| Total Human Albumin (mg/mL) | | 55 | 56 | 56 | 56 | 56 | 56 | 56 | 56 |
| Impurity (%) | 7-Epi | 0.08 | 0.08 | NA | NA | 0.09 | NA | NA | 0.09 |
| | Total | 0.25 | 0.25 | NA | NA | 0.26 | NA | NA | 0.26 |

*NA: Data not Available.

TABLE 7

Prion-Removal Feasibility Study of Sugar-EDTA-Paclitaxel Formulated Suspension

| Physical and Chemical Properties | | Pre-Column | Post Column | | | | | | |
|---|---|---|---|---|---|---|---|---|---|
| | | | #1 | #2 | #3 | #4 | #5 | #6 | #7 |
| Particle Size (nm) | Mean | 129 | 130 | 133 | 131 | 132 | 132 | 130 | 132 |
| | <5% | 80 | 81 | 85 | 82 | 84 | 85 | 81 | 85 |
| | <95% | 191 | 192 | 193 | 193 | 192 | 191 | 192 | 191 |
| | <99.9% | 252 | 253 | 253 | 254 | 253 | 251 | 253 | 250 |
| pH | | 6.8 | 6.8 | 6.8 | 6.9 | 6.8 | 6.8 | 6.9 | 6.9 |
| Paclitaxel (mg/mL) | | 6.5 | 6.5 | 6.5 | 6.5 | 6.5 | 6.6 | 6.6 | 6.5 |
| Human Albumin Composition (%) | Polymer | 3.90 | 3.90 | 3.91 | 3.89 | 3.91 | 3.93 | 3.94 | 3.93 |
| | Oligomer | 1.92 | 1.89 | 1.92 | 1.90 | 1.91 | 1.89 | 1.44 | 1.41 |
| | Dimer | 6.14 | 6.11 | 6.11 | 6.10 | 6.10 | 6.09 | 6.09 | 6.10 |
| | Monomer | 88.02 | 88.10 | 88.07 | 88.09 | 88.06 | 88.09 | 88.03 | 88.04 |
| Total Human Albumin (mg/mL) | | 55 | 55 | 54 | 54 | 55 | 55 | 54 | 54 |
| Impurity (%) | 7-Epi | 0.08 | 0.08 | NA | NA | 0.08 | NA | NA | 0.09 |
| | Total | 0.25 | 0.25 | NA | NA | 0.25 | NA | NA | 0.26 |
| Sucrose (mg/mL) | | 31.8 | 31.8 | NA | NA | 31.6 | NA | NA | 31.9 |
| EDTA (mg/mL) | | 0.071 | 0.071 | NA | NA | 0.070 | NA | NA | 0.070 |

* NA: Data not Available.

The results from the prion-removal feasibility study on the albumin solutions are summarized in Table 8. There are no significant differences between the pre and post-column solution, in terms of human albumin assay and human albumin composition.

TABLE 8

Prion-Removal Feasibility Study of Human Albumin Solution

| Sample I.D. | | HA (%) | | | | HA Total (mg/mL) |
|---|---|---|---|---|---|---|
| | | Polymer | Oligomer | Dimer | Monomer | |
| Lot 28203-37A | | | | | | |
| 25% Human Albumin (Baxter) | Pre column | 3.66 | 0.28 | 2.38 | 93.69 | 248 |
| | Post column #1 | 3.60 | 0.25 | 2.41 | 93.74 | 248 |
| | Post column #2 | 3.63 | 0.28 | 2.38 | 93.71 | 250 |
| | Post column #3 | 3.64 | 0.24 | 2.41 | 93.71 | 247 |
| | Post column #4 | 3.64 | 0.26 | 2.40 | 93.70 | 248 |

TABLE 8-continued

Prion-Removal Feasibility Study of Human Albumin Solution

| Sample I.D. | | Polymer | Oligomer | Dimer | Monomer | HA Total (mg/mL) |
|---|---|---|---|---|---|---|
| | | | HA (%) | | | |
| Lot 28203-37B | | | | | | |
| 20% Human Albumin (Grifols) | Pre column | 4.85 | 0.51 | 3.25 | 91.39 | 199 |
| | Post column #1 | 4.78 | 0.49 | 3.25 | 91.48 | 199 |
| | Post column #2 | 4.78 | 0.51 | 3.25 | 91.45 | 200 |
| | Post column #3 | 4.86 | 0.51 | 3.25 | 91.38 | 200 |
| Lot 28203-37C | | | | | | |
| 5% Human Albumin (Baxter) | Pre column | 3.66 | 0.27 | 2.32 | 93.75 | 52 |
| | Post column #1 | 3.33 | 0.25 | 2.31 | 94.10 | 51 |
| | Post column #2 | 3.48 | 0.27 | 2.30 | 93.94 | 51 |
| | Post column #3 | 3.54 | 0.27 | 2.31 | 93.89 | 51 |
| | Post column #4 | 3.50 | 0.27 | 2.31 | 93.92 | 52 |

This study demonstrates that the prion-removal column treatment has no adverse impact on the physical and chemical properties of human albumin solution and formulated suspensions for both Abraxane™ and sugar-paclitaxel formulation.

Example 3

TSE Removal by Prion Reduction Resins for 20% Albumin

In this study, potential TSE removal by prion reduction resins (PRDT column; ProMetic Biosciences, Ltd) in 20% (w/v) albumin (Grifols®) was evaluated. Starting material for the TSE removal process step was spiked with a model TSE agent. The process step was performed in the VirusSure laboratories (Virusure Forschung und Entwicklung GmbH, Vienna, Austria). Various fractions were collected during performance of the process step, and the TSE removal capacity of the process was calculated based on a determination of levels of TSE agent using a Western Blot assay for the detection of PrPsc.

This study followed and referenced the following guidelines, including 1) CPMP/BWP/268/95 (revised in 1996), Note for Guidance on Virus Validation Studies: The Design, Contribution, and Interpretation of Studies Validating the Inactivation and Removal of Viruses; 2) CPMP/BWP/5136/03 Guideline on the Investigation of Manufacturing Processes for Plasma-Derived Medicinal Products with Regards to vCJD Risk; 3) OECD Principles of Good Laboratory Practice as outlined in ENV/MC/CHEM(98)17, revised in 1997; 4) 21 CFR part 58, Good Laboratory Practice, US FDA; 5) EU directive 2004/9/EG, Inspection und Überprüfung der Guten Laborpraxis (GLP); 6) EU Directive 2004/10/EG, Anwendung der Grundsätze der guten Laborpraxis und zur Kontrolle ihrer Anwendung bei Versunchen mit chemischen Stoffen; 7) Austrian BGBI. II, 211. Verordnung, Chemikalien-GLP-Inspektionsverordnung, Jahrgang 2000; and 8) Austrian BGBI. II, 450. Verordnung, gute Laborpraxis 2006, Jahrgang 2006.

Materials and Methods

The following test articles, reagents, and materials were used during the course of this study for the investigation of TSE removal by the prion reduction resins (PRDT column) for 20% albumin (Grifols®).

Grifols® Albumin (human) (USP 20% solution (Lot: IBAB7GX001/TA09/0122)) was used for spiked run and interference testing.

Disposable SepFast™ Column (ProMetic Biosciences Ltd.) containing 5 ml of prion removal resin packed in 9% saline was used for process run.

Various buffers were prepared. They include the following:

1) 0.9% NaCL (9 g/l) was prepared as equilibration buffer for the prion reduction resins;
2) Tris Buffered Saline (TBS) was prepared as re-suspension of the resins following chromatography;
3) 2M NaCl (116.88 g/l) was prepared as prion reduction resin regeneration buffer;
4) NaOH (0.1M, 0.5M, and 1.0 M) buffers were prepared for pH adjustments of spiked study samples and process intermediates inactivation of infectious material; and
5) HCL (0.1M and 1.0M) buffers were prepared for pH adjustments of spiked study samples and process intermediates.

263 Scrapie

Strain 263K Hamster Adapted scrapie (0.5% sarkosyl treated) was used in this study. The 263K strain of hamster adapted scrapie provides the advantages of high titres in the brains of hamsters. Typical titres for a 10% brain homogenate are in the range of $10^8$-$10^{10}$ $ID_{50}$ units per ml. The PrPsc protein deposited by this agent is relatively resistant to Proteinase K digestion, allowing the possibility of distinguishing between the non-disease associated form of the protein PrPc. The seed 263K strain of hamster adapted scrapie was supplied as a 10% homogenate by the laboratory of Dr. Robert Rohwer (Baltimore Research and Education Foundation, Mail Stop 151-A, 10 North Greene Street, Baltimore, Md. 21201, USA). A 0.5% sarkosyl-treated fraction was selected for this experiment. This fraction was prepared from a crude brain homogenate (from which the microsomal/cytosolic 263K fraction had already been removed) by treatment with 0.5% sarkosyl followed by differential centrifugation to remove larger aggregates, leaving only the detergent solubilized fragments in the supernatant. The 0.5% sarkosyl-treated fraction was prepared to mimic detergent solubilized contamination (i.e., as found in solvent detergent containing processes), and this type of fraction has been widely used in prion clearance studies for human plasma and recombinant products.

Western Blot Assay for the Detection of PrPsc

The Western blot assay for detection of PrPsc was used for the semi-quantitative determination of TSE levels (PrPsc) in the various samples. The dynamic range of the Western blot assay is normally in the region of 4-5 $\log_{10}$ dilutions before signal is lost, and thus the assay is less sensitive than the hamster bioassay. However, the Western blot assay is a useful tool in assessing prion removal by biopharmaceutical manufacturing processes.

In the Western blot assay, the sample was first submitted to digestion with Proteinase K to remove the normal form of the protein, PrPc (all process samples were digested using a Proteinase K concentration of 83 pg/ml). After blocking of the proteolytic reaction, the sample was mixed with SDS-buffer and boiled to denature the PrPsc from its aggregated form. 0.5 $\log_{10}$ dilutions of the sample are then prepared and loaded onto a SDS-PAGE gel along with a molecular weight marker. Following electrophoresis, the gel was Western blotted onto a PVDF membrane, followed by blocking and probing with antibodies allowing the detection of bound PrPsc protein with the antibody 3F4. The 263K strain of scrapie results in a characteristic banding pattern in the region of 25-33 KDa, which assists in confirming the presence of the PrPsc protein in samples. The end point of titre of the sample was defined as the first dilution where no signal was observed on the Western blot.

Calculation of Reduction Factors

Reduction factors (RF) were calculated as follows:

$$RF = (V_1 \times T_1)/(V_2 \times T_2)$$

Where:

$V_1$ and $T_1$ are the volume and titre of the starting material respectively, and $V_2$ and $T_2$ are the volume and titre of the product fraction respectively In logarithmic terms, this equation can be expressed as:

$$\mathrm{Log}_{10}[RF] = [\mathrm{Log}_{10}(V_1) + \mathrm{Log}_m(T_1)] - [\mathrm{Log}_{10}(V_2) + \mathrm{Log}_{10}(T_2)].$$

Reduction factors were rounded to 1 decimal place only after the final calculation.

Interference Testing

The starting material was tested undiluted and followed by a 1.0 $\log_{10}$ pre-dilution in TBSA. Following spiking with 263K to a final concentration equivalent to a titre within approximately 2 $\log_{10}$ of the end point of the Scrapie stock used for spiking, the undiluted and pre-diluted starting material samples were centrifuged at 15.558×g for 60 min at room temperature. Following centrifugation, the supernatant was carefully decanted and the pellets re-suspended with TBSA in 1/10 of the original centrifuged sample volume (equivalent to no effective concentration for 1.0 $\log_{10}$ pre-diluted sample and equivalent to a 10-fold concentration for the undiluted sample). Protease K digestion and Western blotting was then performed following the standard protocol. The regeneration and column samples were diluted 0.5 $\log_{10}$ or tested undiluted respectively prior to analysis by Western blotting (i.e., without centrifugation).

Adjustment of pH

Prior to aliquotting and storage at ≤−60° C., samples were checked to be at pH 6-8 (pH adjustment was not required for any of the samples).

Equipment

The following main equipment items were used for performance of this study. Sterile Class II Biohazard Safety Cabinet, Sanyo & Angelantoni≤−60° C. freezers, Angelantoni 2-8° C. fridges and ≤−15° C. freezers, Sartorius or Kern (analytical) balance and printer, Hanna electronic thermometer, Mettler Toledo pH meter, Grant or Selecta water baths, Oregon Laboratory Timer, Hettich microfuge, BioRad Criterion Electrophoresis Cell, BioRad Criterion Blotter, AKTA Chromatography system, Wealtec Power Supply, Agfa Film Developer, and Biotoolomics column packed with PRDT resin.

Process Flow

Figure 4:
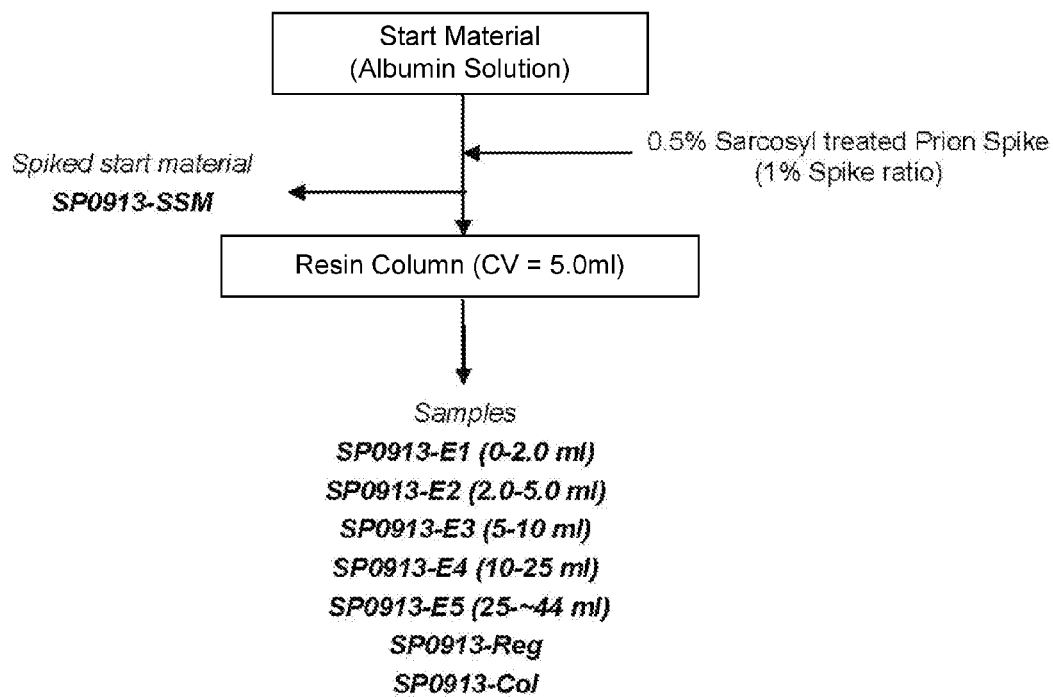
FIG. 4 depicts the process flow scheme for the TSE removal by the prion reduction resin column (PRDT (Pathogen Removal and Diagnostic Technologies) column) for 20% albumin.

The process flow scheme along with the samples collected was depicted in FIG. 4. The volumes of the respective samples can be found in Table 9 in the Results Section.

In preparation of the process flow, the Laminar Flow (LF) safety cabinet was cleaned and turned on for at least 10 to 15 minutes to equilibrate. The water bath was equilibrated to 30±2° C. and the starting material equilibrated until a temperature of 29.5° C. was reached. The 0.5% Sarkosyl solubilized spike was thawed in the same water bath and as soon as it was thawed, placed on ice until use. The PRDT column was equilibrated to ambient temperature (23.0±5.0° C.) overnight.

The column inlet tubing (top) was connected to the outlet from the ÄKTA. The tubing from the column outlet (bottom) was fed to an appropriate collection vessel (beaker or 50 ml disposable centrifuge tube). All tubing was already primed with WFI (Water for Injection) such that no air bubbles were introduced into the system.

The column was first equilibrated with 5 column volumes (CV) of WFI, and then with 10 CV of Equilibration Buffer. The target flow rate throughout was 2.0±0.1 ml per minute.

Sample Preparation and Prion Reduction Resin Chromatography 50.7 ml of the equilibrated starting material was spiked with 0.51 ml of 0.5% sarkosyl solubilized 263K homogenate. The pH was then be checked and found to be within the target range of 6.9-7.4. Subsequently, a 0.5 ml aliquot was removed (sample SSM) and aliquotted and stored at ≤−60° C.

The spiked sample was then applied to the above equilibrated PRDT column at a flow rate of 1.8±0.1 ml per min and the flow through collected as the following fractions:

| Sample ID | Volume | Sample Description |
|---|---|---|
| E1 | 2.1 ml | Eluate 1 (−0-2 ml) |
| E2 | 3.2 ml | Eluate 2 (−2-5 ml) |
| E3 | 5.4 ml | Eluate 3 (−5-10 ml) |
| E4 | 16.1 ml | Eluate 4 (−10-25 ml) |
| E5 | 30.3 ml | Eluate 5 (−25-44 ml) |

Collection of E1 began once the absorbance had reached 80% of the full scale deflection. For each run, the flow through fraction was collected (the volume of each Eluate sample collected was determined by weighing). After loading of the spiked Albumin solution, the column was washed with 10.0 ml of Equilibration Buffer. Collection of the E5 sample was stopped once the absorbance had dropped below 80% of full scale deflection. Following the Equilibration Buffer wash, the column was regenerated using >20.0 ml of 2M NaCl (sample REG), and following regeneration the resin removed and resuspended in 5 ml of TBS (sample COL).

Results

Samples from Spiked Runs

Figure 5:
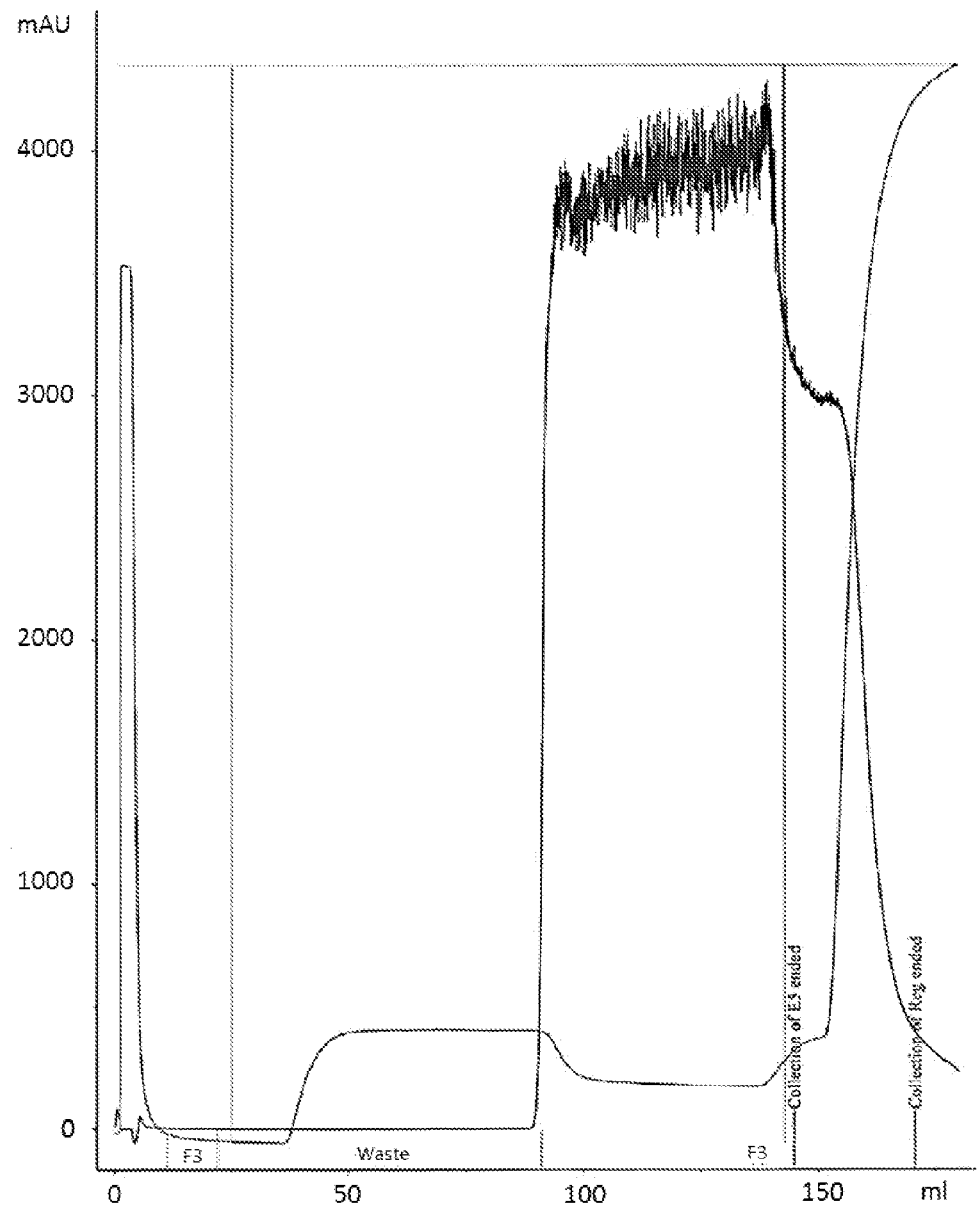
FIG. 5 shows a chromatography profile from the spiked run in the study of TSE removal by the PRDT column for 20% albumin.

Table 9 below lists the samples that were collected from the spiked run along with the volume of each sample. Where the sample size was determined by weight, then a density of 1.0 g/ml was assumed to allow a calculation of the volume for each sample. All samples were stored aliquotted at −60° C. until analysis. A scanned reproduction of the chromatography profile from the spiked run is shown in FIG. 5.

TABLE 9

Summary of volumes collection during the process run

| Sample Description | Sample Code | Actual volume of sample collected at point of collection (ml) |
|---|---|---|
| Spiked Start Material (Sarkosyl-treated spike) | SP0913-SSM | 51.2 |
| Eluate 1: 0-2 ml | SP0913-E1 | 2.1 |
| Eluate 2: 2-5 ml | SP0913-E2 | 3.2 |
| Eluate 3: 5-10 ml | SP0913-E3 | 5.4 |
| Eluate 4: 10-25 ml | SP0913-E4 | 16.1 |
| Eluate 5: 25–44 ml | SP0913-E5 | 30.3 |
| Regeneration fraction | SP0913-Reg | 27.5 |
| Resin sample | SP0913-Col | 10.0 |

Interference Results

To overcome interference all samples except the regeneration and resin samples were diluted by $1.0\ \log_{10}$ with TBS containing 0.1% BSA followed by a centrifugation and a $\frac{1}{10}$ concentration. The undiluted sample tested for interference at a 10× concentration displayed strong interference. For the regeneration samples a $0.5\ \log_{10}$ dilution was prepared prior to testing to reduce the concentration of NaCl. For the resin samples, as the resin was resuspended in TBS buffer, these samples were tested without pre-dilution.

Figure 6:
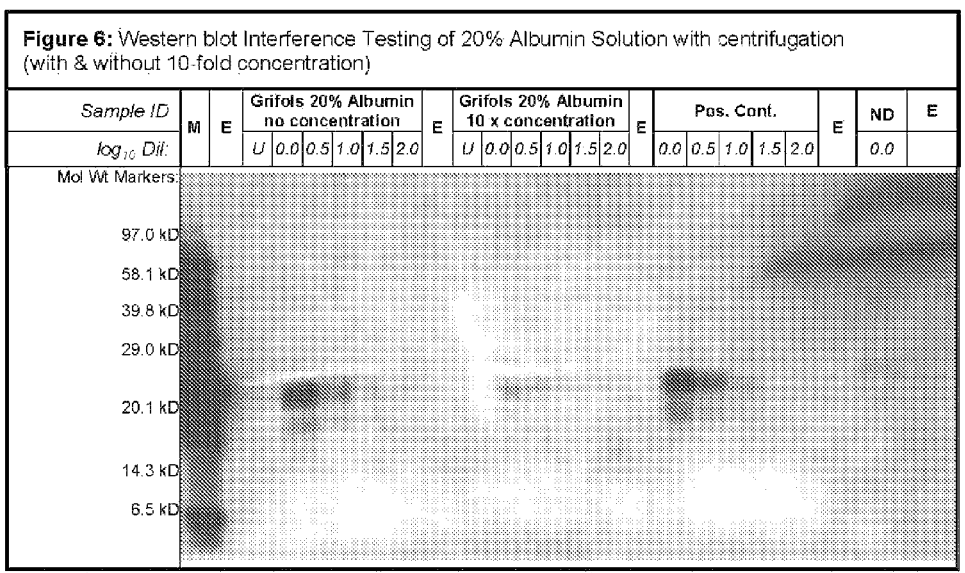
FIG. 6 shows the Western blot interference testing of 20% albumin solution with centrifugation (with and without 10-fold concentration).

The dilution of sample required to overcome interference with albumin was made using 1.0 Log 10 predilution with centrifugation and resuspension in $\frac{1}{10}^{th}$ original volume. See FIG. 6.

Prion Titration Data and Calculation of Reduction Factors

The calculation of the prion reduction factors for the process runs is shown in Table 10. The dilution of sample used in order to overcome interference is also shown in Table 10.

A reduction factor of $2.5\ \log_{10}$ relative to the spiked start material was calculated for E1 sample, which represented the first 2.0 ml passed over the PRDT column. In samples E2 to E5, a breakthrough of PrPsc into the flow through fraction was observed (reduction factor $1.5\ \log_{10}$ for sample E5). No PrPsc was detected in the regeneration sample and the equivalents of PrPsc bound to the PRDT resin was discussed in more detail in the section of calculation of the prion binding capacity of the PRDT resin below.

Calculation of the Prion Binding Capacity of the Prion Reduction Resins

In order to estimate the binding capacity for the prion reduction resins (PRDT resin) for infectious prion protein, the titres observed in the Western blot testing were related to infectious titres. The Western blot assay used a 263K stock of known titre. A dilution series of the reference stock was prepared and tested in the Western blot assay. After plotting the obtained titres versus the respective titres observed in the hamster bioassay, a linear regression analysis was performed to assess the relation between the two test systems. The slope and intercept for the regression line were calculated to be 1.0667 and −4.5867, respectively. The regression parameters were used to convert Western blot titres into infectious titres using the following formula:

$$\text{Titre}_{[Bioassay]} = (\text{Titre}_{[WesternBlot]} + 4.5867)/(1.0667).$$

Once the infectious titre per ml was calculated, the total prion bound to the column could be determined. The calculated prion protein binding capacity of the prion reduction resin is shown in the Table 11 below. The capacity was determined using the amount of PrPsc observed directly bound to the prion reduction resin (samples Reg and Col).

TABLE 10

Summary of Sample Titration Data and Prion Reduction Factors

| Sample ID | Sample Description | Log dilution for interference | End point titre | Sample Volume at collection | Volume Further Processed | Correction Factor for Volume processed* | Volume of Samples Before pH Adjustment | Volume of Samples After pH Adjustment | pH Adjustment Correction Factor | Log volume | Total Load |
|---|---|---|---|---|---|---|---|---|---|---|---|
| SP0913-SSM | Spiked start material | 0.0 | 2.5 | 51.2 ml | 50.7 ml | 0.99 | — | — | — | 1.7 | 4.205 |
| SP0913-E1 | Eluate Fraction 1 | 0.0 | 0.0 | 50.7 ml | — | — | — | — | — | 1.7 | ≤1.705 |
| SP0913-E2 | Eluate Fraction 2 | 0.0 | 1.0 | 50.7 ml | — | — | — | — | — | 1.7 | 2.705 |
| SP0913-E3 | Eluate Fraction 3 | 0.0 | 1.0 | 50.7 ml | — | — | — | — | — | 1.7 | 2.705 |
| SP0913-E4 | Eluate Fraction 4 | 0.0 | 1.5 | 50.7 ml | — | — | — | — | — | 1.7 | 3.205 |
| SP0913-E5 | Eluate Fraction 5 | 0.0 | 1.0 | 50.7 ml | — | — | — | — | — | 1.7 | 2.705 |
| SP0913-Reg | Regeneration Fraction | 0.5 | 0.0 | 27.5 ml | — | — | — | — | — | 1.4 | ≤1.939 |
| SP0913-Col | Column Resin | 0.0 | 3.0 | 10.0 ml | — | — | — | — | — | 1.0 | 4.000 |

| | | Sample # | Sample ID | Sample Description | Log Titre | RF |
|---|---|---|---|---|---|---|
| Reduction Factor 1: | | Sample 1 | SP0913-SSM | Spiked start material | 4.205 | |
| | | Sample 2 | SP0913-E1 | Eluate Fraction 1 | 1.705 | ≥2.50 |
| | | Comments: | | RF for eluate 1 relative to spiked start material | | |
| Reduction Factor 2: | | Sample 1 | SP0913-SSM | Spiked start material | 4.205 | |
| | | Sample 6 | SP0913-E5 | Eluate Fraction 5 | 2.705 | 1.50 |
| | | Comments: | | RF for eluate 5 relative to spiked start material | | |

*Correction factors are applied in the final log volume calculation. The correction factors applicable for each sample are the correction factors of the respective sample itself along with all correction factors for samples listed below that sample.
**A volume of 50 ml was used for the purpose of calculating the reduction factor for each eluate sample, to ensure a direct comparison with the volume loaded onto the column.

TABLE 11

Prion binding capacity of Prion Reduction Resin (PRDT Resin)

| Sample ID | Sample Description | Total PrPsc $(\log_{10}{}^{WB})$# | Infectious PrPsc $(\log_{10} ID_{50}$ total$)$ = Total PrPsc + 4.1 | Binding capacity per ml $(ID_{50}/ml)$* |
|---|---|---|---|---|
| Albumin spiked with a sarkosyl solubilised spike | | | | |
| SP0913-SSM | 50 ml albumin spiked with 0.5 ml of a sarkosyl solubilised spike 5.0 ml PRDT Resin; 50 ml of SP0912-SSM sample loaded (Target flow rate: 1.8 ml/min) | 4.2♣ | 8.3 | — |
| SP0912-Reg | 2M NaCl salt wash (sample volume 25.1 ml) | ≤1.9 | ≤6.0 | ≤5.3 $\log_{10}$/ml |
| SP0912-Col | Column resin (sample volume 8.7 ml) | 4.0 | 8.1 | 7.4 $\log_{10}$/ml |

Total PrPSc includes corrections for volume of sample as well as concentration/dilution prior to testing ♣ Total load based on a final volume of 50 ml loaded onto the PRDT column * Based on a 5.0 ml column size The total binding of PrPsc to the PRDT resin following a 2M salt wash was 7.4 $\log_{10}$ $ID_{50}$/ml. No PrPsc was detected in the salt wash fractions by western blot. Significant PrPsc removal (≥2.5 $\log_{10}$) was also observed.

When performing interference testing, the starting material was tested undiluted, with centrifugation and 10-fold concentration. This was performed to allow an evaluation of the possibility for concentrating the samples and thus achieving higher reduction factors.

Example 4

TSE Removal by the Prion Reduction Resins for 25% Albumin

In this study, potential TSE removal by the prion reduction resins (PRDT column) in 25% albumin (Baxter, Deerfield, Ill.) was evaluated. Materials and Methods used were the same as described in Example 3, with the exception that Albumin (Human) USP 25% solution from Baxter (Lot: LA07D051AB/TA09/0123) was used as the starting material for spiked run and interference testing.

Process Flow

Figure 7:
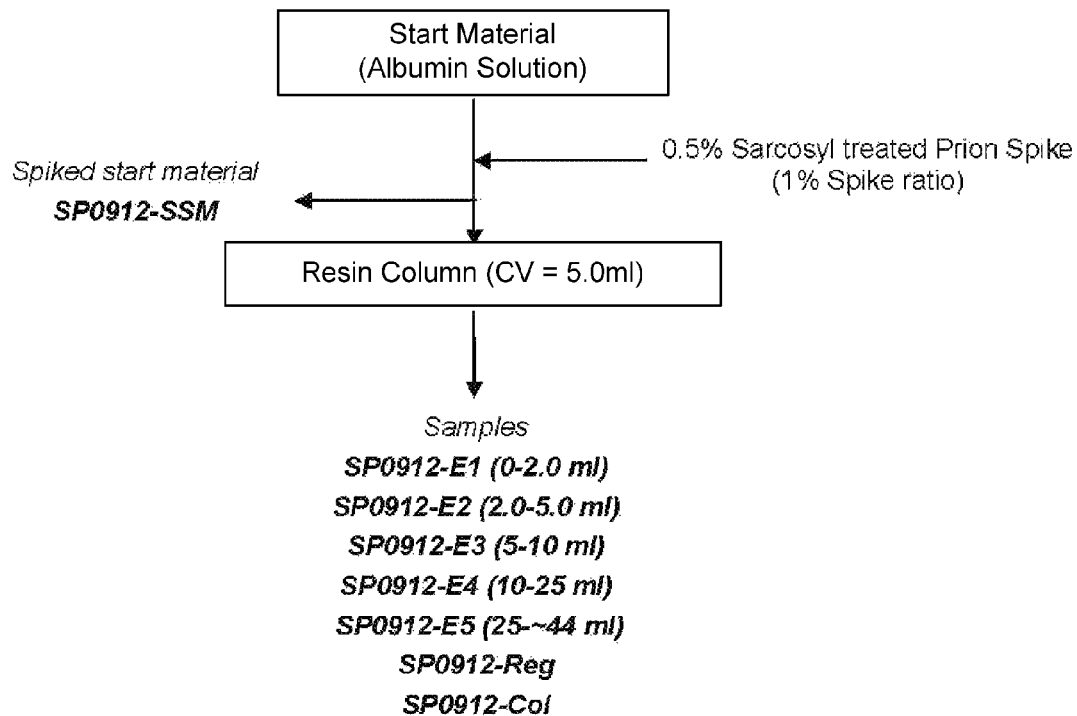
FIG. 7 depicts the process flow scheme for the TSE removal by the prion reduction resin column (PRDT column) for 25% albumin.

The downscale process was established and performed at the ViruSure facilities. The process flow scheme along with the samples collected was depicted in FIG. 7. The volumes of the respective samples can be found in Table 12 in the Results Section. The parameters and procedures used in preparation of the process flow, including connecting the ÄKTA and column, column equilibration are the same as described in Example 3.

Sample Preparation and Prion Reduction Resin Chromatography 50.1 ml of the equilibrated starting material was spiked with 0.51 ml of 0.5% sarkosyl solubilized 263K homogenate. The pH was then be checked and found to be within the target range of 6.9-7.4 with 0.1M HCL or 0.5 M NaOH. The pH of the spiked starting material (6.85) was outside the target range of 6.9-7.4 (see Deviations Section). After the addition of 65 μL 0.1M NaOH and 50 μl 1M NaOH, the pH value remained unchanged, so the decision was taken to load the starting material at this pH. Subsequently, a 0.5 ml aliquot was removed (sample SSM) and aliquotted and stored at ≤−60° C.

The spiked sample was then applied to the above equilibrated PRDT column at a flow rate of 1.8±0.1 ml per min, and the flow through were collected as the following fractions:

| Sample ID | Volume | Sample Description |
|---|---|---|
| E1 | 2.3 ml | Eluate 1 (−0-2 ml) |
| E2 | 3.3 ml | Eluate 2 (−2-5 ml) |
| E3 | 5.6 ml | Eluate 3 (−5-10 ml) |
| E4 | 16.1 ml | Eluate 4 (−10-25 ml) |
| E5 | 32.7 ml | Eluate 5 (−25-44 ml) |

Collection of E1 began once the absorbance had reached 80% of the full scale deflection. For each run, the flow through fraction was collected (the volume of each Eluate sample collected was determined by weighing). After loading of the spiked albumin solution, the column was washed with 10.0 ml of Equilibration Buffer. Collection of the E5 sample was stopped once the absorbance had dropped below 80% of full scale deflection. Following the Equilibration Buffer wash, the column was regenerated using >20.0 ml of 2M NaCl (sample REG), and following regeneration the resin removed and resuspended in 5 ml of TBS (sample COL).

Results

Samples from Spiked Runs

Figure 8:
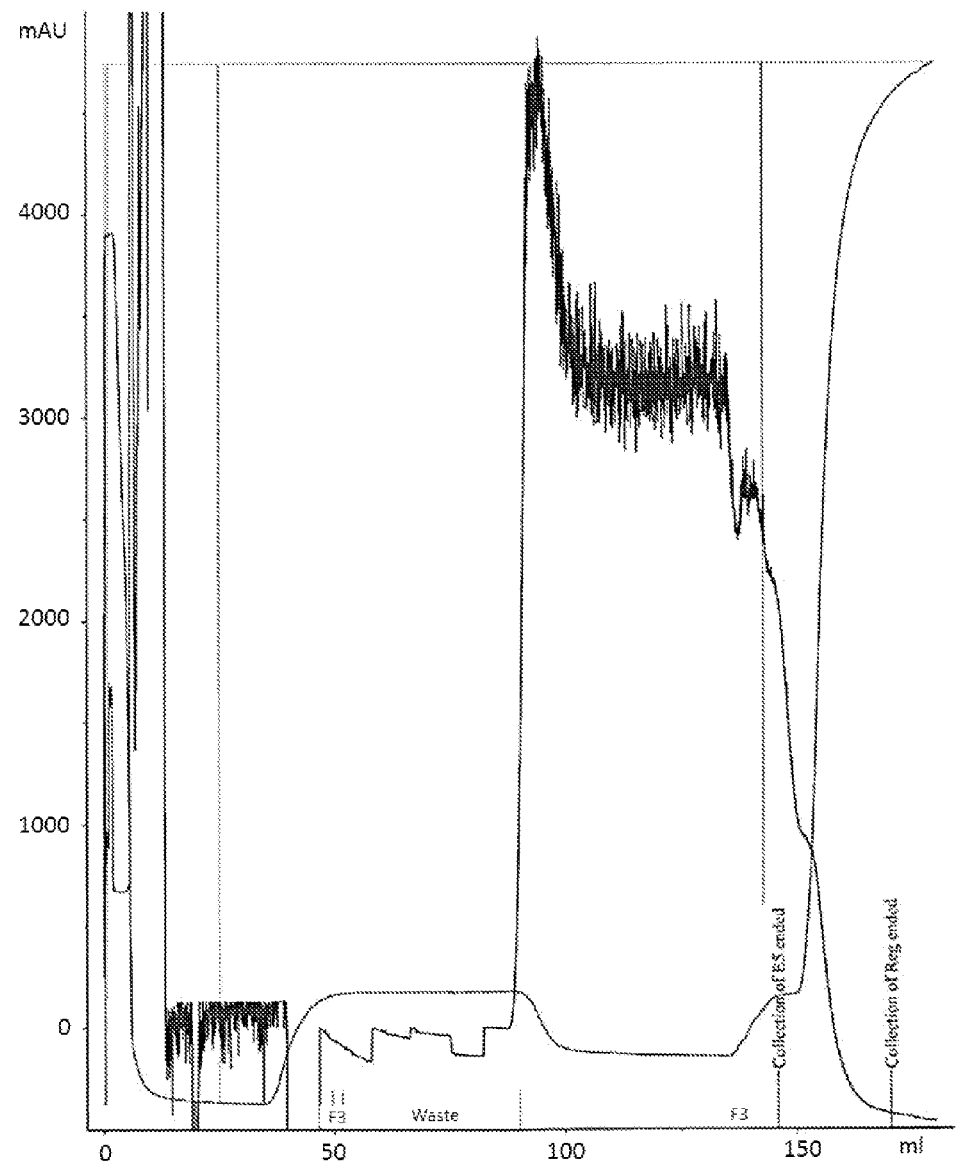
FIG. 8 shows a chromatography profile from the spiked run in the study of TSE removal by the PRDT column for 25% albumin.

Table 12 below lists the samples that were collected from the spiked run along with the volume of each sample. Where the sample size was determined by weight, then a density of 1.0 g/ml was assumed to allow a calculation of the volume for each sample. All samples were stored aliquotted at ≤−60° C. until analysis. A scanned reproduction of the chromatography profile from the spiked run is shown in FIG. 8.

TABLE 12

Summary of volumes collection during the process run

| Sample Description | Sample Code | Actual volume of sample collected at point of collection (ml) |
|---|---|---|
| Spiked Start Material (Sarkosyl-treated spike) | SP0912-SSM | 50.6 |
| Eluate 1: 0-2 ml | SP0912-E1 | 2.3 |
| Eluate 2: 2-5 ml | SP0912-E2 | 3.3 |
| Eluate 3: 5-10 ml | SP0912-E3 | 5.6 |
| Eluate 4: 10-25 ml | SP0912-E4 | 16.1 |
| Eluate 5: 25--44 ml | SP0912-E5 | 32.7 |
| Regeneration fraction | SP0912-Reg | 25.1 |
| Resin sample | SP0912-Col | 8.7 |

Interference Results

To overcome interference with albumin, all samples except the regeneration and resin samples were diluted by 1.0 $\log_{10}$ with TBS containing 0.1% BSA followed by a centrifugation and a ⅒ concentration. The undiluted sample tested for interference at a 10-fold concentration displayed strong interference. For the regeneration samples, a 0.5 $\log_{10}$ dilution was prepared prior to testing to reduce the concentration of NaCl. For the resin samples, as the resin was resuspended in TBS buffer, these samples were tested without pre-dilution.

The dilution of sample required to overcome interference was made using 1.0 Log 10 predilution with centrifugation and resuspension in ⅒$^{th}$ of the original volume. See FIG. 9.

Prion Titration Data and Calculation of Reduction Factors

The calculation of the prion reduction factors for the process runs is shown in Table 13. The dilution of sample used in order to overcome interference is also shown in Table 13.

A reduction factor of ≥2.5 $\log_{10}$ relative to the spiked start material was calculated for E1 sample, which represented the first 2.0 ml passed over the PRDT column. In samples E2 to E5, a breakthrough of PrPsc into the flow through fraction was observed (reduction factor 1.5 $\log_{10}$ for sample E5). No PrPsc was detected in the regeneration sample and the equivalents of PrPsc bound to the PRDT resin was discussed in more detail in the section of calculation of the prion binding capacity of the PRDT resin below.

Calculation of the Prion Binding Capacity of the Prion Reduction Resins

In order to estimate the binding capacity for the prion reduction resins (PRDT resin) for infectious prion protein, the titres observed in the Western blot testing were related to infectious titres. The Western blot assay used a 263K stock of known titre. A dilution series of the reference stock was prepared and tested in the Western blot assay. After plotting the obtained titres versus the respective titres observed in the hamster bioassay, a linear regression analysis was performed to assess the relation between the two test systems. The slope and intercept for the regression line were calculated to be 1.0667 and −4.5867, respectively. The regression parameters were used to convert Western blot titres into infectious titres using the following formula:

$$\text{Titre}_{[Bioassay]} = (\text{Titre}_{[WesternBlot]} + 4.5867)/(1.0667).$$

Once the infectious titre per ml was calculated, the total prion bound to the column was determined. The calculated prion protein binding capacity of the PRDT resin is shown in the Table 14 below. The capacity was determined using the amount of PrPsc observed directly bound to the PRDT resin (samples Reg and Col).

TABLE 13

Summary of Sample Titration Data and Prion Reduction Factors

| Sample ID | Sample Description | Log dilution for interference | End point titre | Sample Volume at collection | Volume Further Processed | Correction Factor for Volume processed* | Volume of Samples Before pH Adjustment | Volume of Samples After pH Adjustment | pH Adjustment Correction Factor | Log volume | Total Load |
|---|---|---|---|---|---|---|---|---|---|---|---|
| SP0912-SSM | Spiked start material | 0.0 | 2.0 | 50.6 ml | 50.2 ml | 0.99 | 50.6 ml | 50.7 ml | 1.00 | 1.7 | 3.702 |
| SP0912-E1 | Eluate Fraction 1 | 0.0 | 0.0 | 50.2 ml | — | | | | — | 1.7 | ≤1.701 |
| SP0912-E2 | Eluate Fraction 2 | 0.0 | 0.5 | 50.2 ml | — | | | | — | 1.7 | 2.201 |
| SP0912-E3 | Eluate Fraction 3 | 0.0 | 1.0 | 50.2 ml | — | | | | — | 1.7 | 2.701 |
| SP0912-E4 | Eluate Fraction 4 | 0.0 | 1.0 | 50.2 ml | — | | | | — | 1.7 | 2.701 |
| SP0912-E5 | Eluate Fraction 5 | 0.0 | 1.0 | 50.2 ml | — | | | | — | 1.7 | 2.701 |
| SP0912-Reg | Regeneration Fraction | 0.5 | 0.0 | 25.1 ml | — | | | | — | 1.4 | ≤1.900 |
| SP0912-Col | Column Resin | 0.0 | 3.0 | 8.7 ml | — | | | | — | 0.9 | 3.940 |

| | | Sample # | Sample ID | Sample Description | Log Titre | RF |
|---|---|---|---|---|---|---|
| Reduction Factor 1: | | Sample 1 | SP0912-SSM | Spiked start material | 3.702 | |
| | | Sample 2 | SP0912-E1 | Eluate Fraction 1 | 1.701 | ≥2.00 |
| | | Comments: | | RF for eluate 1 relative to spiked start material | | |
| Reduction Factor 2: | | Sample 1 | SP0912-SSM | Spiked start material | 3.702 | |
| | | Sample 6 | SP0912-E5 | Eluate Fraction 5 | 2.701 | 1.00 |
| | | Comments: | | RF for eluate 5 relative to spiked start material | | |

*Correction factors are applied in the final log volume calculation. The correction factors applicable for each sample are the correction factors of the respective sample itself along with all correction factors for samples listed below that sample.
**A volume of 50 ml was used for the purpose of calculating the reduction factor for each eluate sample, to ensure a direct comparison with the volume loaded onto the column.

TABLE 14

Prion binding capacity of PRDT Resin

| Sample ID | Sample Description | Total PrP$^{sc}$ (log$_{10}$$^{WB}$)$^{\#}$ | Infectious PrPsc (log$_{10}$ ID$_{50}$ total) = Total PrPsc + 4.1 | Binding capacity per ml (ID$_{50}$/ml)* |
|---|---|---|---|---|
| Albumin spiked with a sarkosyl solubilized spike | | | | |
| SP0912-SSM | 50 ml plasma spiked with 0.5 ml of a sarkosyl solubilized spike 5.0 ml PRDT Resin; 50 ml of SP0912-SSM sample loaded (Target flow rate: 1.8 ml/min) | 3.7♣ | 7.8 | — |
| SP0912-Reg | 2M NaCl salt wash (sample volume 25.1 ml) | ≤1.9 | ≤6.0 | ≤5.3 log$_{10}$/ml |
| SP0912-Col | Column resin (sample volume 8.7 ml) | 3.9 | 8.0 | 7.3 log$_{10}$/ml |

$^{\#}$Total PrPSc includes corrections for volume of sample as well as concentration/dilution prior to testing
♣ Total load based on a final volume of 50 ml loaded onto the PRDT column * Based on a 5.0 ml column size The total binding of PrPsc to the PRDT matrix following a 2M salt wash was 7.4 log$_{10}$ ID$_{50}$/ml. No PrPsc was detected in the salt wash fractions by Western blot. Significant PrPsc removal (≥2.0 log$_{10}$) was also observed.

The pH of the spiked starting material was 6.85. After the addition of 65 µl 0.1M NaOH and 50 µl 1M NaOH the pH value remained unchanged. The effect probably resulted from the significant buffering capacity of 25% albumin.

When performing interference testing, the starting material was tested undiluted, with centrifugation and 10-fold concentration. This was in addition to the interference testing described in the study plan, and was performed to allow an evaluation of the possibility for concentrating the samples and thus achieving higher reduction factors.

Example 5

In-Process and Stability Analyses for Human Albumin Treated with Prion Removal

In this experiment, the effect of prion-removal column on the concentration and composition of human albumin was evaluated. In two separate experiments, one liter of albumin was treated with the PRIOCLEAR™ B column (50 ml) (ProMetic Biosciences). The untreated sample, sample collected at the beginning of the run, and sample collected at the end of the run were then subject to concentration and composition analyses. The results are shown in Tables 15 and 16.

TABLE 15

Result for Human Albumin in Experiment One

| Sample Description | HA Concentration, mg/mL | HA Composition (%) | | | |
|---|---|---|---|---|---|
| | | Monomer | Dimer | Polymer | Oligomer |
| HA, Untreated | 252 | 93.73 | 2.71 | 3.56 | ND |
| HA Post Prion-removal Column, Sample Collected at the Beginning of Run | 253 | 93.93 | 2.71 | 3.36 | ND |
| HA Post Prion-removal Column, Sample Collected at the End of Run (1 L) | 255 | 93.76 | 2.72 | 3.52 | ND |

TABLE 16

Result for Human Albumin in Experiment Two

| Sample Description | HA Concentration, mg/mL | HA Composition (%) | | | |
|---|---|---|---|---|---|
| | | Monomer | Dimer | Polymer | Oligomer |
| HA, Untreated | 206 | 92.15 | 3.08 | 4.34 | 0.44 |
| HA Post Prion-removal Column, Sample Collected at the Beginning of Run | 181 | 92.26 | 3.05 | 4.27 | 0.42 |
| HA Post Prion-removal Column, Sample Collected at the End of Run (1 L) | 206 | 92.19 | 3.08 | 4.30 | 0.43 |

No significant differences on the albumin were observed before and after the prion removal process.

We further evaluated the in-process stability of human albumin treated for prion-removal and Abraxane® suspensions manufactured using the human albumin treated for prion-removal. The result is shown in Tables 17 and 18.

TABLE 17

In-process Stability of Treated HA Solutions from Experiment One and Abraxane Suspensions Manufactured using Treated HA

| Sample Description | Storage Conditions | HA Concentration, mg/mL | HA Composition (%) | | | |
|---|---|---|---|---|---|---|
| | | | Monomer | Dimer | Polymer | Oligomer |
| Concentrated HA Solution | 0-time | 255 | 93.79 | 2.73 | 3.48 | ND |
| | 24 hrs at 5° C. | 257 | 93.76 | 2.74 | 3.50 | ND |
| | 48 hrs at 5° C. | 255 | 93.74 | 2.77 | 3.49 | ND |
| | 72 hrs at 5° C. | 255 | 93.76 | 2.73 | 3.50 | ND |
| Diluted HA Solution | 0-time | 51 | 93.79 | 2.73 | 3.47 | ND |
| | 24 hrs at 5° C. | 51 | 93.82 | 2.71 | 3.47 | ND |
| | 48 hrs at 5° C. | 51 | 93.83 | 2.70 | 3.47 | ND |
| | 72 hrs at 5° C. | 51 | 93.85 | 2.69 | 3.46 | ND |
| Abraxane ® Suspension before Lyophilization | 0-time | 57 | 88.39 | 7.14 | 3.26 | 1.22 |
| | 24 hrs at 25° C. | 57 | 86.32 | 8.19 | 3.25 | 2.25 |
| | 36 hrs at 25° C. | 55 | 88.22 | 8.44 | 2.13 | 1.21 |

TABLE 18

In-process Stability of Treated HA Solutions from Experiment Two and Abraxane Suspensions Manufactured using Treated HA

| Sample Description | Storage Conditions | HA Concentration, mg/mL | HA Composition (%) | | | |
|---|---|---|---|---|---|---|
| | | | Monomer | Dimer | Polymer | Oligomer |
| Concentrated HA Solution | 0-time | 206 | 92.22 | 3.09 | 4.25 | 0.44 |
| | 24 hrs at 5° C. | 202.7 | 92.28 | 3.03 | 4.26 | 0.43 |
| | 48 hrs at 5° C. | 204.1 | 92.32 | 2.99 | 4.25 | 0.44 |
| | 72 hrs at 5° C. | 200.3 | 92.14 | 3.06 | 4.35 | 0.44 |
| Diluted HA Solution | 0-time | 51.4 | 92.28 | 3.04 | 4.26 | 0.42 |
| | 24 hrs at 5° C. | 51.1 | 92.30 | 3.01 | 4.27 | 0.43 |
| | 48 hrs at 5° C. | 52.1 | 92.38 | 2.95 | 4.24 | 0.43 |
| | 72 hrs at 5° C. | 51.7 | 92.45 | 2.93 | 4.22 | 0.41 |
| Abraxane ® Suspension before Lyophilization | 0-time | 57 | 85.78 | 8.30 | 3.97 | 1.94 |
| | 24 hrs at 25° C. | 57.1 | 85.28 | 8.67 | 3.95 | 2.10 |
| | 36 hrs at 25° C. | 57.4 | 87.72 | 7.62 | 3.43 | 1.23 |

We further compared the accelerated stability of human albumin in finished Abraxane® products manufactured using human albumin treated for prion-removal (Pilot plant batch using human albumin treated for Prion removal) and finished Abraxane® products manufactured using human albumin not treated for prion-removal (Abraxane Exhibit lot, Abraxane Validation lot, and Abraxane pilot plant batch). The result is shown in Table 19.

TABLE 19

Accelerated Stability of HA in Abraxane Finished Products Manufactured using HA Treated for Prion-removal. Comparison with Finished Products Manufacturing using Untreated HA

| Sample Description | Experiments | Storage Conditions | HA Composition | | | | | | | |
|---|---|---|---|---|---|---|---|---|---|---|
| | | | Monomer | | Dimer | | Polymer | | Oligomer | |
| | | | % | Change During Storage | % | Change During Storage | % | Change During Storage | % | Change During Storage |
| Pilot Plant Batch using HA Treated for Prion Removal | Experiment 1 | 0-time | 84.66 | N/A | 9.33 | N/A | 2.76 | N/A | 3.25 | N/A |
| | | 2 W at 55° C. | 70.39 | −14.27 | 17.16 | 7.83 | 8.77 | 6.01 | 3.67 | 0.42 |
| | | 1 M at 55° C. | 61.83 | −22.83 | 19.34 | 10.01 | 14.55 | 11.79 | 4.27 | 1.02 |
| | | 1 M at 40° C. | 76.22 | −8.44 | 14.58 | 5.25 | 5.71 | 2.95 | 3.49 | 0.24 |

TABLE 19-continued

Accelerated Stability of HA in Abraxane Finished Products
Manufactured using HA Treated for Prion-removal. Comparison with Finished Products
Manufacturing using Untreated HA

| | | | \multicolumn{8}{c}{HA Composition} | | | | | | | |
|---|---|---|---|---|---|---|---|---|---|---|
| | | | Monomer | | Dimer | | Polymer | | Oligomer | |
| Sample Description | Experiments | Storage Conditions | % | Change During Storage | % | Change During Storage | % | Change During Storage | % | Change During Storage |
| Abraxane Exhibit Lot | Experiment 1 | 0-time | 86.70 | N/A | 9.40 | N/A | 2.1 | N/A | 2.50 | N/A |
| | | 3 M at 40° C. | 71.20 | −15.50 | 17.20 | 7.80 | 8.9 | 6.80 | 2.70 | 0.20 |
| | | 3 M at 40° C. | 63.90 | −22.80 | 19.30 | 9.90 | 13.9 | 11.80 | 3.00 | 0.50 |
| Pilot Plant Batch using HA Treated for Prion Removal | Experiment 2 | 0-time | 84.44 | N/A | 9.03 | N/A | 2.32 | N/A | 4.17 | N/A |
| | | 2 W at 55° C. | 72.43 | −12.01 | 16.02 | 6.99 | 7.12 | 4.80 | 4.39 | 0.22 |
| Abraxane Process Validation Lot | Experiment 2 | 0-time | 86.70 | N/A | 7.00 | N/A | 1.5 | N/A | 4.80 | N/A |
| | | 3 M at 40° C. | 75.60 | −11.10 | 14.30 | 7.30 | 5.4 | 3.90 | 4.70 | −0.10 |
| | | 6 M at 40° C. | 68.80 | −17.90 | 16.80 | 9.80 | 9.2 | 7.70 | 5.20 | 0.40 |
| Abraxane Pilot Plant Batch | Experiments 1 and 2 | 0-time | 89.45 | N/A | 5.73 | N/A | 1.33 | N/A | 3.5 | N/A |
| | | 2 W at 55° C. | 75.19 | −14.26 | 14.92 | 9.19 | 6.21 | 4.88 | 3.68 | 0.18 |

Comparison of stability data shows that storage for 2 weeks at 55° C. is equivalent to storage for 3 months at 40° C. No significant differences were observed during the manufacturing process and during the in-process testing between pilot plant batches manufactured using human albumin treated for prion removal and pilot plant batches manufactured using untreated human albumin. There were no significant differences between the properties of the finished products manufactured using human albumin treated for prion removal and the properties of the finished product manufactured using untreated human albumin Example 6

Evaluation of the Effect of Prion-Removal Column on Abraxane® in-Process Suspension This experiment evaluates the effect of prion removal from Abraxane® in-process suspension, namely, the suspension of Abtaxane® prior to lyophilization. Commercially available PIKSI kit columns (1 cc), containing Toyopearl Amino 650CU resin, ProMetic Biosciences was used in this experiment.

In two separate experiments, 0.5 L Abraxane® in process suspension containing human albumin were processed through the column. The analysis results are summarized in Table 20.

TABLE 20

Effect of Prion-Removal Column on Abraxane In-Process Suspension

| | HA | | | | | | Impurities, % | | | | | | |
|---|---|---|---|---|---|---|---|---|---|---|---|---|---|
| Sample | Conc., | \multicolumn{4}{c}{HA Composition, %} | Paclitaxel, | 7- | | \multicolumn{4}{c}{Particle size, nm} | |
| No. | mg/mL | Monomer | Dimer | Polymer | Oligomer | mg/mL | Epipaclitaxel | Total | Mean | <5% | <95% | <99.9% | pH |
| 1 | 55 | 88.29 | 5.95 | 3.99 | 1.32 | 6.9 | 0.08 | 0.25 | 131 | 82 | 193 | 254 | 7.0 |
| 2 | 56 | 88.37 | 5.96 | 3.86 | 1.36 | 6.9 | 0.08 | 0.25 | 132 | 86 | 190 | 250 | 7.0 |
| 3 | 56 | 88.38 | 5.96 | 3.76 | 1.39 | 6.8 | 0.09 | 0.26 | 130 | 82 | 190 | 250 | 7.0 |

Sample 1: Abraxane In-Process Suspension, Untreated
Sample 2: Abraxane In-Process Suspension, post Prion-removal Column, sample Collected at the Beginning of Run
Sample 3: Abraxane In-Process Suspension, post Prion-removal Column, sample Collected at the End of Run (0.5 L).

As shown in Table 20, the physical and chemical testing of Abraxane® in-process suspension treated for prion removal show no significant differences between the untreated and treated suspension, in terms of particle size, pH, paclitaxel assay and impurities, human albumin (HA) assay, and HA composition.

What is claimed is:

1. A method of removing prion proteins from a composition comprising nanoparticles comprising a substantially water insoluble pharmacologically active agent coated with albumin, wherein said method comprises:

(a) providing a suspension of nanoparticles comprising a substantially water insoluble pharmacologically active agent coated with albumin; and (b) treating said suspension of nanoparticles provided in step (a) by passing said suspension of nanoparticles through a chromatography column, wherein the column comprises a ligand capable of binding to a prion protein, wherein there are no significant differences between the treated and untreated suspensions in terms of particle size and pH.

2. The method of claim 1, wherein said ligand is a peptide.

3. The method of claim 1, wherein the ligand is a triazine-based compound.

4. The method of claim 1, wherein the water insoluble pharmacologically active agent is paclitaxel.

5. The method of claim 1, wherein the nanoparticle suspension treated by step (b) does not show the presence of a prion protein based on the protein misfolding cyclic amplification assay.

6. The method of claim 1, wherein the nanoparticle suspension treated by step (b) does not show the presence of a prion protein based on an immune-polymerase chain reaction assay used to detect prion proteins.

7. The method of claim 1, wherein the nanoparticle suspension treated by step (b) is substantially free of cellular prion protein in the normal and abnormal isoforms.

8. The method of claim 1, wherein said nanoparticles further comprise a negatively charged component.

9. The method of claim 8, wherein said nanoparticles have a negative zeta potential.

10. The method of claim 8, wherein the negatively charged component is selected from the group consisting of bile acids, glycocholic acid, cholic acid, chenodeoxycholic acid, autorcholic acid, glycochenodeoxycholic acid, taurodeoxycholic acid, lithocholic acid, ursodeoxycholic acid, dehydrocholic acid, sodium cholesteryl sulfate, and combinations thereof.

* * * * *